(12) United States Patent
Lockman et al.

(10) Patent No.: US 9,056,836 B2
(45) Date of Patent: Jun. 16, 2015

(54) BENZOMORPHAN ANALOGS AND THE USE THEREOF

(71) Applicant: Purdue Pharma L.P., Stamford, CT (US)

(72) Inventors: Jeffrey Lockman, Princeton Junction, NJ (US); Jae Hyun Park, Princeton, NJ (US); Laykea Tafesse, Robbinsville, NJ (US); Jiangchao Yao, Princeton, NJ (US); Jianming Yu, Plainsboro, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 14/168,488

(22) Filed: Jan. 30, 2014

(65) Prior Publication Data

US 2014/0221419 A1   Aug. 7, 2014

Related U.S. Application Data

(60) Provisional application No. 61/759,234, filed on Jan. 31, 2013.

(51) Int. Cl.
*A61K 31/44* (2006.01)
*C07D 221/22* (2006.01)
*C07D 221/26* (2006.01)

(52) U.S. Cl.
CPC .................................. *C07D 221/26* (2013.01)

(58) Field of Classification Search
None
See application file for complete search history.

(56) References Cited

U.S. PATENT DOCUMENTS

| | | | | |
|---|---|---|---|---|
| 3,764,606 A | * | 10/1973 | Akkerman et al. | 546/97 |
| 4,016,167 A | * | 4/1977 | Montzka et al. | 546/18 |
| 4,100,164 A | * | 7/1978 | Michne | 546/74 |

(Continued)

FOREIGN PATENT DOCUMENTS

| FR | 1355144 A | 3/1964 |
|---|---|---|
| WO | WO-2013/167963 A1 | 11/2013 |

OTHER PUBLICATIONS

CAPLUS 1963:469018.*

(Continued)

*Primary Examiner* — Heidi Reese
(74) *Attorney, Agent, or Firm* — Purdue Pharma L.P.; Alan L. Koller; Weiying Yang

(57) ABSTRACT

The present invention is directed to Benzomorphan Analog compounds of the Formula I-ID as shown below, wherein $R^1$, $R^{2a}$, $R^{2b}$, $R^3$ and $R^4$ are as defined herein.

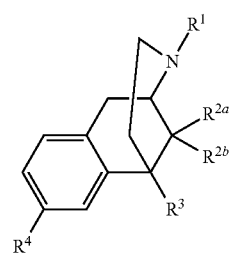

I

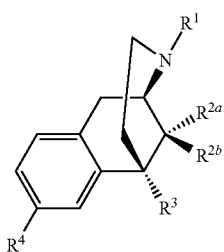

IA

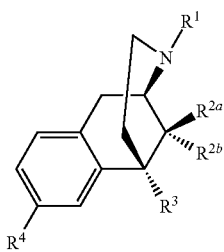

IB

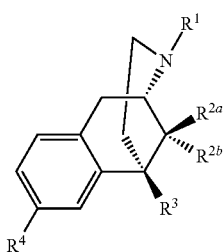

IC

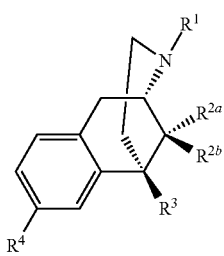

ID

Compounds of the Invention are useful for treating pain, constipation, and other conditions modulated by activity of opioid and ORL-1 receptors.

22 Claims, No Drawings

(56) References Cited

U.S. PATENT DOCUMENTS

| | | | |
|---|---|---|---|
| 4,154,932 | A | 5/1979 | Montzka et al. |
| 4,202,984 | A | 5/1980 | Lewis et al. |
| 4,228,285 | A | 10/1980 | Montzka et al. |
| 4,239,890 | A * | 12/1980 | Michne ............... 546/74 |
| 4,255,579 | A | 3/1981 | Michne |
| 4,288,444 | A * | 9/1981 | Akkerman et al. ........... 514/295 |
| 4,366,325 | A | 12/1982 | Wedemeyer et al. |
| 4,406,904 | A | 9/1983 | Welle et al. |
| 4,425,353 | A * | 1/1984 | Akkerman et al. ........... 514/295 |
| 6,740,641 | B2 | 5/2004 | Gao et al. |
| 6,825,205 | B2 | 11/2004 | Kyle |
| 6,958,398 | B1 | 10/2005 | Kupper et al. |
| 7,084,150 | B2 | 8/2006 | Boer et al. |
| 7,125,884 | B2 | 10/2006 | Reidenberg et al. |
| 7,202,259 | B2 | 4/2007 | Chen |
| 7,687,518 | B2 | 3/2010 | Chen |
| 8,026,254 | B2 | 9/2011 | Chen |
| 8,426,594 | B2 | 4/2013 | Kyle |
| 8,481,743 | B2 | 7/2013 | Zhou |
| 8,530,494 | B2 | 9/2013 | Kyle et al. |
| 8,937,084 | B2 | 1/2015 | Park et al. |
| 8,946,255 | B2 | 2/2015 | Kassick et al. |
| 8,957,084 | B2 | 2/2015 | Kyle et al. |
| 8,969,358 | B2 | 3/2015 | Goehring et al. |
| 8,980,906 | B2 | 3/2015 | Tafesse |
| 2014/0057931 | A1 | 2/2014 | Kyle et al. |
| 2014/0057932 | A1 | 2/2014 | Reisch |
| 2014/0135351 | A1 | 5/2014 | Lockman et al. |
| 2014/0163058 | A1 | 6/2014 | Youngman |
| 2014/0179724 | A1 | 6/2014 | Goehring et al. |
| 2014/0364448 | A1 | 12/2014 | Kyle |

OTHER PUBLICATIONS

CAPLUS 1964:418192.*
CAPLUS 1984:543978.*
CAPLUS 1962:73616.*
K.M. Foley, Pain, in Cecil Textbook of Medicine 100-107, J.C. Bennett and F. Plum eds., 20th ed. 1996.
Gutstein, Howard B., Akil, Huda, "Chapter 21. Opioid Analgesics" (Chapter 21), Brunton, LL, Lazo, JS, Parker, KI: Goodman & Gilman's The Pharmacological Basis of Therapeutics, 11th Edition: http://www.accessmedicine.com/content.aspx?aID=940653, 2006.
C. Altier et al., "ORL-1 receptor-mediated internalization of N-type calcium channels." Nature Neuroscience, 2005, 9:31.
D. Barlocco et al., "The opioid-receptor-like 1 (ORL-1) as a potential target for new analgesics." Eur. J. Med. Chem., 2000, 35:275.
J.S. Mogil et al., "Orphanin FQ is a functional anti-opioid peptide." Neurosci., 1996, 75:333.
K. Lutfy et al., "Tolerance develops to the inhibitory effect of orphanin FQ on morphine-induced antinociception in the rat." NeuroReport, 1999, 10:103.
M.M. Morgan et al., "Antinociception mediated by the periaqueductal gray is attenuated by orphanin FQ." NeuroReport, 1997, 8:3431.
J. Tian et al., "Involvement of endogenous Orphanin FQ in electroacupuncture-induced analgesia." NeuroReport, 1997, 8:497.
J. Tian et al., "Functional studies using antibodies against orphanin FQ/nociceptin." Peptides, 2000, 21:1047.
H. Ueda et al., "Enhanced Spinal Nociceptin Receptor Expression Develops Morphine Tolerance and Dependence." J. Neurosci., 2000, 20:7640.
Wood & Galligan, Function of opioids in the enteric nervous system. Neurogastroenterology & Motility 16 (Suppl.2): 17-28, 2004.
Y. K. Sawa et al., "Elimination of the 4-Hydroxyl Group of the Alkaloids Related to Morphine-VII: Synthesis of the Active 2'-Hydroxy-2-Methyl-5,9-Diethyl-6,7-Benzomorphan Derivatives." Tetrahedron, 1965, 21 (5) 1129-1132.
International Search Report mailed Apr. 16, 2014 in corresponding International Application No. PCT/IB2014/000094 and Written Opinion.

* cited by examiner

BENZOMORPHAN ANALOGS AND THE USE THEREOF

This application claims the benefit of U.S. Provisional Application Ser. No. 61/759,234, filed Jan. 31, 2013.

FIELD OF THE INVENTION

The invention is in the field of medicinal chemistry. It relates to novel benzomorphan analogs having activity as opioid receptor agonists and/or antagonists. In certain embodiments, compounds of the invention have dual activity as opioid agonists and ORL-1 receptor antagonists.

BACKGROUND OF THE INVENTION

Pain is the most common symptom for which patients seek medical advice and treatment. While acute pain is usually self-limited, chronic pain can persist for 3 months or longer and lead to significant changes in a patient's personality, lifestyle, functional ability and overall quality of life (K. M. Foley, Pain, in *Cecil Textbook of Medicine* 100-107, J. C. Bennett and F. Plum eds., 20th ed. 1996).

Pain has traditionally been managed by administering either a non-opioid analgesic (such as acetylsalicylic acid, choline magnesium trisalicylate, acetaminophen, ibuprofen, fenoprofen, diflunisal or naproxen), or an opioid analgesic (such as morphine, hydromorphone, methadone, levorphanol, fentanyl, oxycodone or oxymorphone).

Although the term "narcotic" is often used to refer to opioids, the term is not specifically applicable to opioids. The term "narcotic", derived from the Greek word for "stupor", originally referred to any drug that induced sleep, only later being associated with opioids (Gutstein, Howard B., Akil, Huda, "Chapter 21. Opioid Analgesics" (Chapter 21), Brunton, LL, Lazo, JS, Parker, KI: Goodman & Gilman's The Pharmacological Basis of Therapeutics, 11$^{th}$ Edition). In the legal context, the term "narcotic" refers to a variety of mechanistically unrelated substances with abuse or addictive potential (Gutstein, Howard B., Akil, Huda, "Chapter 21. Opioid Analgesics" (Chapter 21), Brunton LL, Lazo JS, Parker KI: Goodman & Gilman's The Pharmacological Basis of Therapeutics, 11$^{th}$ Edition). Thus, the term "narcotic" not only refers to opioids, but also refers to such drugs as cocaine, methamphetamine, ecstasy, etc., which exert their pharmacological effects via different receptors than opioids. Furthermore, because the term "narcotic" refers to such a wide variety of unrelated drugs, many of which do not possess analgesic properties, it cannot be assumed that a drug that has "narcotic" properties is necessarily analgesic. For example, drugs such as ecstasy and methamphetamine are not analgesic, and are not used to treat pain.

Until recently, there was evidence of three major classes of opioid receptors in the central nervous system (CNS), with each class having subtype receptors. These receptor classes are known as $\mu$, $\delta$ and $\kappa$. As opiates have a high affinity to these receptors while not being endogenous to the body, research followed in order to identify and isolate the endogenous ligands to these receptors. These ligands were identified as endorphins, enkephalins, and dynorphins, respectively. Additional experimentation has led to the identification of the opioid receptor-like (ORL-1) receptor, which has a high degree of homology to the known opioid receptor classes. This newly discovered receptor was classified as an opioid receptor based only on structural grounds, as the receptor did not exhibit pharmacological homology. It was initially demonstrated that non-selective ligands having a high affinity for $\mu$, $\delta$ and $\kappa$ receptors had low affinity for the ORL-1 receptor. This characteristic, along with the fact that an endogenous ligand had not yet been discovered, led to the ORL-1 receptor being designated as an "orphan receptor".

Subsequent research led to the isolation and structure of the endogenous ligand of the ORL-1 receptor. This ligand, nociceptin (also known as orphanin FQ (OFQ)), is a seventeen amino acid peptide structurally similar to members of the opioid peptide family. (C. Altier et al., "ORL-1 receptor-mediated internalization of N-type calcium channels." *Nature Neuroscience*, 2005, 9:31).

The discovery of the ORL-1 receptor and its endogenous ligand, presents an opportunity for the discovery of novel compounds that can be administered for pain management or other syndromes influenced by this receptor.

Many publications in the ORL-1/nociceptin field provide evidence that activation of ORL-1 receptors in the brain can inhibit opioid-mediated analgesia (e.g., D. Barlocco et al., "The opioid-receptor-like 1 (ORL-1) as a potential target for new analgesics," *Eur. J. Med. Chem.*, 2000, 35:275; J. S. Mogil et al., "Orphanin FQ is a functional anti-opioid peptide." *Neurosci.*, 1996, 75:333; K. Lutfy et al., "Tolerance develops to the inhibitory effect of orphanin FQ on morphine-induced antinociception in the rat." *NeuroReport*, 1999, 10:103; M. M. Morgan et al., "Antinociception mediated by the periaqueductal gray is attenuated by orphanin FQ." *NeuroReport*, 1997, 8:3431; and J. Tian et al., "Involvement of endogenous Orphanin FQ in electroacupuncture-induced analgesia." *NeuroReport*, 1997, 8:497).

A growing body of evidence supports a more generalized regulatory role for ORL-1 against the actions of the $\mu$ receptor, possibly contributing to the development of $\mu$-agonist tolerance in patients being treated with classical opiates (e.g., J. Tian et al., "Functional studies using antibodies against orphanin FQ/nociceptin." *Peptides*, 2000, 21:1047; and H. Ueda et al., "Enhanced Spinal Nociceptin Receptor Expression Develops Morphine Tolerance and Dependence," *J. Neurosci.*, 2000, 20:7640). Moreover, ORL-1 activation appears to have an inhibitory effect on the rewarding properties of several drugs of abuse, including $\mu$ agonists. Use of opioid analgesics often leads to constipation as a side effect. Constipation associated with the use of opioid analgesics is presumed to occur primarily and mechanistically as a result of the action of mu opioid agonists directly upon mu opioid receptors located in the bowel (Wood & Galligan (2004), Function of opioids in the enteric nervous system. *Neurogastroenterology & Motility* 16(Suppl.2): 17-28.). Stimulation of the mu opioid receptors in the bowel causes inhibition of normal gastrointestinal (GI) motility, leading to constipation. The effect of $\mu$ opioid agonism on $\mu$ opioid receptors in the bowel can be observed via the action of loperamide (Imodium™) in treating diarrhea. Loperamide is a potent $\mu$ opioid agonist that is administered orally, but which has little to no absorption into the blood stream. As a result, loperamide exerts its action locally upon the $\mu$ opioid receptors in the bowel, and this results in inhibition of GI motility, which treats diarrhea.

There has been recent interest in developing combinations of $\mu$ receptor agonists and antagonists having defined biodistribution properties that might serve to limit opioid-induced constipation. For example, the co-administration of an orally bio-available $\mu$ opioid receptor agonist (such as morphine, codeine, oxycodone or hydromorphone) together with a potent $\mu$ opioid receptor antagonist (such as N-methylnaloxone or N-methylnaltrexone) that is not orally bio-available may serve to prevent or reduce the constipation otherwise associated with mu opioid receptor agonist therapy. The rationale is that the agonist component will be absorbed and distributed throughout the periphery and the central nervous system (CNS), resulting in the desired analgesia, while the antagonist component will remain in the bowel where it will prevent or reduce any agonist-induced constipation that might otherwise occur.

Benzomorphan analog compounds, such as 3,11,11-trimethyl-1,2,3,4,5,6-hexahydro-2,6-methanobenzo[d]azocine-6,8-diol and 8-methoxy-3,11,11-trimethyl-1,2,3,4,5,6-hexahydro-2,6-methanobenzo[d]azocin-6-ol, having analgesic activity have been described (see, e.g. U.S. Pat. Nos. 4,425,353; 4,406,904; and 4,366,325).

BRIEF SUMMARY OF THE INVENTION

The present invention provides novel benzomorphan analog compounds useful for treating a variety of Conditions, including pain, in particular chronic pain, and constipation. More specifically, the present invention provides compounds of Formula I, Formula IA, Formula IB, Formula IC, and Formula ID, and Formula I', IA', IB', IC', and ID' below, and the pharmaceutically acceptable salts and solvates thereof, that exhibit affinity for one or more of the ORL-1, μ, δ and κ opioid receptors. Such compounds, salts, and solvates are collectively referred to hereinafter as "Compounds of the Invention" (each is individually referred to hereinafter as a "Compound of the Invention").

In a particular aspect, the present invention provides novel compounds of Formula I:

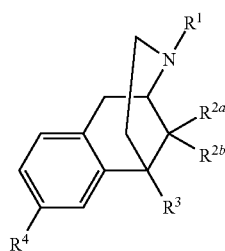

I wherein $R^1$ is selected from the group consisting of —$(C_1-C_{10})$alkyl, —$(C_2-C_{12})$alkenyl, —$(C_2-C_{12})$alkynyl, —$(C_3-C_{12})$cycloalkyl, $(C_3-C_{12})$cycloalkyl-$(C_1-C_6)$alkyl-, —$(C_3-C_{12})$cycloalkenyl, $(C_3-C_{12})$cycloalkenyl-$(C_1-C_6)$alkyl-, -(6- to 14-membered)aryl, ((6- to 14-membered)aryl)-$(C_1-C_6)$alkyl-, diphenyl$(C_1-C_6)$alkyl-, —$(OCH_2CH_2)_s$—O—$(C_1-C_6)$alkyl, —$(CH_2CH_2O)_s$—$(C_1-C_6)$alkyl, —$(C_1-C_{10})$alkoxy, —$C(halo)_3$, —$CH(halo)_2$, —$CH_2(halo)$, —$C(=O)R^5$, —$C(=O)$—O—$(C_1-C_{10})$alkyl, —$C(=O)$—N—$(R^6)_2$ and —$(CH_2)_n$—$N(R^6)_2$, each of which is optionally substituted by 1, 2 or 3 independently selected $R^9$ groups;

$R^{2a}$ is absent, or selected from the group consisting of OH, —$(C_1-C_6)$alkyl and hydroxy$(C_1-C_6)$alkyl-;

$R^{2b}$ is selected from the group consisting of:
a) -(6- to 14-membered)aryl or -(3- to 12-membered)heterocycle, each of which is optionally substituted with one, two, or three independently selected $R^{30}$ groups; and
b) —Z-G-$R^{10}$;

or $R^{2a}$ and $R^{2b}$ together form =O;

$R^3$ is selected from the group consisting of:
a) -(6- to 14-membered)aryl or -(3- to 12-membered)heterocycle, each of which is optionally substituted with one, two, or three independently selected $R^{30}$ groups; and
b) —Z-G-$R^{10}$;

wherein, each Z is independently absent or —$(CH_2)_m$—, optionally substituted with, one or two —$(C_1-C_6)$alkyl;

each G is independently selected from the group consisting of:
a) a bond, —$(C_1-C_6)$alkylene, and —$(C_2-C_6)$alkenylene;
b) O, —O—C(=O)—, —C(=O), and =CH;
c) $NR^8$, =N—O, and =N—NH; and
d) S, SO, and $SO_2$;

Each $R^{10}$ is independently selected from the group consisting of:
a) hydrogen, —$(C_1-C_{10})$alkyl, —$(C_2-C_{12})$alkenyl, —CH(=O), —C(=O)—$(C_1-C_6)$alkyl, —C(=O)$(C_2-C_6)$alkenyl, —C(=O)-(6- to 14-membered)aryl, —C(=O)—$(C_1-C_6)$alkyl-(6- to 14-membered)aryl, —$(C_2-C_{12})$alkynyl, —$(C_1-C_{10})$alkoxy, —$(OCH_2CH_2)_s$—O—$(C_1-C_6)$alkyl, —$(CH_2CH_2O)_s$—$(C_1-C_6)$alkyl, —$(C_3-C_{12})$cycloalkyl, $((C_3-C_{12})$cycloalkyl)-$(C_1-C_6)$alkyl-, —$(C_4-C_{12})$cycloalkenyl, $((C_4-C_{12})$cycloalkenyl)-$(C_1-C_6)$alkyl-, —$(C_6-C_{14})$bicycloalkyl, $((C_6-C_{14})$bicycloalkyl)-$(C_1-C_6)$alkyl-, —$(C_8-C_{20})$tricycloalkyl, $((C_8-C_{20})$tricycloalkyl)-$(C_1-C_6)$alkyl-, —$(C_7-C_{14})$bicycloalkenyl, $((C_7-C_{14})$bicycloalkenyl)-$(C_1-C_6)$alkyl-, —$(C_8-C_{20})$tricycloalkenyl, $((C_8-C_{20})$tricycloalkenyl)-$(C_1-C_6)$alkyl-, -(6- to 14-membered)aryl, ((6- to 14-membered)aryl)-$(C_1-C_6)$alkyl-; -(7- to 12-membered)bicyclic ring system, ((7- to 12-membered)bicyclic ring system)-$(C_1-C_6)$alkyl-, -(7- to 12-membered)bicyclic aryl, ((7- to 12-membered)bicyclic aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12 membered)heterocycle)-$(C_1-C_6)$alkyl-, -(7- to 12-membered)bicycloheterocycle, and ((7- to 12-membered)bicycloheterocyclo)-$(C_1-C_6)$alkyl-, each of which is optionally substituted with one, two, or three $R^{40}$ groups; and
b) —$NH_2$, —$NH(C_1-C_6)$alkyl, CN, $NR^5R^6$, —$(C_1-C_6)$alkyl-$NR^5R^6$, —$CONR^5R^6$, —$(C_1-C_6)$alkyl-$CONR^5R^6$, —$COOR^7$, —$(C_1-C_6)$alkyl-$COOR^7$, —$(C_1-C_6)$alkoxy-$COOR^7$, —C(=O)—$(CH_2)_n$—$COOR^7$, and —CO—$(CH_2)_n$—$CONR^5R^6$ each of which is optionally substituted with one, two, or three $R^{41}$ groups;

each $R^{40}$ is independently selected from the group consisting of OH, (=O), halo, —$C(halo)_3$, —$CH(halo)_2$, —$CH_2(halo)$, —$(C_1-C_6)$alkyl, halo$(C_1-C_6)$alkyl-, —$(C_2-C_6)$alkenyl, —$(C_2-C_6)$alkynyl, hydroxy$(C_1-C_6)$alkyl-, dihydroxy$(C_1-C_6)$alkyl-, —$(C_1-C_6)$alkoxy, $((C_1-C_6)$alkoxy)$CO(C_1-C_6)$alkoxy-, phenyl, benzyl, —$NH_2$, —$NH(C_1-C_6)$alkyl, —$(C_1-C_6)$alkyl-$NH(C_1-C_6)$alkyl-$R^{14}$, —CN, —SH, —$OR^{11}$, —$CONR^5R^6$, —$(C_1-C_6$alkyl)-$CONR^5R^6$, —$COOR^7$, —$(C_1-C_6)$alkyl-$COOR^7$, —$(C_1-C_6)$alkoxy-$COOR^7$, —$(OCH_2CH_2)_s$—$O(C_1-C_6)$alkyl, —$(CH_2CH_2O)_s$—$(C_1-C_6)$alkyl, $(C_1-C_6)$alkyl)sulfonyl, $((C_1-C_6)$alkyl)sulfonyl$(C_1-C_6)$alkyl-, —NH—$SO_2(C_1-C_6)$alkyl, $NH_2$—$SO_2(C_1-C_6)$alkyl-, —$N(SO_2(C_1-C_6)$alkyl$)_2$, —$C(=NH)NH_2$, —NH—CO—$(C_1-C_6)$alkyl, —NH—CO—$NH_2$, —NH—C(=O)—NH—$(C_1-C_6)$alkyl, —NH—C(=O)-(6- to 14-membered)aryl, —NH—C(=O)—$(C_1-C_6)$alkyl-(6- to 14-membered)aryl, —NH—$(C_1-C_6)$alkyl-$COOR^7$, —NH—C(=O)—$(C_1-C_6)$alkyl-CO—$OR^7$, —NH—C(=O)—$CH(NH_2)$—$(C_1-C_6)$alkyl-$COOR^7$, —$(C_3-C_{12})$cycloalkyl, $((C_3-C_{12})$cycloalkyl)-($C_1$-$C_6$)alkyl-, -(6- to 14-membered)aryl, -(6- to 14-membered)aryloxy, —($C_1$-$C_6$)alkoxy-CONR$^5$R$^6$, —NH—($C_1$-$C_6$)alkyl-CONR$^5$R$^6$, —C(=O)NH—($C_1$-$C_6$)alkyl-COOR$^7$, ((6- to 14-membered)aryl)-($C_1$-$C_6$)alkyl-; -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

each R$^{41}$ is independently selected from the group consisting of —OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, —($C_1$-$C_6$)alkyl-NH($C_1$-$C_6$)alkyl-R$^{14}$, —CONR$^{5a}$R$^{6a}$, —($C_1$-$C_6$alkyl-CONR$^{5a}$R$^{6a}$, —($C_1$-$C_6$)alkyl-COOR$^7$, —($C_1$-$C_6$)alkoxy-COOR$^7$, —(CH$_2$CH$_2$O)$_s$—($C_1$-$C_6$)alkyl, ($C_1$-$C_6$)alkyl)sulfonyl, (($C_1$-$C_6$)alkyl)sulfonyl($C_1$-$C_6$)alkyl-, —C(=NH)NH$_2$, phenyl, benzyl, —($C_3$-$C_{12}$)cycloalkyl, (($C_3$-$C_{12}$)cycloalkyl)-($C_1$-$C_6$)alkyl-, -(6- to 14-membered)aryl, -(6- to 14-membered)aryloxy, ((6- to 14-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

provided that:
a) when R$^{2a}$ is absent or OH, then R$^{2b}$ and R$^3$ are not H, —($C_1$-$C_6$)alkyl, —($C_2$-$C_6$)alkenyl, or —($C_2$-$C_6$)alkynyl, each of which is unsubstituted; or
b) when R$^{2b}$ is Z-G-R$^{10}$, and G of R$^{2b}$ is =N—O, =N—NH, or =CH, and Z of R$^{2b}$ is absent then R$^{2a}$ is absent; or
c) when R$^3$ is Z-G-R$^{10}$, and G of R$^3$ is =N—O, =N—NH, or =CH, then Z of R$^3$ cannot be absent;

R$^4$ is selected from the group consisting of:
a) —H, —OH, halo, —C(halo)$_3$, —CH(halo)$_2$, —CH$_2$(halo), —COOH, or —CONH$_2$; and
b) —($C_1$-$C_6$)alkyl, —($C_2$-$C_6$)alkenyl, —($C_2$-$C_6$)alkynyl, —(CH$_2$)$_n$—O—(CH$_2$)$_n$—CH$_3$, and —($C_1$-$C_5$)alkoxy, each of which is optionally substituted with 1, 2, or 3 independently selected R$^9$ groups;

R$^5$ and R$^6$ are each independently selected from the group consisting of:
a) hydrogen, —OH, halo, —C(halo)$_3$, —CH(halo)$_2$, and —CH$_2$(halo);
b) —($C_1$-$C_6$)alkenyl, —($C_2$-$C_6$)alkynyl, —(CH$_2$)$_n$—O—(CH$_2$)$_n$—CH$_3$, and —($C_1$-$C_6$)alkoxy, each of which is optionally substituted with 1, 2, or 3 substituents independently selected from —OH, halo, —($C_1$-$C_{10}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, —CHO, —COOH, —C(halo)$_3$, —CH(halo)$_2$, —CH$_2$(halo), —(CH$_2$)$_n$—O—(CH$_2$)$_n$—CH$_3$, phenyl, and —CONR$^{5a}$R$^{6a}$;
c) —($C_3$-$C_8$)cycloalkyl, (($C_3$-$C_8$)cycloalkyl)-($C_1$-$C_6$)alkyl-, —COOR$^7$, —($C_1$-$C_6$)alkyl-COOR$^7$, —CONH$_2$, and ($C_1$-$C_6$)alkyl-CONH—;
d) -(6- to 14-membered)aryl optionally substituted with 1, 2, or 3 independently selected R$^{30}$ groups; or
e) R$^5$ and R$^6$ together with the nitrogen atom to which they are attached form a -(4- to 8-membered)heterocycle optionally substituted with 1, 2, or 3 independently selected R$^{30}$ groups;

R$^{5a}$ and R$^{6a}$ are each independently selected from the group consisting of:
a) hydrogen, —OH, halo, —C(halo)$_3$, —CH(halo)$_2$, and —CH$_2$(halo);
b) —($C_1$-$C_6$)alkyl, —($C_2$-$C_6$)alkenyl, —($C_2$-$C_6$)alkynyl, —(CH$_2$)$_n$—O—(CH$_2$)$_n$—CH$_3$, and —($C_1$-$C_6$)alkoxy, each of which is optionally substituted with 1, 2, or 3 substituents independently selected from —OH, halo, —($C_3$-$C_{12}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, —CHO, —COOH, —C(halo)$_3$, —CH(halo)$_2$, —CH$_2$(halo), —(CH$_2$)$_n$—O—(CH$_2$)$_n$—CH$_3$, and phenyl;
c) —($C_3$-$C_8$)cycloalkyl, (($C_3$-$C_8$)cycloalkyl)-($C_1$-$C_6$)alkyl-, —COOR$^7$, —($C_1$-$C_6$)alkyl-COOR$^7$, —CONH$_2$, and ($C_1$-$C_6$)alkyl-CONH—;
d) -(6- to 14-membered)aryl optionally substituted with 1, 2, or 3 independently selected R$^{30}$ groups; or
e) R$^{5a}$ and R$^{6a}$ together with the nitrogen atom to which they are attached form a -(4- to 8-membered)heterocycle optionally substituted with 1, 2, or 3 independently selected R$^{30}$ groups;

each R$^7$ is independently selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl-($C_1$-$C_6$)alkyl-;

each R$^8$ is independently selected from the group consisting of H, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, (($C_3$-$C_{12}$)cycloalkenyl)-($C_1$-$C_6$)alkyl-, —C(=O)($C_1$-$C_6$)alkyl and SO$_2$($C_1$-$C_6$)alkyl;

each R$^9$ is independently selected from the group consisting of —OH, halo, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —CHO, —COOH, —C(halo)$_3$, —CH(halo)$_2$, CH$_2$(halo), —(CH$_2$)$_n$—O—(CH$_2$)$_n$—CH$_3$, phenyl, and —CONR$^{5a}$R$^{6a}$;

each R$^{11}$ is independently selected from the group consisting of —C(halo)$_3$, —CH(halo)$_2$, —CH$_2$(halo), —($C_1$-$C_6$)alkyl, —($C_2$-$C_6$)alkenyl, —($C_2$-$C_6$)alkynyl, —(CH$_2$)$_n$—O—(CH$_2$)$_n$—CH$_3$, -(6- to 14-membered)aryl, ((6-to 14-membered)aryl)-($C_1$-$C_6$)alkyl-, -(5- to 12-membered)heteroaryl, and ((5- to 12-membered)heteroaryl)-($C_1$-$C_6$)alkyl-, each of which is optionally substituted with 1, 2, or 3 independently selected R$^9$ groups;

each R$^{14}$ is independently selected from the group consisting of —COOR$^7$, —($C_1$-$C_6$)alkyl-COOR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONR$^{5a}$R$^{6a}$, and —($C_1$-$C_6$)alkyl-CONR$^{5a}$R$^{6a}$;

each R$^{30}$ is independently selected from —COOR$^7$, —CONR$^{5a}$R$^{6a}$, —($C_1$-$C_6$)alkyl, CN, -(3- to 12-membered)heteroaryl, ((3- to 12-membered)heteroaryl)-($C_1$-$C_6$)alkyl-, NH$_2$, halo, and ((6- to 14-membered)aryl)-($C_1$-$C_6$)alkoxy-;

m is an integer 1, 2, 3, 4, 5, or 6;

n is an integer 0, 1, 2, 3, 4, 5, or 6;

s is an integer 1, 2, 3, 4, 5, or 6;

and the pharmaceutically acceptable salts and solvates thereof.

In one embodiment, the present invention provides novel compounds of Formula IA:

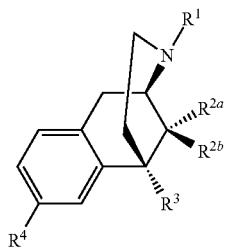

IA wherein $R^1$, $R^{2a}$, $R^{2b}$, $R^3$ and $R^4$ are as defined above for Formula I, and the pharmaceutically acceptable salts and solvates thereof.

In another embodiment, the present invention provides novel compounds of Formula IB:

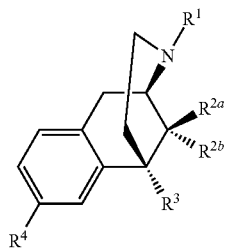

IB wherein $R^1$, $R^{2a}$, $R^{2b}$, $R^3$ and $R^4$ are as defined above for Formula I, and the pharmaceutically acceptable salts and solvates thereof.

In another embodiment, the present invention provides novel compounds of Formula IC:

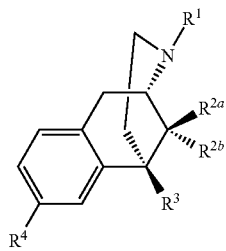

IC wherein $R^1$, $R^{2a}$, $R^{2b}$, $R^3$ and $R^4$ are as defined above for Formula I, and the pharmaceutically acceptable salts and solvates thereof.

In another embodiment, the present invention provides novel compounds of Formula ID:

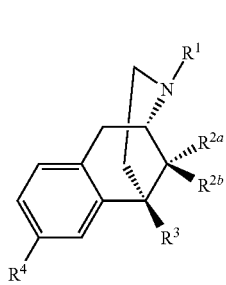

ID wherein $R^1$, $R^{2a}$, $R^{2b}$, $R^3$ and $R^4$ are as defined above for Formula I, and the pharmaceutically acceptable salts and solvates thereof.

In another aspect, the present invention provides novel compounds of Formula I';

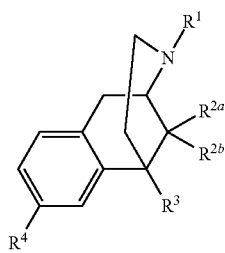

I' wherein
$R^1$ is selected from the group consisting of —$(C_1$-$C_{10})$alkyl, —$(C_2$-$C_{12})$alkenyl, —$(C_2$-$C_{12})$alkynyl, —$(C_3$-$C_{12})$cycloalkyl, $(C_3$-$C_{12})$cycloalkyl-$(C_1$-$C_6)$alkyl-, —$(C_3$-$C_{12})$cycloalkenyl, $(C_3$-$C_{12})$cycloalkenyl-$(C_1$-$C_6)$alkyl-, -(6- to 14-membered)aryl, ((6- to 14-membered)aryl)-$(C_1$-$C_6)$alkyl-, diphenyl$(C_1$-$C_6)$alkyl, —$(OCH_2CH_2)_s$—O—$(C_1$-$C_6)$alkyl, —$(CH_2CH_2O\ )_s$—$(C_1$-$C_6)$alkyl, —$(C_1$-$C_{10})$alkoxy, —C(halo)$_3$, —CH(halo)$_2$, —CH$_2$(halo), 13 C(=O)R$^5$, —C(=O)—O—$(C_1$-$C_{10})$alkyl, —C(=O)—N (R$^6$)$_2$ and —(CH$_2$)$_n$—N(R$^6$)$_2$, each of which is optionally substituted by 1, 2 or 3 independently selected R$^9$ groups;
$R^{2a}$ is hydrogen, or selected from the group consisting of OH, —$(C_1$-$C_6)$alkyl and hydroxy$(C_1$-$C_6)$alkyl-;
$R^{2a}$ is selected from the group consisting of:
a) -(6- to 14-membered)aryl or -(3- to 12-membered)heterocycle, each of which is optionally substituted with one, two, or three independently selected R$^{30}$ groups; and
b) —Z-G-R$^{10}$;
or $R^{2a}$ and $R^{2b}$ together form =O;
$R^3$ is selected from the group consisting of:
a) (6- to 14-membered)aryl or -(3- to 12-membered)heterocycle, each of which is optionally substituted with one, two, or three independently selected R$^{30}$ groups; and
b) —Z-G-R$^{10}$;
wherein each Z is independently absent or —(CH$_2$)$_m$—, optionally substituted with one or two —$(C_1$-$C_6)$alkyl;
each G is independently selected from the group consisting of:
a) a bond, —$(C_1$-$C_6)$alkylene, and —$(C_2$-$C_6)$alkenylene;
b) O, —O—C(=O)—, —C(=O), and =CH;
c) NR$^8$, =N—O, and =N—NH; and
d) S, SO, and SO$_2$;
Each R$^{10}$ is independently selected from the group consisting of:
a) hydrogen, —$(C_1$-$C_{10})$alkyl, —$(C_2$-$C_{12})$alkenyl, —CH(=O), —C(=O)—$(C_1$-$C_6)$alkyl, —C(=O)—$(C_2$-$C_6)$alkenyl, —C(=O)-(6- to 14-membered)aryl, —C(=O)—C$(C_1$-$C_6)$alkyl-(6- to 14-membered)aryl, —$(C_2$-$C_{12})$alkynyl, —$(C_1$-$C_{10})$alkoxy, —$(OCH_2 CH_2)_s$—O$(C_1$-$C_6)$alkyl, —$(CH_2CH_2O)_s$—$(C_1$-$C_6)$alkyl, —$(C_3$-$C_{12})$cycloalkyl, (($C_3$-$C_{12})$cycloalkyl)-$(C_1$-$C_6)$alkyl-, —$(C_4$-$C_{12})$cycloalkenyl, (($C_4$-$C_{12})$cycloalkenyl-$(C_1$-$C_6)$alkyl-, —$(C_6$-$C_{14})$bicycloalkyl, (($C_6$-$C_{14})$bicycloalkyl)-$(C_1$-$C_6)$alkyl-, —$(C_8$-$C_{20})$tricycloalkyl, (($C_8$-$C_{20})$tricycloalkyl)-$(C_1$-$C_6)$alkyl-, —$(C_7$-$C_{14})$bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(6- to 14-membered)aryl, ((6- to 14-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered) bicyclic aryl, -(7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-, each of which is optionally substituted with one, two, or three R$^{40}$ groups; and b) —NH$_2$, —NH(C$_1$-C$_6$)alkyl, CN, —NR$^5$R$^6$, —(C$_1$-C$_6$)alkyl-NR$^5$R$^6$, —CONR$^5$R$^6$, —(C$_1$-C$_6$)alkyl-CONR$^5$R$^6$, —COOR$^7$, —(C$_1$-C$_6$)alkyl-COOR$^7$, —(C$_1$-C$_6$)alkoxy-COOR$^7$, —C(=O)—(CH$_2$)$_n$—COOR$^7$, and —CO—(CH$_2$)$_n$—CONR$^5$R$^6$ each of which is optionally substituted with one, two, of three R$^{41}$ groups;

each R$^{40}$ is independently selected from the group consisting of OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, phenyl, benzyl, —NH$_2$, —NH(C$_1$-C$_6$)alkyl, —(C$_1$-C$_6$)alkyl-NH(C$_1$-C$_6$)alkyl-R$^{14}$, —CN, —SH, —OR$^{11}$, —CONR$^5$R$^6$, —(C$_1$-C$_6$alkyl)-CONR$^5$R$^6$, —COOR$^7$, —(C$_1$-C$_6$)alkyl-COOR$^7$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, (C$_1$-C$_6$)alkyl)sulfonyl, ((C$_1$-C$_6$)alkyl)sulfonyl(C$_1$-C$_6$)alkyl-, —NH—SO$_2$(C$_1$-C$_6$)alkyl, NH$_2$—SO$_2$(C$_1$-C$_6$)alkyl-, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)13 NH—(C$_1$-C$_6$)alkyl, —NH—C(=O)-(6- to 14-membered)aryl, —NH—C(=O)—(C$_1$-C$_6$)alkyl-(6- to 14-membered)aryl, —NH—(C$_1$-C$_6$)alkyl-COOR$^7$, —NH—C(=O)—(C$_1$-C$_6$)alkyl-COOR$^7$, —NH—C(=O)—CH(NH$_2$)—(C$_1$-C$_6$)alkyl-COOR$^7$, —(C$_3$-C$_{12}$)cycloalkyl, ((C$_3$-C$_{12}$)cycloalkyl)-(C$_1$-C$_6$)alkyl-, -(6- to 14-membered)aryl, -(6- to 14-membered) aryloxy, —(C$_1$-C$_6$)alkoxy-CONR$^5$R$^6$, —NH—(C$_1$-C$_6$) alkyl-CONR$^5$R$^6$, —C(=O)NH—(C$_1$-C$_6$)alkyl-COOR$^7$, ((6- to 14-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, (3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

each R$^{41}$ is independently selected from the group consisting of —OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, —(C$_1$-C$_6$)alkyl-NH(C$_1$-C$_6$)alkyl-R$^{14}$, —CONR$^{5a}$R$^{6a}$, —(C$_1$-C$_6$alkyl-CONR$^{5a}$R$^{6a}$ $^a$, —(C$_1$-C$_6$)alkyl-COOR$^7$, —(C$_1$-C$_6$)alkoxy-COOR$^7$, —(CH$_2$CH$_2$O)$_s$—(C$_1$-C$_6$)alkyl, (C$_1$C$_6$)alkyl)sulfonyl, ((C$_1$-C$_6$)alkyl)sulfonyl(C$_1$-C$_6$)alkyl-, —C(=NH)NH$_2$, phenyl, benzyl, —(C$_3$-C$_{12}$)cycloalkyl, ((C$_3$-C$_{12}$)cycloalkyl)-(C$_1$-C$_6$)alkyl-, -(6- to 14-membered)aryl, -(6- to 14-membered)aryloxy, ((6- to 14-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

provided that:
a) when R$^{2a}$ is hydrogen or OH, then R$^{2b}$ and R$^3$ are not H, —(C$_1$-C$_{52}$)alkyl, —(C$_2$-C$_{54}$)alkenyl, or —(C$_2$-C$_{54}$)alkynyl, each of which is unsubstituted; and
when R$^{2b}$ forms hydrogen, then R$^{2a}$ is not (C$_1$-C$_6$)alkyl; or
b) when R$^{2b}$ is Z-G-R$^{10}$, and G of R$^{2b}$ is =N—O, =N—NH, or =CH, and Z of R$^{2b}$ is absent, then R$^{2a}$ is absent; or
c) when R$^3$ is Z-G-R$^{10}$, and G of R$^3$ is =N—O, =N—NH, or =CH, then 2 of R$^3$ cannot be absent; or
d) when R$^{2a}$ is hydrogen or unsubstituted (C$_1$-C$_3$)alkyl, then R$^3$ is not unsubstituted (C$_1$-C$_6$)alkyl, —(C$_3$-C$_7$)alkenyl or —(C$_2$-C$_{54}$)alkynyl; or
e) when R$^4$ is methoxy, R$^1$ is methyl and R$^3$ is methyl, then R$^{2a}$ and R$^{2b}$ cannot together form =O; or
f) when R$^4$ is hydrogen, R$^1$ is methyl and R$^3$ is methyl, then
 (i) R$^{2a}$ and R$^{2b}$ cannot together form =O or =N—OH, or
 (ii) G is not NR$^8$; or
g) when R$^3$ is selected as unsubstituted (C$_1$-C$_6$)alkyl, R$^{2a}$ is (C$_1$-C$_6$)alkyl or hydroxy(C$_1$-C$_6$)alkyl, and R$^{2b}$ forms hydrogen, (C$_1$-C$_{52}$)alkyl, hydroxyl, amino or alkoxy, then R$^4$ is not —COOH, CH$_2$OH, CONH$_2$; and
h) when R$^3$ is methyl or ethyl, R$^4$ is OH, R$^1$ is (C$_1$-C$_3$)alkyl, which is optionally substituted with cyclopropyl or phenyl or alkenyl, and
 (i) R$^{2a}$ is hydrogen, then R$^{2b}$ is not (C$_1$-C$_3$)alkyl, or
 (ii) R$^{2a}$ is (C$_1$-C$_3$)alkyl, then R$^{2b}$ does not form hydrogen, (CH$_2$)$_2$—C(=O)—(CH$_2$)$_2$-cyclopentyl or CH$_3$;

R$^4$ is selected from the group consisting of:
a) —H, —OH, halo, —C(halo)$_3$, —CH(halo)$_2$, —CH$_2$(halo), —COOH, or —CONH$_2$; and
b) —(C$_1$-C$_6$)alkyl, —(C$_2$-C$_6$)alkenyl, —(C$_2$-C$_6$)alkynyl, —(CH$_2$)$_n$—O—(CH$_2$)$_n$—CH$_3$, and —(C$_1$-C$_6$)alkoxy, each of which is optionally substituted with 1, 2, or 3 independently selected R$^9$ groups;

R$^5$ and R$^6$ are each independently selected from the group consisting of:
a) hydrogen, —OH, halo, —C(halo)$_3$, —CH(halo)$_2$, and —CH$_2$(halo);
b) —(C$_1$-C$_6$)alkyl, —(C$_2$-C$_6$)alkenyl, —(C$_2$-C$_6$)alkynyl, —(CH$_2$)$_n$—O—(CH$_2$)$_n$—CH$_3$, and —(C$_1$-C$_6$)alkoxy, each of which is optionally substituted with 1, 2, or 3 substituents independently selected from —OH, halo, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —CHO, —COOH, —C(halo)$_3$, —CH(halo)$_2$, —CH$_2$(halo), —(CH$_2$)$_n$—O—(CH$_2$)$_n$—CH$_3$, phenyl and —CONR$^{5a}$R$^{6a}$;
c) —(C$_3$-C$_8$)cycloalkyl, ((C$_3$-C$_8$)cycloalkyl)-(C$_1$-C$_6$)alkyl, —COOR$^7$, —(C$_1$-C$_6$)alkyl-COOR$^7$, —CONH$_2$, and (C$_1$-C$_6$)alkyl-CONH—;
d) -(6- to 14-membered)aryl optionally substituted with 1, 2, or 3 independently selected R$^{30}$ groups; or
e) R$^5$ and R$^6$ together with the nitrogen atom to which they are attached form a (4- to 8-membered)heterocycle optionally substituted with 1, 2, or 3 independently selected R$^{30}$ groups;

R$^{5a}$ and R$^{6a}$ are each independently selected from the group consisting of:
a) hydrogen, —OH, halo, —C(halo)$_3$, —CH(halo)$_2$, and —CH$_2$(halo);
b) —(C$_1$-C$_6$)alkyl, —(C$_2$-C$_6$)alkenyl, —(C$_2$-C$_6$)alkynyl, —(CH$_2$)$_n$—O—(CH$_2$)$_n$—CH$_3$, and —(C$_1$-C$_6$)alkoxy, each of which is optionally substituted with 1, 2, or 3 substituents independently selected from —OH, halo, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —CHO, —COOH, —C(halo)$_3$, —CH(halo)$_2$, CH$_2$(halo), —(CH$_2$)$_n$—O—(CH$_2$)$_n$—CH, and phenyl;

c) —($C_3$-$C_8$)cycloalkyl, (($C_3$-$C_8$)cycloalkyl)-($C_1$-$C_6$)alkyl-, —COOR$^7$, —($C_1$-$C_6$)alkyl-COOR$^7$, —CONH$_2$, and ($C_1$-$C_6$)alkyl-CONH—;
d) -(6- to 14-membered)aryl optionally substituted with 1, 2, or 3 independently selected R$^{30}$ groups; or
e) R$^{5a}$ and R$^{6a}$ together with the nitrogen atom to which they are attached form a (4- to 8-membered)heterocycle optionally substituted with 1, 2, or 3 independently selected R$^{30}$ groups;

each R$^7$ is independently selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

each R$^8$ is independently selected from the group consisting of H, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, (($C_3$-$C_{12}$)cycloalkenyl)-($C_1$-$C_6$)alkyl-, —C(=O)($C_1$-$C_6$)alkyl and SO$_2$($C_1$-$C_6$)alkyl;

each R$^9$ is independently selected from the group consisting of —OH, halo, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —CHO, —COOH, —C(halo)$_3$, —CH(halo)$_2$, —CH$_2$(halo), —(CH$_2$)$_n$—O—(CH$_2$)$_n$—CH$_3$, phenyl, and —CONR$^{5a}$R$^{6a}$;

each R$^{11}$ is independently selected from the group consisting of —C(halo)$_3$, —CH(halo)$_2$, —CH$_2$(halo), —($C_1$-$C_6$)alkyl, —($C_2$-$C_6$)alkenyl, —($C_2$-$C_6$)alkynyl, —(CH$_2$)$_n$—O—(CH$_2$)$_n$—CH$_3$, -(6- to 14-membered)aryl, ((6- to 14-membered)aryl)-($C_1$-$C_6$)alkyl-, -(5- to 12-membered)heteroaryl, and ((5- to 12-membered)heteroaryl)-($C_1$-$C_6$)alkyl-, each of which is optionally substituted with 1, 2, or 3 independently selected R$^9$ groups;

each R$^{14}$ is independently selected from the group consisting of —COOR$^7$, —($C_1$-$C_6$)alkyl-COOR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONR$^{5a}$R$^{6a}$, and —($C_1$-$C_6$)alkyl-CONR$^{5a}$R$^{6a}$;

each R$^{30}$ is independently selected front —COOR$^7$, —CONR$^{5a}$R$^{6a}$, —($C_1$-$C_6$)alkyl, CN, -(3- to 12-membered)heteroaryl, ((3- to 12-membered)heteroaryl)-($C_1$-$C_6$)alkyl, NH$_2$, halo, and ((6- to 14-membered)aryl)-($C_1$-$C_6$)alkoxy-;

m is an integer 1, 2, 3, 4, 5, or 6;
n is an integer 0, 1, 2, 3, 4, 5, or 6;
s in an integer 1, 2, 3, 4, 5, or 6;
and the pharmaceutically acceptable salt or solvate thereof.

In one embodiment, the present invention provides novel compounds of Formula IA':

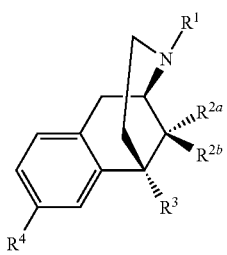

IA' wherein R$^1$, R$^{2a}$, R$^{2b}$, R$^3$ and R$^4$ are as defined above for Formula I', and the pharmaceutically acceptable salts and solvates thereof.

In another embodiment, the present invention provides novel compounds of Formula IB':

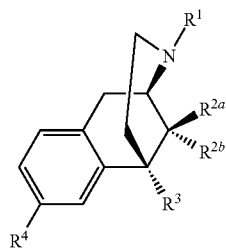

IB' wherein R$^1$, R$^{2a}$, R$^{2b}$, R$^3$ and R$^4$ are as defined above Formula I', and the pharmaceutically acceptable salts and solvates thereof.

In another embodiment, the present Invention provides novel compounds of Formula IC':

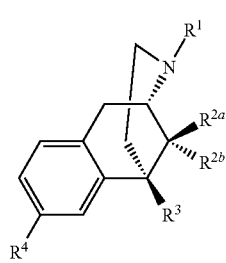

IC' wherein R$^1$, R$^{2a}$, R$^{2b}$, R$^3$ and R$^4$ are as defined above for Formula I', and the pharmaceutically acceptable salts and solvates thereof.

In another embodiment, the present invention provides novel compounds of Formula ID':

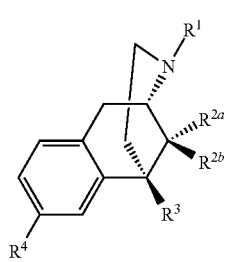

ID' wherein R$^1$, R$^{2a}$, R$^{2b}$, R$^3$ and R$^4$ are as defined above for Formula I', and the pharmaceutically acceptable salts and solvates thereof.

It is an object of certain embodiments of the present invention to provide new compounds that are therapeutically effective at treating a Condition (as defined below), while having reduced side effects (such as opioid-induced constipation) compared to compounds currently available.

Certain Compounds of the invention have agonist activity at the μ, δ and/or κ receptors which is greater than currently available compounds, e.g., morphine.

Certain Compounds of the Invention have both: (i) antagonist activity at the ORL-1 receptor; and (ii) agonist activity at one or more of the μ, δ and/or κ receptors. Certain Compounds of the Invention have both; (i) antagonist activity at the ORL-1 receptor; and (ii) agonist activity at the µ receptor. Certain compounds of the invention will have both: (i) antagonist activity at the µ receptor; and (ii) agonist activity at the κ receptor. Certain compounds of the invention will have: (i) antagonist activity at the ORL-1 receptor; (ii) antagonist activity at the µ receptor; and (iii) agonist activity at the κ receptor. Certain compounds of the invention will have: (i) antagonist activity at the µ receptor; (ii) agonist activity at the κ receptor; and (iii) antagonist activity at the δ receptor.

Compounds of the Invention may be useful as analgesics to treat, ameliorate, or prevent pain; or as agents to treat, ameliorate, or prevent addictive disorders; or as agents to treat, ameliorate, or prevent withdrawal from alcohol and/or drugs of addiction; or as agents to treat, ameliorate, or prevent pruritic conditions; or as agents to treat or prevent constipation; or as agents to treat or prevent diarrhea (each of pain, alcohol withdrawal, drug withdrawal, addictive disorders, pruritis, constipation, and diarrhea being a "Condition").

In a further aspect, the present invention provides methods for treating a Condition, comprising administering to a subject in need thereof a therapeutically effective amount of a Compound of the Invention. In certain embodiments, the Condition is pain (chronic or acute pain). The Compounds of the Invention are particularly useful for treating chronic pain.

Compounds of the Invention can be used to treat, ameliorate, or prevent acute or chronic pain. Examples of pain that can be treated, ameliorated, or prevented using a Compound of the Invention include, but are not limited to, cancer pain, neuropathic pain, labor pain, myocardial infarction pain, pancreatic pain, colic pain, post-operative pain, headache pain, migraine pain, muscle pain, arthritic pain, and pain associated with a periodontal disease, including gingivitis and periodontitis.

Compounds of the Invention can also be used to treat, ameliorate, or prevent pain associated with inflammation or with an inflammatory disease in an animal. Such pain can arise where there is an inflammation of the body tissue which can be a local inflammatory response or a systemic inflammation. For example, a Compound of the Invention can be used to treat, ameliorate, or prevent pain associated with inflammatory diseases including, but not limited to, organ transplant rejection; reoxygenation injury resulting from organ transplantation (see Grupp et al., *J. Mol. Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer. Compounds of the Invention can also be used to treat, ameliorate, or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

Compounds of the invention can also be used to treat, ameliorate, or prevent pain associated with, nerve injury (i.e., neuropathic pain). Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial, burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

Compounds of the Invention can be used to treat, ameliorate, or prevent pain associated with migraine including, but not limited to, migraine without aura ("common migraine"), migraine with aura ("classic migraine"), migraine without headache, basilar migraine, familial hemiplegic migraine, migrainous infarction, and migraine with prolonged aura.

Another object of the invention is to provide benzomorphan analog compounds useful for treating, ameliorating, or preventing constipation, preferably µ opioid receptor-induced, constipation. Such compounds can be used by administering an effective amount of a Compound of the Invention to a patient in need of such treatment or prevention. In one embodiment, the Compound of the Invention is a µ antagonist that is substantially restricted to the GI tract. In another embodiment, the Compound of the Invention is both a μ antagonist and a κ agonist, and is substantially restricted to the GI tract. In another embodiment, the method comprises co-administering to a patient both an effective amount of a Compound of the Invention that is a μ antagonist and is substantially restricted to the GI tract, and an analgesically effective amount of a μ agonist. In another embodiment, the method comprises co-administration to a patient of both an effective amount of a Compound of the Invention that is both a μ antagonist and a κ agonist, and which is substantially restricted to the GI tract, and an analgesically effective amount of a μ agonist. Compounds of the Invention that have μ antagonist activity and are substantially restricted to the GI tract will significantly reduce or prevent constipation that would otherwise occur in a patient as a result of treatment with a μ agonist. In one embodiment, the reduction or prevention of constipation is obtained without substantially reducing the desired analgesic effect of the μ agonist. Compounds of the Invention that also exhibit κ agonist activity should additionally stimulate GI motility via a non-μ receptor-mediated mechanism.

In certain non-limiting embodiments, the Compound of the Invention exhibits a substantially linear dose response curve, such that the bell-shaped dose response curve observed for most opioid analgesics (i.e. low and high doses do not produce significant analgesia, whereas mid-range doses produce analgesia) is not observed for the Compound of the Invention. It is expected, therefore, that it will be easier to titrate to an effective dose of the Compound of the Invention in a patient than it is for conventional opioid analgesics. It is further expected that the Compound of the Invention will produce effective analgesia and/or anti-hyperalgesia in a patient who has become tolerant to conventional opioids, and for whom a conventional opioid is no longer an effective treatment. It is further expected that a Compound of the Invention will produce effective analgesia and/or anti-hyperalgesia at doses that do not induce side effects such as respiratory depression in patients for whom a dose of a conventional opioid that is high enough to be an effective treatment also induces significant side effects such as respiratory depression.

In a further aspect, the present invention provides methods for preventing a Condition, comprising administering to a subject in need thereof a Condition-preventing effective amount of a Compound of the Invention.

In a further aspect, the present invention provides pharmaceutical compositions comprising a therapeutically effective amount of a Compound of the Invention admixed with a pharmaceutically acceptable carrier or excipient. Such compositions are useful for treating, ameliorating, or preventing a Condition in a subject. The pharmaceutical compositions of the present invention may be formulated as immediate release formulations, or as controlled or sustained release formulations. Pharmaceutical compositions of the present invention may be formulated for administration by any of a number of different routes known in the art, including but not limited to, oral, intradermal, intramuscular, intraperitoneal, parenteral, intravenous, subcutaneous, intranasal, epidural, sublingual, intracerebral, intravaginal, transdermal, transmucosal, rectal, by inhalation, or topical (particularly to the ears, nose, eyes, or skin).

In a further aspect, the present invention provides methods for preparing a composition, comprising the step of admixing a Compound of the Invention and a pharmaceutically acceptable carrier or excipient to form a pharmaceutical composition.

In a further aspect, the invention still further relates to a kit comprising a sterile container containing an effective amount of a Compound of the Invention, and instructions for therapeutic use.

DETAILED DESCRIPTION OF THE INVENTION

The Compounds of the Invention are novel benzomorphan analogs. They are useful for treating or preventing one or more Conditions, such as pain or constipation. Compounds of the Invention may provide a reduced liability for developing analgesic tolerance and physical dependence.

The Compounds of the Invention are useful for modulating a pharmacodynamic response from one or more opioid receptors (μ, δ, κ or ORL-1) either centrally or peripherally, or both. The pharmacodynamic response may be attributed to the compound stimulating (agonizing) or inhibiting (antagonizing) the one or more receptors. Certain Compounds of the Invention may inhibit (or antagonize) the ORL-1 receptor, while also stimulating (or agonizing) one or more other receptors (e.g. as a μ, δ and/or κ agonist). Compounds of the Invention having agonist activity may be either full or partial agonists.

In certain embodiments, Compounds of the Invention can be used in combination with at least one other therapeutic agent. The other therapeutic agent can be, but is not limited to, a μ-opioid agonist, a non-opioid analgesic, a non-steroidal anti-inflammatory agent, a Cox-II inhibitor, an anti-emetic, a β-adrenergic blocker, an anticonvulsant, an antidepressant, a $Ca^{2+}$-channel blocker, an anticancer agent, or a mixture thereof.

Various objects and advantages of the present invention will become apparent from the following detailed description.

In a particular aspect, the present invention provides novel compounds of Formula I:

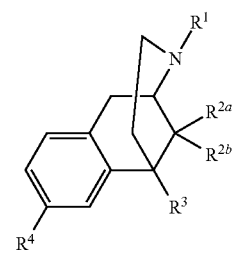

I wherein $R^1$, $R^{2a}$, $R^{2b}$, $R^3$ and $R^4$ are as defined above, and the pharmaceutically acceptable salts and solvates thereof.

In other embodiments, the present invention provides novel compounds of Formula IA:

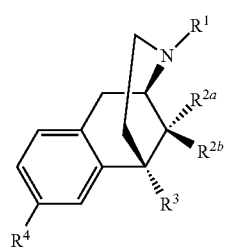

IA wherein $R^1$, $R^{2a}$, $R^{2b}$, $R^3$ and $R^4$ are as defined above for Formula I, and the pharmaceutically acceptable salts, and solvates thereof.

In other embodiments, the present invention provides novel compounds of Formula IB:

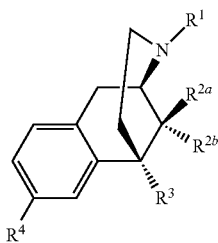

wherein $R^1$, $R^{2a}$, $R^{2b}$, $R^3$ and $R^4$ are as defined above for Formula I, and the pharmaceutically acceptable salts, and solvates thereof.

In other embodiments, the present invention provides novel compounds of Formula IC:

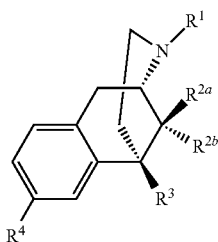

wherein $R^1$, $R^{2a}$, $R^{2b}$, $R^3$ and $R^4$ are as defined above for Formula I, and the pharmaceutically acceptable salts, and solvates thereof.

In other embodiments, the present invention provides novel compounds of Formula ID:

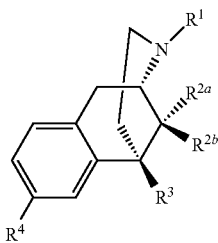

wherein $R^1$, $R^{2a}$, $R^{2b}$, $R^3$ and $R^4$ areas defined above for Formula I, and the pharmaceutically acceptable salts, and solvates thereof.

In another aspect, the present invention provides novel compounds of Formula I':

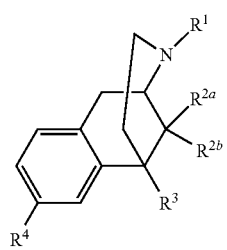

wherein $R^1$ is selected from the group consisting of —$(C_1$-$C_{10})$alkyl, —$(C_2$-$C_{12})$alkenyl, —$(C_2$-$C_{12})$alkynyl, —$(C_3$-$C_{12})$cycloalkyl, $(C_3$-$C_{12})$cycloalkyl-$(C_1$-$C_6)$alkyl-, —$(C_3$-$C_{12})$cycloalkenyl, $(C_3$-$C_{12})$cycloalkenyl-$(C_1$-$C_6)$alkyl-, -(6- to 14-membered)aryl, ((6- to 14-membered)aryl)-$(C_1$-$C_6)$alkyl-, diphenyl$(C_1$-$C_6)$alkyl-, —$(OCH_2CH_2)_s$—O—$(C_1$-$C_6)$alkyl, —$(CH_2CH_2O)_s$—$(C_1$-$C_6)$alkyl, —$(C_1$-$C_{10})$alkoxy, —$C(halo)_3$, —$CH(halo)_2$, —$CH_2(halo)$, —$C(=O)R^5$, —$C(=O)$—O—$(C_1$-$C_{10})$alkyl, —$C(=O)$—$N(R^6)_2$ and —$(CH_2)_n$—$N(R^6)_2$, each of which is optionally substituted by 1, 2 or 3 independently selected $R^9$ groups;

$R^{2a}$ is hydrogen, or selected from the group consisting of OH, —$(C_1$-$C_6)$alkyl and hydroxy$(C_1$-$C_6)$alkyl-;

$R^{2a}$ is selected from the group consisting of:
a) -(6- to 14-membered)aryl or -(3- to 12-membered)heterocycle, each of which is optionally substituted with one, two, or three independently selected $R^{30}$ groups; and
b) —Z-G-$R^{10}$);

or $R^{2a}$ and $R^{2b}$ together form =O;

$R^3$ is selected from the group consisting of:
a) -(6- to 14-membered)aryl or -(3- to 12-membered)heterocycle, each of which is optionally substituted with one, two, or three independently selected $R^{30}$ groups; and
b) —Z-G-$R^{10}$;

wherein each Z is independently absent or —$(CH_2)_m$—, optionally substituted with one or two —$(C_1$-$C_6)$alkyl;

each G is independently selected from the group consisting of:
a) a bond, —$(C_1$-$C_6)$alkylene, and —$(C_2$-$C_6)$alkenylene;
b) O, —O—$C(=O)$—, —$C(=O)$, and =CH;
c) $NR^8$, =N—O, and =N—NH; and
d) S, SO, and $SO_2$;

Each $R^{10}$ is independently selected from the group consisting of:
a) hydrogen, —$(C_1$-$C_{10})$alkyl, —$(C_2$-$C_{12})$alkenyl, —CH(=O), —$C(=O)$—$(C_1$-$C_6)$alkyl, —$C(=O)$—$(C_2$-$C_6)$alkenyl, —$C(=O)$-(6- to 14-membered)aryl, —$C(=O)$—$(C_1$-$C_6)$alkyl-(6- to 14-membered)aryl, —$(C_2$-$C_{12})$alkynyl, —$(C_1$-$C_{10})$alkoxy, —$(OCH_2CH_2)_s$—$O(C_1$-$C_6)$alkyl, —$(CH_2CH_2O)_s$—$(C_1$-$C_6)$alkyl, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, $((C_4$-$C_{12})$cycloalkenyl)-$(C_1$-$C_6)$alkyl-, —$(C_6$-$C_{14})$bicycloalkyl, $((C_6$-$C_{14})$bicycloalkyl)-$(C_1$-$C_6)$alkyl-, —$(C_8$-$C_{20})$tricycloalkyl, $((C_8$-$C_{20})$tricycloalkyl)-$(C_1$-$C_6)$alkyl-, —$(C_7$-$C_{14})$bicycloalkenyl, $((C_7$-$C_{14})$bicycloalkenyl)-$(C_1$-$C_6)$alkyl-, —$(C_8$-$C_{20})$tricycloalkenyl, $((C_8$-$C_{20})$tricycloalkenyl)-$(C_1$-$C_6)$alkyl-, -(6- to 14-membered)aryl, ((6- to 14-membered)aryl)-$(C_1$-$C_6)$alkyl-, -(7- to 12)membered)bicyclic ring system, ((7- to 12-membered)bicyclic ring system)-$(C_1$-$C_6)$alkyl-, -(7- to 12-membered)bicyclic aryl, ((7- to 12-membered)bicyclic aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12membered)heterocycle)-$(C_1$-$C_6)$alkyl-, -(7- to 12-membered)bicycloheterocycle, and ((7- to 12-membered)bicycloheterocycle)-$(C_1$-$C_6)$alkyl-, each of which is optionally substituted with one, two, or three $R^{40}$ groups; and b) —$NH_2$, —$NH(C_1$-$C_6)$alkyl, CN, —$NR^5R^6$, —$(C_1$-$C_6)$alkyl-$NR^5R^6$, —$CONR^5R^6$, —$(C_1$-$C_6)$alkyl-$CONR^5R^6$, —$COOR^7$, —$(C_1$-$C_6)$alkyl-$COOR^7$, —$(C_1$-$C_6)$alkoxy-$COOR^7$, —$C(=O)$ —$(CH_2)_n$—$COOR^7$, and —CO—(CH$_2$)$_n$—CONR$^5$R$^6$ each of which is optionally substituted with one, two, or three R$^{41}$ groups;

each R$^{40}$ is independently selected from the group consisting of —OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, phenyl, benzyl, —NH$_2$, —NH(C$_1$-C$_6$)alkyl, —(C$_1$-C$_6$)alkyl-NH(C$_1$-C$_6$)alkyl-R$^{14}$, —CN, —SH, —OR$^{11}$, —CONR$^5$R$^6$, —(C$_1$-C$_6$alkyl)-CONR$^5$R$^6$, —COOR$^7$, —(C$_1$-C$_6$)alkyl-COOR$^7$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, (C$_1$-C$_6$)alkyl)sulfonyl, ((C$_1$-C$_6$)alkyl)sulfonyl(C$_1$-C$_6$)alkyl-, —NH—SO$_2$(C$_1$-C$_6$)alkyl, NH$_2$-SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(6- to 14-membered)aryl, —NH—C(=O)—(C$_1$-C$_6$)alkyl-(6- to 14- membered)aryl, —NH—(C$_1$-C$_6$)alkyl-COOR$^7$, —NH—C(=O)—(C$_1$-C$_6$)alkyl-COOR$^7$, —NH—C(=O)—CH(NH$_2$)—(C$_1$-C$_6$)alkyl-COOR$^7$, —(C$_3$-C$_{12}$)cycloalkyl, ((C$_3$-C$_{12}$cycloalkyl)-(C$_1$-C$_6$)alkyl-, -(6- to 14-membered)aryl, -(6- to 14-membered) aryloxy, —(C$_1$-C$_6$)alkoxy-CONR$^5$R$^6$, —NH—(C$_1$-C$_6$) alkyl-CONR$^5$R$^6$, —C(=O)NH—(C$_1$-C$_6$)alkyl-COOR$^7$, ((6- to 14-membered)aryl)-(C$_1$-C$_6$)alkyl-, -(5- to 12-membered)heteroaryl, ((5-to 12-membered)heteroaryl-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

each R$^{41}$ is independently selected from the group consisting of —OH, (=O), halo, —C(halo)$_3$, —CH(halo)$_2$, —CH$_2$(halo), —(C$_1$-C$_6$)alkyl-, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, —(C$_1$-C$_6$)alkyl-NH(C$_1$-C$_6$)alkyl-R$^{14}$, —CONR$^{5a}$R$^{6a}$, —(C$_1$-C$_6$alkyl-CONR$^{5a}$R$^{6a}$, —(C$_1$-C$_6$)alkyl-COOR$^7$, —(C$_1$-C$_6$)alkoxy-COOR$^7$, —(CH$_2$CH$_2$O)$_s$—(C$_1$-C$_6$)alkyl, (C$_1$-C$_6$)alkyl)sulfonyl, ((C$_1$-C$_6$)alkyl)sulfonyl(C$_1$-C$_6$)alkyl-, —C(=NH)NH$_2$, phenyl, benzyl, —(C$_3$-C$_{12}$)cycloalkyl, ((C$_3$-C$_{12}$)cycloalkyl)-(C$_1$-C$_6$)alkyl-, -(6- to 14-membered)aryl, -(6- to 14-membered)aryloxy, ((6- to 14-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

provided that:
a) when R$^{2a}$ is hydrogen or OH, then R$^{2b}$ and R$^3$ are not H, —(C$_1$-C$_{52}$)alkyl, —(C$_2$-C$_{54}$)alkenyl, or —(C$_2$-C$_{54}$)alkynyl, each of which is unsubstituted; and when R$^{2b}$ forms hydrogen, then R$^{2a}$ is not (C$_1$-C$_6$)alkyl; or
b) when R$^{2b}$ is Z-G-R$^{10}$, and G of R$^{2a}$ is =N—O, =N—NH, or =CH, and Z of R$^{2b}$ is absent, then R$^{2a}$ is absent; or
c) when R$^3$ is Z-G-R$^{10}$, and G of R$^3$ is =N—O, =N—NH, or =CH, then Z of R$^3$ cannot be absent; or
d) when R$^{2a}$ is hydrogen or unsubstituted (C$_1$-C$_3$)alkyl, then R$^3$ is not unsubstituted (C$_1$-C$_6$)alkyl, —(C$_3$-C$_7$)alkenyl or —(C$_2$-C$_{54}$)alkynyl; or
e) when R$^4$ is methoxy, R$^1$ is methyl and R$^3$ is methyl, then R$^{2a}$ and R$^{2b}$ cannot together form =O; or
f) when R$^4$ is hydrogen, R$^1$ is methyl and R$^3$ is methyl, then
  (i) R$^{2a}$ and R$^{2b}$ cannot together form =O or =N—OH, or
  (ii) G is not NR$^8$; or
g) when R$^3$ is selected as unsubstituted (C$_1$-C$_6$)alkyl, R$^{2a}$ is (C$_1$-C$_6$)alkyl or hydroxy(C$_1$-C$_6$)alkyl, and R$^{2b}$ forms hydrogen, (C$_1$-C$_{52}$)alkyl, hydroxyl, amino or alkoxy, then R$^4$ is not —COOH, CH$_2$OH, CONH$_2$; and
h) when R$^3$ is methyl or ethyl, R$^4$ is OH, R$^1$ is (C$_1$-C$_3$)alkyl, which is optionally substituted with cyclopropyl or phenyl or alkenyl, and
  (i) R$^{2a}$ is hydrogen, then R$^{2b}$ is not (C$_1$-C$_3$)alkyl, or
  (ii) R$^{2a}$ is (C$_1$-C$_3$)alkyl, then R$^{2b}$ does not form hydrogen, (CH$_2$)$_2$—C(=O)—(CH$_2$)$_2$-cyclopentyl or CH$_3$;

R$^4$ is selected from the group consisting of:
a) —H, —OH, halo, —C(halo)$_3$, —CH(halo)$_2$, —CH$_2$(halo), —COOH, or —CONH$_2$; and
b) —(C$_1$-C$_6$)alkyl, —(C$_2$-C$_6$)alkenyl, —(C$_2$-C$_6$)alkynyl, —(CH$_2$)$_n$—O—(CH$_2$)$_n$—CH$_3$, and —(C$_1$-C$_6$)alkoxy, each of which is optionally substituted with 1, 2, or 3 independently selected R$^9$ groups;

R$^5$ and R$^6$ are each independently selected from the group consisting of:
a) hydrogen, —OH, halo, —C(halo)$_3$, —CH(halo)$_2$, and —CH$_2$(halo);
b) —(C$_1$-C$_6$)alkyl, —(C$_2$-C$_6$)alkenyl, —(C$_2$-C$_6$)alkynyl, —(CH$_2$)$_n$—O—(CH$_2$)$_n$—CH$_3$, and —(C$_1$-C$_6$)alkoxy, each of which is optionally substituted, with 1, 2, or 3 substituents independently selected from —OH, halo, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —CHO, —COOH, —C(halo)$_3$, —CH(halo)$_2$, —CH$_2$(halo), —(CH$_2$)$_n$—O—(CH$_2$)$_n$—CH$_3$, phenyl, and —CONR$^{5a}$R$^{6a}$;
c) —(C$_3$-C$_8$)cycloalkyl, ((C$_3$-C$_8$)cycloalkyl-(C$_1$-C$_6$)alkyl-, —COOR$^7$, —(C$_1$-C$_6$)alkyl-COOR$^7$, —CONH$_2$, and (C$_1$-C$_6$)alkyl-CONH—;
d) -(6- to 14-membered)aryl optionally substituted, with 1, 2, or 3 independently selected R$^{30}$ groups; or
e) R$^5$ and R$^6$ together with the nitrogen atom to which they are attached form a (4- to 8-membered)heterocycle optionally substituted with 1, 2, or 3 independently selected R$^{30}$ groups;

R$^{5a}$ and R$^{6a}$ are each independently selected from the group consisting of:
a) hydrogen, —OH, halo, —C(halo)$_3$, —CH(halo)$_2$, and —CH$_2$(halo);
b) —(C$_1$-C$_6$)alkyl; —(C$_2$-C$_6$)alkenyl, —(C$_2$-C$_6$)alkynyl, —(CH$_2$)$_n$—O—(CH$_2$)$_n$—CH$_3$, and —(C$_1$-C$_6$)alkoxy, each of which is optionally substituted with 1, 2 or 3 substituents independently selected from —OH, halo, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —CHO, —COOH, —C(halo)$_3$, —CH(halo)$_2$, CH$_2$(halo), —(CH$_2$)$_n$—O—(CH$_2$)$_n$—CH$_3$, and phenyl;
c) —(C$_3$-C$_8$)cycloalkyl, ((C$_3$-C$_8$)cycloalkyl)-(C$_1$-C$_6$)alkyl-, —COOR$^7$, —(C$_1$-C$_6$)alkyl-COOR$^7$, —CONH$_2$, and (C$_1$-C$_6$)alkyl-CONH—;
d) -(6- to 14-membered)aryl optionally substituted with 1, 2, or 3 independently selected R$^{30}$ groups; or
e) R$^{5a}$ and R$^{6a}$ together with the nitrogen atom to which they are attached form a (4- to 8-membered)heterocycle optionally substituted with 1, 2, or 3 independently selected R$^{30}$ groups;

each R$^7$ is independently selected from the group consisting of hydrogen, —(C$_1$-C$_6$)alkyl, —(C$_2$-C$_6$)alkenyl, —(C$_2$-C$_6$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, and ((C$_4$-C$_{12}$)cycloalkenyl)-(C$_1$-C$_6$)alkyl-;

each $R^8$ is independently selected from the group consisting of H, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, —($C_3$-$C_{12}$)cycloalkenyl)-($C_1$-$C_6$)alkyl-, —C(=O)($C_1$-$C_6$)alkyl and $SO_2$($C_1$-$C_6$)alkyl;

each $R^9$ is independently selected from the group consisting of —OH, halo, —($C_1$-$C_{10}$)alkyl, —($C_2$-$C_{12}$)alkenyl, —($C_2$-$C_2$)alkynyl, —($C_1$-$C_{10}$)alkoxy, —($C_3$-$C_{12}$)cycloalkyl, —CHO, —COOH, —C(halo)$_3$, —CH(halo)$_2$, —$CH_2$(halo), —$(CH_2)_n$—O—$(CH_2)_n$—$CH_3$, phenyl, and —$CONR^{5a}R^{6a}$;

each $R^{11}$ is independently selected from the group consisting of —C(halo)$_3$, —CH(halo)$_2$, —$CH_2$(halo), —($C_1$-$C_6$)alkyl, —($C_2$-$C_6$)alkenyl, —($C_2$-$C_6$)alkynyl, —$(CH_2)_n$—O—$(CH_2)_n$—$CH_3$, -(6-to 14-membered)aryl, ((6- to 14-membered)aryl)-($C_1$-$C_6$)alkyl-, -(5- to 12-membered)heteroaryl, and ((5- to 12-membered)heteroaryl)-($C_1$-$C_6$)alkyl-, each of which is optionally substituted with 1, 2, or 3 independently selected $R^9$ groups;

each $R^{14}$ is independently selected from the group consisting of —$COOR^7$, —($C_1$-$C_6$)alkyl-$COOR^7$, —C(=O)—($C_1$-$C_6$)alkyl-$COOR^7$, —($C_1$-$C_6$)alkyl-C(=O)—($C_1$-$C_6$)alkyl-$COOR^7$, —$CONR^{5a}R^{6a}$, and —($C_1$-$C_6$)alkyl-$CONR^{5a}R^{6a}$;

each $R^{30}$ is independently selected from —$COOR^7$, —$CONR^{5a}R^{6a}$, —($C_1$-$C_6$)alkyl, CN, -(3- to 12-membered)heteroaryl, ((3- to 12-membered)heteroaryl)-($C_1$-$C_6$)alkyl, —$NH_2$, halo, and ((6- to 14-membered)aryl)-($C_1$-$C_6$)alkoxy-;

m is an integer 1, 2, 3, 4, 5, or 6;
n is an integer 0, 1, 2, 3, 4, 5, or 6;
s in an integer 1, 2, 3, 4, 5, or 6;
and the pharmaceutically acceptable salt or solvate thereof.

In one embodiment, the present invention provides novel compounds of Formula IA';

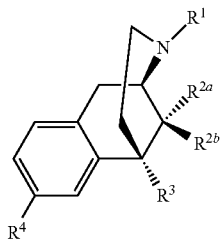

IA' wherein $R^1$, $R^{2a}$, $R^{2b}$, $R^3$ and $R^4$ are as defined above for Formula I', and the pharmaceutically acceptable salts and solvates thereof.

In another embodiment, the present invention provides novel compounds of Formula IB':

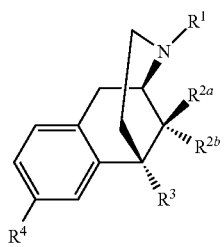

IB' wherein $R^1$, $R^{2a}$, $R^{2b}$, $R^3$ and $R^4$ are as defined above for Formula I', and the pharmaceutically acceptable salts and solvates thereof.

In another embodiment, the present invention provides novel compounds of Formula IC':

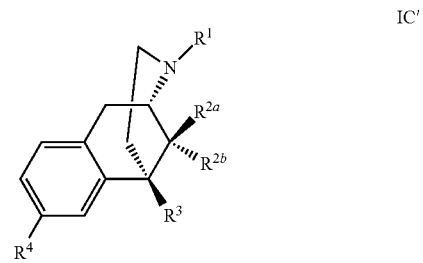

IC' wherein $R^1$, $R^{2a}$, $R^{2b}$, $R^3$ and $R^4$ are as defined above for Formula I', and the pharmaceutically acceptable salts and solvates thereof.

In another embodiment, the present invention provides novel compounds of Formula ID':

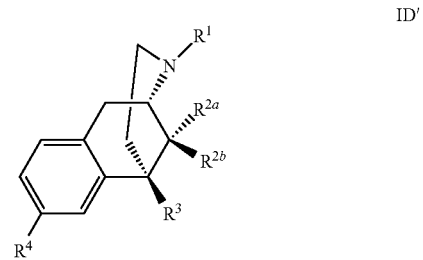

ID' wherein $R^1$, $R^{2a}$, $R^{2b}$, $R^3$ and $R^4$ are as defined above for Formula I', and the pharmaceutically acceptable salts and solvates thereof.

The following embodiments pertain to any one of Formulae I-ID, and I'-ID', and the pharmaceutically acceptable salts and solvates thereof.

In certain embodiments, $R^1$ is —($C_1$-$C_{10}$)alkyl.
In other embodiments, $R^1$ is methyl.
In other embodiments, $R^1$ is ethyl.
In certain embodiments, $R^1$ is —($C_3$-$C_{12}$)cycloalkyl.
In other embodiments, $R^1$ is (($C_3$-$C_{12}$)cycloalkyl)-($C_1$-$C_6$)alkyl-.
In other embodiments, $R^1$ is cyclopropylmethyl.
In certain embodiments, $R^4$ is OH.
In certain embodiments, $R^4$ is —($C_1$-$C_6$)alkyl.
In other embodiments, $R^4$ is methyl.
In other embodiments, $R^4$ is ethyl.
In certain embodiments, $R^4$ is —($C_1$-$C_6$)alkoxy.
In other embodiments, $R^4$ is methoxy.
In other embodiments, $R^4$ is ethoxy.
In certain embodiments, $R^4$ is halo.
In other embodiments, $R^4$ is F.
In certain embodiments, $R^4$ is —C(halo)$_3$.
in other embodiments, $R^4$ is —$CF_3$.
In other embodiments, $R^4$ is —$CCl_3$.
In certain embodiments, $R^4$ is —CH(halo)$_2$.
In other embodiments, $R^4$ is —$CHF_2$.
In certain embodiments, $R^4$ is $CONH_2$.
in certain embodiments, $R^4$ is COOH.
In certain embodiments, $R^{2a}$ is OH.
In certain embodiments $R^{2a}$ and $R^{2b}$ together form =O.

In certain embodiments, $R^{2b}$ is -(6- to 14-membered)aryl or -(3- to 12-membered)heterocycle, each of which is optionally substituted with one, two or three independently selected $R^{30}$ groups.

In certain embodiments, $R^3$ is -(6- to 14-membered)aryl or -(3- to 12-membered)heterocycle, each of which is optionally substituted with one, two or three independently selected $R^{30}$ groups.

In certain embodiments, $R^3$ is —Z-Q-$R^{10}$, wherein Z-G forms —$(CH_2)_s$ and $R^{10}$ is —$COOR^7$ or —$CONR^5R^6$, —$NH_2$, or $N(H)(C_1\text{-}C_6)$alkyl.

In certain embodiments, $R^3$ is —Z-G-$R^{10}$, and Z-G-$R^{10}$ forms —$(CH_2)_s$—OH.

In certain embodiments, $R^3$ is —Z-G-$R^{10}$, wherein Z-G-$R^{10}$ forms —$(CH_2)_3$—COOH, —$(CH_2)_3$—$CONH_2$, —$(CH_n)CONH_2$, or —$CH_2OH$.

In certain embodiments, $R^{2b}$ is —Z-G-$R^{10}$, provided that —Z-G-$R^{10}$ is other than hydrogen, —$(C_1\text{-}C_6)$alkyl, —$(C_2\text{-}C_6)$alkenyl, or —$(C_2\text{-}C_6)$-alkynyl.

In certain embodiments, $R^{2b}$ is —Z-G-$R^{10}$, wherein Z is absent.

In certain embodiments, $R^3$ is —Z-G-$R^{10}$, wherein Z is absent.

In certain embodiments, $R^{2b}$ and $R^3$ are each independently selected —Z-G-$R^{10}$, wherein Z is absent in both cases.

In certain embodiments, $R^{2b}$ is —Z-G-$R^{10}$, wherein Z is —$CH_2$—.

In certain embodiments, $R^{2b}$ is —Z-G-$R^{10}$, wherein G is $NR^8$.

In certain embodiments, $R^{2b}$ is —Z-G-$R^{10}$, wherein G is $NR^8$, wherein $R^8$ is hydrogen.

In other embodiments, $R^{2b}$ is —Z-G-$R^{10}$, wherein G is $NR^8$, wherein $R^8$ is —$(C_1\text{-}C_6)$alkyl.

In other embodiments, $R^{2b}$ is —Z-G-$R^{10}$, wherein G is $NR^8$, wherein $R^8$ is methyl or ethyl.

In certain embodiments, $R^{2b}$ is —Z-G-$R^{10}$, wherein G is a bond.

In certain embodiments, $R^{2b}$ is —Z-G-$R^{10}$, wherein G is O.

In certain embodiments, $R^{2b}$ is —Z-G-$R^{10}$, wherein G is —O—C(=O)—.

In certain embodiments, $R^{2b}$ is —Z-G-$R^{10}$, wherein G is —CH(=O).

In certain embodiments, $R^{2b}$ is —Z-G-$R^{10}$, wherein G is =CH.

In certain embodiments, $R^{2b}$ is —Z-G-$R^{10}$, wherein G is =N—O.

In certain embodiments, $R^{2b}$ is —Z-G-$R^{10}$, wherein G is S.

In certain embodiments, $R^{2b}$ is —Z-G-$R^{10}$, wherein G is SO.

In certain embodiments, $R^{2b}$ —Z-G-$R^{10}$, wherein G is $SO_2$.

In certain embodiments, $R^{2b}$ is —Z-G-$R^{10}$, wherein $R^{10}$ is a -(6 to 14-membered)aryl or ((6- to 14-membered)aryl)-$(C_1\text{-}C_6)$alkyl-, each optionally substituted with one —$(C_1\text{-}C_6)$alkyl-$CONR^5R^6$, or one $NH_2$—$SO_2(C_1\text{-}C_6)$alkyl-.

In certain embodiments, $R^{2b}$ is —Z-G-$R^{10}$, wherein $R^{10}$ is optionally substituted phenyl or benzyl.

In certain embodiments, $R^{2b}$ is —Z-G-$R^{10}$, wherein $R^{10}$ is piperidinyl optionally substituted with $COOR^7$ or $NH_2$.

In certain embodiments, $R^{2b}$ is —Z-G-$R^{10}$, wherein $R^{10}$ is pyrrolidinyl.

In certain embodiments, $R^{2b}$ is —Z-G-$R^{10}$, wherein $R^{10}$ is -(5- to 12-membered)heteroaryl.

In certain embodiments, $R^{2b}$ is —Z-G-$R^{10}$, wherein $R^{10}$ is optionally substituted pyridinyl.

In other embodiments, $R^{2b}$ is —Z-G-$R^{10}$, wherein $R^{10}$ is furanyl.

In other embodiments, $R^{2b}$ is —Z-G-$R^{10}$, wherein $R^{10}$ is —CH(=O) or —C(=O)—$(C_2\text{-}C_6)$alkenyl, optionally substituted with one -(6- to 14-membered)aryl or one -(5- to 12-membered)heteroaryl.

In certain embodiments, $R^{2b}$ is —Z-G-$R^{10}$, wherein $R^{10}$ is —C(=O)—$(C_1\text{-}C_6)$alkyl-(6- to 14-membered)aryl, optionally substituted with one, two, or three independently selected halo.

In certain embodiments, $R^{2b}$ is —Z-G-$R^{10}$, wherein $R^{10}$ is $NR^5R^6$.

In other embodiments, $R^{2b}$ is —Z-G-$R^{10}$, wherein $R^{10}$ is $NR^5 R^6$ wherein at least one of $R^5$ or $R^6$ is hydrogen.

In other embodiments, $R^{2b}$ is —Z-G-$R^{10}$, wherein $R^{10}$ is $NR^5R^6$ wherein one of $R^5$ or $R^6$ is hydrogen, and the other is —$(C_1\text{-}C_6)$alkyl-$COOR^7$.

In certain embodiments, $R^{2b}$ is —Z-G-$R^{10}$, wherein $R^{10}$ is —$CONR^5R^6$.

In other embodiments, $R^{2b}$ is —Z-G-$R^{10}$, wherein $R^{10}$ is —$CONR^5R^6$, wherein at least one of $R^5$ or $R^6$ is -(6- to 14-membered)aryl substituted with one $R^{30}$ group.

In other embodiments, $R^{2b}$ is —Z-G-$R^{10}$, wherein $R^{10}$ is —$CONR^5R^6$, wherein at least one of $R^5$ or $R^6$ is -(6- to 14-membered)aryl substituted with one —$COOR^7$.

In other embodiments, $R^{2b}$ is —Z-G-$R^{10}$, wherein $R^{10}$ is —$CONR^5R^6$, wherein at least one of $R^5$ or $R^6$ is -(6- to 14-membered)aryl substituted with one —COOH.

In other embodiments, $R^{2b}$ is —Z-G-$R^{10}$, wherein Z is absent, G is =CH— and $R^{10}$ is —$COOR^7$ or —$CONR^5R^6$.

In other embodiments, $R^{2b}$ is —Z-G-$R^{10}$, wherein Z is —$(CH_2)_m$, m is 1 or 2, G is —O— and $R^{10}$ is -hydrogen or —$(C_1\text{-}C_6)$alkyl.

In other embodiments, $R^{2b}$ is $CH_2$—C(O)OH, =C—COOH or —$CH_2OH$.

In certain embodiments, $R^{2a}$ is hydrogen, and $R^{2b}$ is —Z-G-$R^{10}$, wherein Z is absent, G is $NR^8$ where $R^8$ is hydrogen, and $R^{10}$ is —C(=O)—$(C_2\text{-}C_6)$alkenyl substituted with one -(5- to 12-membered)heteroaryl.

In other embodiments, $R^{2a}$ is OH, and $R^{2b}$ is —Z-G-$R^{10}$, wherein Z is absent, G is $NR^8$ where $R^8$ is hydrogen, and $R^{10}$ is —C(=O)—$(C_2\text{-}C_6)$alkenyl substituted with one -(5- to 12-membered)heteroaryl.

In other embodiments, $R^{2a}$ is OH, and $R^{2b}$ is —Z-G-$R^{10}$, wherein Z is absent, G is $NR^8$ wherein $R^8$ is —$(C_1\text{-}C_6)$alkyl, and $R^{10}$ is ((6- to 14-membered)aryl)-$(C_1\text{-}C_6)$alkyl-.

In other embodiments, $R^{2a}$ is OH, and $R^{2b}$ is —Z-G-$R^{10}$, wherein Z is $CH_2$, G is a bond, and $R^{10}$ is —$CONR^5R^6$, wherein one of $R^5$ or $R^6$ is hydrogen, and the other is -(6- to 14-membered)aryl substituted with one —COOH.

In other embodiments, $R^{2a}$ is OH, and $R^{2b}$ is —Z-G-$R^{10}$, wherein Z is absent, G is $NR^8$ wherein $R^8$ is $(C_1\text{-}C_6)$alkyl, and $R^{10}$ is —CH(=O)— substituted with one -(6- to 14-membered)aryl, In certain embodiments, $R^{2a}$ is OH, and $R^{2b}$ is —Z-G-$R^{10}$, wherein Z is $CH_2$, G is O, and $R^{10}$ is -(6- 14-membered)aryl substituted with one —$(C_1\text{-}C_6)$alkyl-$CONR^5R^6$, wherein $R^5$ and $R^6$ are both hydrogen.

In other embodiments, $R^{2a}$ is OH, and $R^{2b}$ is —Z-G-$R^{10}$, wherein Z is absent, G is $NR^8$ wherein $R^8$ is hydrogen, and $R^{10}$ is -(6- 14-membered)aryl substituted with $NH_2$—$SO_2(C_1\text{-}C_6)$alkyl-.

In other embodiments, $R^{2a}$ is OH, and $R^{2b}$ is —Z-G-$R^{10}$, wherein Z is absent, G is $NR^8$ wherein $R^8$ is —$(C_1\text{-}C_6)$alkyl, and $R^{10}$ is -(6- to 14-membered)aryl substituted with $NH_2$—$SO_2(C_1\text{-}C_6)$alkyl-.

In other embodiments, $R^{2a}$ is OH, and $R^{2b}$ is —Z-G-$R^{10}$, wherein Z is absent, G is $NR^8$ wherein $R^8$ is —($C_1$-$C_6$)alkyl, and $R^{10}$ is —C(=O)—($C_2$-$C_6$)alkenyl substituted with, one -(5- to 12-membered)heteroaryl or one -(3- to -12-membered)heterocycle.

In other embodiments, $R^{2a}$ is OH, and $R^{2b}$ is —Z-G-$R^{10}$, wherein Z is absent, G is $NR^8$ wherein $R^8$ is hydrogen, and $R^{10}$ is -(6- to 14-membered)aryl substituted with $NH_2$—$SO_2$($C_1$-$C_6$)alkyl-.

In other embodiments, $R^{2a}$ is OH, and $R^{2b}$ is —Z-G-$R^{10}$, wherein Z is absent, G is $NR^8$ wherein $R^8$ is —($C_1$-$C_6$)alkyl, and $R^{10}$ is —$CONR^5R^6$ wherein one of $R^5$ or $R^6$ is hydrogen and the other is —($C_1$-$C_6$)alkyl-$COOR^7$.

In other embodiments, $R^{2a}$ is OH, and $R^{2b}$ is —Z-G-$R^{10}$, wherein Z is absent, G is a bond, and $R^{10}$ is -(3- to 12-membered)heterocycle substituted with one —COOH.

In other embodiments, $R^{2a}$ is OH, and $R^{2b}$ is —Z-G-$R^{10}$, wherein Z is —$CH_2$—, G is $NR^8$ wherein $R^8$ is hydrogen, and $R^{10}$ is —C(=O)—($C_1$-$C_6$)alkyl-(6- to 14-membered)aryl substituted with two independently selected halo.

In other embodiments, $R^{2a}$ is OH, and $R^{2b}$ is —Z-G-$R^{10}$, wherein Z is absent, G is $NR^8$ wherein $R^8$ is —($C_1$-$C_6$)alkyl, and $R^{10}$ is —$CONR^5R^6$ wherein one of $R^5$ or $R^6$ is hydrogen and the other is —($C_1$-$C_6$)alkyl-$COOR^7$.

In other embodiments, $R^{2a}$ is OH, and $R^{2b}$ is —Z-G-$R^{10}$, wherein Z is absent, G is $NR^8$ wherein $R^8$ is —($C_1$-$C_6$)alkyl, and $R^{10}$ is —C(=O)—($C_2$-$C_6$)alkenyl substituted with one -(3- to 12-membered)heterocycle.

In certain embodiments, $R^3$ is —Z-G-$R^{10}$, provided that —Z-G-$R^{10}$ is other than hydrogen, —($C_1$-$C_6$)alkyl, —($C_2$-$C_6$)alkenyl, or —($C_2$-$C_6$)alkynyl.

In certain embodiments, $R^3$ is —Z-G-$R^{10}$, wherein Z is $CH_2$.

In certain embodiments, $R^3$ is —Z-G-$R^{10}$, wherein G is $NR^8$.

In certain embodiments, $R^3$ is —Z-G-$R^{10}$, wherein G is NH.

In other embodiments, $R^3$ is —Z-G-$R^{10}$, wherein G is $N(C_1$-$C_6$)alkyl.

In other embodiments, $R^3$ is —Z-G-$R^{10}$, wherein G is $NR^8$, wherein $R^8$ is methyl or ethyl In certain embodiments, $R^3$ is —Z-G-$R^{10}$, wherein G is a bond.

In certain embodiments, $R^3$ is —Z-G-$R^{10}$, wherein G is O.

In certain embodiments, $R^3$ is —Z-G-$R^{10}$, wherein G is —OCO—.

In certain embodiments, $R^3$ is —Z-G-$R^{10}$, wherein G is —C(=O).

In certain embodiments, $R^3$ is —Z-G-$R^{10}$, wherein. G is =CH.

In certain embodiments, $R^3$ is —Z-G-$R^{10}$, wherein G is =N—O.

In certain embodiments, $R^3$ is —Z-G-$R^{10}$, wherein G is S.

In certain embodiments, $R^3$ is —Z-G-$R^{10}$, wherein G is SO.

In certain embodiments, $R^3$ is —Z-G-$R^{10}$, wherein G is $SO_2$.

In certain embodiments, $R^3$ is —Z-G-$R^{10}$, wherein $R^{10}$ is a -(6 to 14-membered)aryl or ((6- to 14-membered)aryl)-($C_1$-$C_6$)alkyl-, optionally substituted with —($C_1$-$C_6$)alkyl-$CONR^5R^6$, or $NH_2$—$SO_2(C_1$-$C_6$)alkyl-.

In certain embodiments, $R^3$ is —Z-G-$R^{10}$, wherein $R^{10}$ is optionally substituted phenyl or benzyl.

In certain embodiments, $R^3$ is —Z-G-$R^{10}$, wherein $R^{10}$ is piperidinyl optionally substituted with $COOR^7$ or $NH_2$.

In certain embodiments, $R^3$ is —Z-G-$R^{10}$, wherein $R^{10}$ is pyrrolidinyl In certain embodiments, $R^3$ is —Z-G-$R^{10}$, wherein $R^{10}$ is -(5- to 12-membered)heteroaryl.

In certain embodiments, $R^3$ is —Z-G-$R^{10}$, wherein $R^{10}$ is optionally substituted pyridinyl.

In other embodiments, $R^3$ is —Z-G-$R^{10}$, wherein $R^{10}$ is furanyl

In other embodiments, $R^3$ is —Z-G-$R^{10}$, wherein $R^{10}$ is —C(=O) or —C(=O)—($C_2$-$C_6$)alkenyl, optionally substituted with one -(6- to 14-membered)aryl or one -(5- to 12-membered)heteroaryl.

In certain embodiments, $R^3$ is —Z-G-$R^{10}$, wherein $R^{10}$ is —C(=O)—($C_1$-$C_6$)alkyl-(6- to 14-membered)aryl, optionally substituted with one, two, or three independently selected halo.

In certain embodiments, $R^3$ is —Z-G-$R^{10}$, wherein $R^{10}$ is —$NR^5R^6$.

In other embodiments, $R^3$ is —Z-G-$R^{10}$, wherein $R^{10}$ is —$NR^5R^6$ wherein at least one of $R^5$ or $R^6$ is hydrogen.

In other embodiments, $R^3$ is —Z-G-$R^{10}$, wherein $R^{10}$ is —$NR^5R^6$ wherein at least one of $R^5$ or $R^6$ is hydrogen, and the other is —($C_1$-$C_6$)alkyl-$COOR^7$.

In certain embodiments, $R^3$ is —Z-G-$R^{10}$, wherein $R^{10}$ is —$CONR^5R^6$.

In certain embodiments, $R^3$ is —Z-G-$R^{10}$, wherein $R^{10}$ is —$CONR^5R^6$, wherein at least one of $R^5$ or $R^6$ is -(6- to 14-membered)aryl substituted with one $R^{30}$ group.

In other embodiments, $R^3$ is —Z-G-$R^{10}$, wherein $R^{10}$ is —$CONR^5R^6$, wherein at least one of $R^5$ or $R^6$ is -(6- to 14-membered)aryl substituted with one —$COOR^7$.

In other embodiments, $R^3$ is —Z-G-$R^{10}$, wherein $R^{10}$ is —$CONR^5R^6$, wherein at least one of $R^5$ or $R^6$ is (6- to 14-membered)aryl substituted with one —COOH.

In other embodiments, $R^{2a}$ it is OH, and $R^3$ is —Z-G-$R^{10}$, wherein Z is absent, G is $NR^8$ where $R^8$ is hydrogen, and $R^{10}$ is —C(=O)—($C_2$-$C_6$)alkenyl substituted with one -(5- to 12-membered)heteroaryl.

In other embodiments, $R^{2a}$ is OH, and $R^3$ is —Z-G-$R^{10}$, wherein Z is absent, G is $NR^8$ wherein $R^8$ is —($C_1$-$C_6$)alkyl, and $R^{10}$ is ((6- to 14-membered)aryl)-($C_1$-$C_6$)alkyl-.

In other embodiments, $R^{2a}$ is OH, and $R^3$ is —Z-G-$R^{10}$, wherein Z is —$CH_2$—, G is a bond, and $R^{10}$ is —$CONR^5R^6$, wherein one of $R^5$ or $R^6$ is hydrogen, and the other is -(6- to 14-membered)aryl substituted with one —COOH.

In other embodiments, $R^{2a}$ is OH, and $R^3$ is —Z-G-$R^{10}$, wherein Z is absent, G is $NR^8$ wherein $R^8$ is —($C_1$-$C_6$)alkyl, and $R^{10}$ is —C(=O) substituted with one (6- to 14-membered)aryl.

In certain embodiments, $R^{2a}$ is OH, and $R^3$ is —Z-G-$R^{10}$, wherein Z is —$CH_2$—, G is O, and $R^{10}$ is -(6-14-membered) aryl substituted with one —($C_1$-$C_6$)alkyl-CO—$NR^5R^6$, wherein $R^5$ and $R^6$ are both hydrogen.

In other embodiments, $R^{2a}$ is OH, and $R^3$ is —Z-G-$R^{10}$, wherein Z is absent, G is $NR^8$ wherein $NR^8$ is hydrogen, and $R^{10}$ is -(6-14-membered)aryl substituted with $NH_2$—$SO_2$($C_1$-$C_6$)alkyl-.

In other embodiments, $R^{2a}$ is OH, and $R^3$ is —Z-G-$R^{10}$, wherein Z is absent, Q is $NR^8$ wherein $R^8$ is —($C_1$-$C_6$)alkyl, and $R^{10}$ is -(6- to 14-membered)aryl substituted with $NH_2$—$SO_2(C_1$-$C_6$)alkyl-.

In other embodiments, $R^{2a}$ is OH, and $R^3$ is —Z-G-$R^{10}$, wherein Z is absent, G is $NR^8$ wherein $R^8$ is —($C_1$-$C_6$)alkyl, and $R^{10}$ is —C(=O)—($C_2$-$C_6$)alkenyl substituted with one -(5- to 12-membered)heteroaryl or one -(3- to-12-membered) heterocycle.

In other embodiments, $R^{2a}$ is OH, and $R^3$ is —Z-G-$R^{10}$, wherein Z is absent, G is $NR^8$ wherein $R^8$ is hydrogen, and $R^{10}$ is -(6- to 14-membered)aryl substituted with $NH_2$—$SO_2$($C_1$-$C_6$)alkyl-.

In other embodiments, $R^{2a}$ is OH, and $R^3$ is —Z-G-$R^{10}$, wherein Z is absent, G is $NR^8$ wherein $R^8$ is —($C_1$-$C_6$)alkyl, and $R^{10}$ is —$CONR^5R^6$ wherein one of $R^5$ or $R^6$ is hydrogen and the other is —($C_1$-$C_6$)alkyl-$COOR^7$.

In other embodiments, $R^{2a}$ is OH, and $R^3$ is —Z-G-$R^{10}$, wherein Z is absent, G is a bond, and $R^{10}$ is -(3- to 12-membered)heterocycle substituted with one —COOH.

In other embodiments, $R^{2a}$ is OH, and $R^3$ is —Z-G-$R^{10}$, wherein Z is $CH_2$, G is $NR^8$ wherein $R^8$ is hydrogen, and $R^{10}$ is —C(=O)—($C_1$-$C_6$)alkyl-(6- to 14-membered)aryl substituted with two independently selected halo.

In other embodiments, $R^{2a}$ is OH, and $R^3$ is —Z-G-$R^{10}$, wherein Z is absent, G is $NR^8$ wherein $R^8$ is —($C_1$-$C_6$)alkyl, and $R^{10}$ is —$CONR^5R^6$ wherein one of $R^5$ or $R^6$ is hydrogen and the other is —($C_1$-$C_6$)alkyl-$COOR^7$.

In other embodiments, $R^{2a}$ is OH, and $R^3$ is —Z-G-$R^{10}$, wherein Z is absent, G is $NR^8$ wherein $R^8$ is —($C_1$-$C_6$)alkyl, and $R^{10}$ is —C(=O)—($C_2$-$C_6$)alkenyl substituted with one -(3- to 12-membered)heterocycle.

In certain embodiments, $R^{2b}$ and $R^3$ are different.

In other embodiments, $R^{2b}$ and $R^3$ are the same.

The following embodiments pertain to any one of Formulae I-ID, and the pharmaceutically acceptable salts and solvates thereof.

In certain embodiments, $R^{2a}$ is absent.

In certain embodiments, $R^{2a}$ is absent, and $R^{2b}$ is —Z-G-$R^{10}$, wherein Z is absent, G is $NR^8$ where $R^8$ is hydrogen, and R10 is —C(=O)—($C_2$-$C_6$)alkenyl substituted with one -(5- to 12-membered)heteroaryl.

In other embodiments, $R^{2a}$ is absent, and $R^{2b}$ is —Z-G-$R^{10}$, wherein Z is absent, G is $NR^8$ wherein $R^8$ is —($C_1$-$C_6$)alkyl, and $R^{10}$ is ((6- to 14-membered)aryl)-($C_1$-$C_6$)alkyl-.

In other embodiments, $R^{2a}$ is absent, and $R^{2b}$ is —Z-G-$R^{10}$, wherein Z is $CH_2$, G is a bond, and $R^{10}$ is —$CONR^5R^6$, wherein one of $R^5$ or $R^6$ is hydrogen, and the other is -(6- to 14-membered)aryl substituted with one —COOH.

In other embodiments, $R^{2a}$ is absent; and $R^{2b}$ is —Z-G-$R^{10}$, wherein Z is absent, G is $NR^8$ wherein $R^8$ is ($C_1$-$C_6$)alkyl, and $R^{10}$ is —CH(=O)— substituted with one -(6- to 14-membered)aryl.

In certain embodiments, $R^{2a}$ is absent, and $R^{2b}$ is —Z-G-$R^{10}$, wherein Z is $CH_2$, G is O, and $R^{10}$ is -(6-14-membered)aryl substituted with one —($C_1$-$C_6$)alkyl-$CONR^5R^6$ wherein $R^5$ and $R^6$ are both hydrogen.

In other embodiments, $R^{2a}$ is absent, and $R^{2b}$ is —Z-G-$R^{10}$, wherein Z is absent, G is $NR^8$ wherein $R^8$ is hydrogen, and $R^{10}$ is -(6-14-membered)aryl substituted with $NH_2$—$SO_2$($C_1$-$C_6$)alkyl-.

In other embodiments, $R^{2a}$ is absent, and $R^{2b}$ is —Z-G-$R^{10}$, wherein Z is absent, G is $NR^8$ wherein $R^8$ is —($C_1$-$C_6$)alkyl, and $R^{10}$ is -(6- to 14-membered)aryl substituted with $NH_2$—$SO_2$($C_1$-$C_6$)alkyl-.

In other embodiments, $R^{2a}$ is absent, and $R^{2b}$ is —Z-G-$R^{10}$, wherein Z is absent, G is $NR^8$ wherein $R^8$ is —($C_1$-$C_6$)alkyl, and $R^{10}$ is -(6- to 14-membered)aryl substituted with $NH_2SO_2$($C_1$-$C_6$)alkyl-.

In other embodiments, $R^{2a}$ is absent, and $R^{2b}$ is —Z-G-$R^{10}$, wherein Z is absent, G is $NR^8$ wherein $R^8$ is —($C_1$-$C_6$)alkyl, and $R^{10}$ is —C(=O)—($C_2$-$C_6$)alkenyl substituted with one -(5- to 12-membered)heteroaryl or one -(3- to-12-membered)heterocycle.

In other embodiments, $R^{2a}$ is absent, and $R^{2b}$ is —Z-G-$R^{10}$, wherein Z is absent, G is $NR^8$ wherein $R^8$ is hydrogen, and $R^{10}$ is -(6- to 14-membered)aryl substituted with $NH_2$—$SO_2$($C_1$-$C_6$)alkyl-.

In other embodiments, $R^{2a}$ is absent, and $R^{2b}$ is —Z-G-$R^{10}$, wherein Z is absent, G is $NR^8$ wherein $R^8$ is —($C_1$-$C_6$)alkyl, and $R^{10}$ is —$CONR^5R^6$ wherein one of $R^5$ or $R^6$ is hydrogen and the other is —($C_1$-$C_6$)alkyl-$COOR^7$.

In other embodiments, $R^{2a}$ is absent, and $R^{2b}$ is —Z-G-$R^{10}$, wherein Z is absent, G is a bond, and $R^{10}$ is -(3- to 12-membered)heterocycle substituted with one —COOH.

In other embodiments, $R^{2a}$ is absent, and $R^{2b}$ is —Z-G-$R^{10}$, wherein Z is —$CH_2$—, G is $NR^8$ wherein $R^8$ is hydrogen, and $R^{10}$ is —C(=O)—($C_1$-$C_6$)alkyl-(6- to 14-membered)aryl substituted with two independently selected halo.

In other embodiments, $R^{2a}$ is absent, and $R^{2b}$ is —Z-G-$R^{10}$, wherein Z is absent, G is $NR^8$ wherein $R^8$ is —($C_1$-$C_6$)alkyl, and $R^{10}$ is —$CONR^5R^6$ wherein one of $R^5$ or $R^6$ is hydrogen and the other is —($C_1$-$C_6$)alkyl-$COOR^7$.

In other embodiments, $R^{2a}$ is absent, and $R^{2b}$ is —Z-G-$R^{10}$, wherein Z is absent, G is $NR^8$ wherein $R^8$ is —($C_1$-$C_6$)alkyl, and $R^{10}$ is —C(=O)—($C_2$-$C_6$)alkenyl substituted with one -(3- to 12-membered)heterocycle.

In certain embodiments, $R^{2a}$ is absent, and $R^3$ is —Z-G-$R^{10}$, wherein Z is absent, G is $NR^8$ where $R^8$ is hydrogen, and $R^{10}$ is —C(=O)—($C_2$-$C_6$)alkenyl substituted, with one -(5- to 12-membered)heteroaryl.

In other embodiments, $R^{2a}$ is absent, and $R^3$ is —Z-G-$R^{10}$, wherein Z is absent, G is $NR^8$ wherein $R^8$ is —($C_1$-$C_6$)alkyl, and $R^{10}$ is ((6- to 14-membered)aryl)-($C_1$-$C_6$)alkyl-.

In other embodiments, $R^{2a}$ is absent, and $R^3$ is —Z-G-$R^{10}$, wherein Z is —$CH_2$—, G is a bond, and $R^{10}$ is —$CONR^5R^6$, wherein one of $R^5$ or $R^6$ is hydrogen, and the other is -(6- to 14-membered)aryl substituted with one —COOH.

In other embodiments, $R^{2a}$ is absent, and $R^3$ is —Z-G-$R^{10}$, wherein Z is absent, G is $NR^8$ wherein $R^8$ is —($C_1$-$C_6$)alkyl, and $R^{10}$ is —C(=O) substituted with one (6- to 14-membered)aryl.

In certain embodiments, $R^{2a}$ is absent, and $R^3$ is —Z-$R^{10}$, wherein Z is —$CH_2$—, G is O, and $R^{10}$ is -(6-14-membered)aryl substituted with one —($C_1$-$C_6$)alkyl-CO—$NR^5R^6$, wherein $R^5$ and $R^6$ are both hydrogen.

In other embodiments, $R^{2a}$ is absent, and $R^3$ is —Z-G-$R^{10}$, wherein Z is absent, G is $NR^8$ wherein $R^8$ is hydrogen, and $R^{10}$ is -(6- to 14-membered)aryl substituted with $NH_2$—$SO_2$($C_1$-$C_6$)alkyl-.

In other embodiments, $R^{2a}$ is absent, and $R^3$ is —Z-G-$R^{10}$, wherein Z is absent, G is $NR^8$ wherein $R^8$ is —($C_1$-$C_6$)alkyl, and $R^{10}$ is -(6-to 14-membered)aryl substituted with $NH_2$—$SO_2$($C_1$-$C_6$)alkyl-.

In other embodiments, $R^{2a}$ is absent, and $R^3$ is —Z-G-$R^{10}$, wherein Z is absent G is $NR^8$ wherein $R^8$ is —($C_1$-$C_6$)alkyl, and $R^{10}$ is —C(=O)—($C_1$-$C_6$)alkenyl substituted with one -(5- to 12-membered)heteroaryl or one -(3- to -12-membered)heterocycle.

In other embodiments, $R^{2a}$ is absent and $R^3$ is —Z-G-$R^{10}$, wherein Z is absent, G is $NR^8$ wherein $R^8$ is hydrogen, and $R^{10}$ is -(6- to 14-membered)aryl substituted with $NH_2$—$SO_2$($C_1$-$C_6$)alkyl.

In other embodiments, $R^{2a}$ is absent, and $R^3$ is —Z-G-$R^{10}$, wherein Z is absent, G is $NR^8$ wherein $R^8$ is ($C_1$-$C_6$)alkyl, and $R^{10}$ is —$CONR^5R^6$ wherein one of $R^5$ or $R^6$ is hydrogen and the other is —($C_1$-$C_6$)alkyl-$COOR^7$.

In other embodiments, $R^{2a}$ is absent, and $R^3$ is —Z-G-$R^{10}$, wherein Z is absent, G is a bond, and $R^{10}$ is -(3-to 12-membered)heterocycle substituted with one —COOH.

In other embodiments, $R^{2a}$ is absent, and $R^3$ is —Z-G-$R^{10}$, wherein Z is $CH_2$, G is $NR^8$ wherein $R^8$ is hydrogen, and $R^{10}$ is —C(=O)—($C_1$-$C_6$)alkyl-(6- to 14-membered)aryl substituted with two independently selected halo.

In other embodiments, $R^{2a}$ is absent, and $R^3$ is —Z-G-$R^{10}$, wherein Z is absent, G is $NR^8$ wherein $R^8$ is —($C_1$-$C_6$)alkyl, and $R^{10}$ is —$CONR^5R^6$ wherein one of $R^5$ or $R^6$ is hydrogen and the other is —($C_1$-$C_6$)alkyl-$COOR^7$.

In other embodiments, $R^{2a}$ is absent, and $R^3$ is —Z-G-$R^{10}$, wherein Z is absent, G is $NR^8$ wherein $R^8$ is —($C_1$-$C_6$)alkyl, and $R^{10}$ is —C(=O)—($C_2$-$C_6$)alkenyl substituted with one -(3- to 12-membered)heterocycle.

The following embodiments pertain to any one of Formulae I'-ID', and the pharmaceutically acceptable salts and solvates thereof.

In certain embodiments, $R^{2a}$ is hydrogen.

In certain embodiments, $R^{2a}$ is hydrogen, and $R^{2b}$ is —Z-G-$R^{10}$, wherein Z is absent, G is $NR^8$ where $R^8$ is hydrogen, and $R^{10}$ is —C(=O)—($C_2$-$C_6$)alkenyl substituted with one -(5- to 12-membered)heteroaryl.

In other embodiments, $R^{2a}$ is hydrogen, and $R^{2b}$ is —Z-G-$R^{10}$, wherein Z is absent, G is $NR^8$ wherein $R^8$ is —($C_1$-$C_6$)alkyl, and $R^{10}$ is ((6- to 14-membered)aryl)-($C_1$-$C_6$)alkyl-.

In other embodiments, $R^{2a}$ is hydrogen, and $R^{2b}$ is —Z-G-$R^{10}$, wherein Z is $CH_2$, G is a bond, and $R^{10}$ is —$CONR^5R^6$, wherein one of $R^5$ or $R^6$ is hydrogen, and the other is -(6- to 14-membered)aryl substituted with one —COOH.

In other embodiments, $R^{2a}$ is hydrogen, and $R^{2b}$ is —Z-G-$R^{10}$, wherein Z is absent, G is $NR^8$ wherein $R^8$ is ($C_1$-$C_6$) alkyl, and $R^{10}$ is —CH(=O)— substituted with one -(6- to 14-membered)aryl.

In certain embodiments, $R^{2a}$ is hydrogen, and $R^{2b}$ is —Z-G-$R^{10}$, wherein Z is $CH_2$, G is O, and $R^{10}$ is -(6- 14-membered)aryl substituted with one —($C_1$-$C_6$)alkyl-$CONR^5R^6$, wherein $R^5$ and $R^6$ are both hydrogen.

In other embodiments, $R^{2a}$ is hydrogen, and $R^{2b}$ is —Z-G-$R^{10}$, wherein Z is absent, G is $NR^8$ wherein $R^8$ is hydrogen, and $R^{10}$ is -(6-14-membered)aryl substituted with $NH_2$—$SO_2$($C_1$-$C_6$)alkyl-.

In other embodiments, $R^{2a}$ is hydrogen, and $R^{2b}$ is —Z-G-$R^{10}$, wherein Z is absent, G is $NR^8$ wherein $R^8$ is —($C_1$-$C_6$)alkyl, and $R^{10}$ is -(6- to 14-membered)aryl substituted with $NH_2$—$SO_2$($C_1$-$C_6$)alkyl-.

In other embodiments, $R^{2a}$ is hydrogen, and $R^{2b}$ is —Z-G-$R^{10}$, wherein Z is absent, G is $NR^8$ wherein $R^8$ is —($C_1$-$C_6$)alkyl, and $R^{10}$ is —C(=O)—($C_2$-$C_6$)alkenyl substituted, with one -(5- to 12-membered)heteroaryl or one -(3- to -12-membered)heterocycle.

In other embodiments, $R^{2a}$ is hydrogen, and $R^{2b}$ is —Z-G-$R^{10}$, wherein Z is absent, G is $NR^8$ wherein $R^8$ is hydrogen, and $R^{10}$ is -(6- to 14-membered)aryl substituted with $NH_2$—$SO_2$($C_1$-$C_6$)alkyl-.

In other embodiments, $R^{2a}$ is hydrogen, and $R^{2b}$ is —Z-G-$R^{10}$, wherein Z is absent, G is $NR^8$ wherein $R^8$ is —($C_1$-$C_6$)alkyl, and $R^{10}$ is —$CONR^5R^6$ wherein one of $R^5$ or $R^6$ is hydrogen and the other is —($C_1$-$C_6$)alkyl-$COOR^7$.

In other embodiments, $R^{2a}$ is hydrogen, and $R^{2b}$ is —Z-G-$R^{10}$, wherein Z is absent, G is a bond, and $R^{10}$ is -(3- to 12-membered)heterocycle substituted with one —COOH.

In other embodiments, $R^{2a}$ is hydrogen, and $R^{2b}$ is —Z-G-$R^{10}$, wherein Z is —$CH_2$—, G is $NR^8$ wherein $R^8$ is hydrogen, and $R^{10}$ is —C(=O)—($C_1$-$C_6$)alkyl-(6- to 14-membered) aryl substituted with two independently selected halo.

In other embodiments, $R^{2a}$ is hydrogen, and $R^{2b}$ is —Z-G-$R^{10}$, wherein Z is absent, G is $NR^8$ wherein $R^8$ is —($C_1$-$C_6$) alkyl, and $R^{10}$ is —$CONR^5R^6$ wherein one of $R^5$ or $R^6$ is hydrogen and the other is —($C_1$-$C_6$)alkyl-$COOR^7$.

In other embodiments, $R^{2a}$ is hydrogen, and $R^{2b}$ is —Z-G-$R^{10}$, wherein Z is absent, G is $NR^8$ wherein $R^8$ is —($C_1$-$C_6$) alkyl, and $R^{10}$ is —C(=O)—($C_2$-$C_6$)alkenyl substituted with one -(3- to 12-membered)heterocycle.

In certain embodiments, $R^{2a}$ is hydrogen, and $R^3$ is —Z-G-$R^{10}$, wherein Z is absent, G is $NR^8$ where $R^8$ is hydrogen, and $R^{10}$ is —C(=O)—($C_2$-$C_6$)alkenyl substituted with one -(5- to 12-membered)heteroaryl.

In other embodiments, $R^{2a}$ is hydrogen, and $R^3$ is —Z-G-$R^{10}$, wherein Z is absent, G is $NR^8$ wherein $R^8$ is —($C_1$-$C_6$) alkyl, and $R^{10}$ is ((6- to 14-membered)aryl)-($C_1$-$C_6$)alkyl-.

In other embodiments, $R^{2a}$ is hydrogen, and $R^3$ is —Z-G-$R^{10}$, wherein Z is —$CH_2$—, G is a bond, and $R^{10}$ is —$CONR^5R^6$, wherein one of $R^5$ or $R^6$ is hydrogen, and the other is -(6- to 14-membered)aryl substituted with one —COOH.

In other embodiments, $R^{2a}$ is hydrogen and $R^3$ is —Z-G-$R^{10}$, wherein Z is absent, G is $NR^8$ wherein $R^8$ is —($C_1$-$C_6$) alkyl, and $R^{10}$ is —C(=O) substituted with one (6- to 14-membered)aryl.

In other embodiments, $R^{2a}$ is hydrogen, and $R^3$ is —Z-G-$R^{10}$, wherein Z is —$CH_2$—, G is O, and $R^{10}$ is -(6-14-membered)aryl substituted with one —($C_1$-$C_6$)alkyl-CO—$NR^5R^6$, wherein $R^5$ and $R^6$ are both hydrogen.

In other embodiments, $R^{2a}$ is hydrogen, and $R^3$ is —Z-G-$R^{10}$, wherein Z is absent, G is $NR^8$ wherein $R^8$ is hydrogen, and $R^{10}$ is -(6- to 14-membered)aryl substituted with $NH_2$—$SO_2$($C_1$-$C_6$)alkyl.

In other embodiments, $R^{2a}$ is hydrogen, and $R^3$ is —Z-G-$R^{10}$, wherein Z is absent, G is $NR^8$ wherein $R^8$ is —($C_1$-$C_6$) alkyl, and $R^{10}$ is -(6-to 14-membered)aryl substituted with $NH_2$—$SO_2$($C_1$-$C_6$)alkyl.

In other embodiments, $R^{2a}$ is hydrogen, and $R^3$ is —Z-G-$R^{10}$, wherein Z is absent, G is $NR^8$ wherein $R^8$ is —($C_1$-$C_6$) alkyl, and $R^{10}$ is —C(=O)—($C_2$-$C_6$)alkenyl substituted with one -(5- to 12-membered)heteroaryl or one -(3- to-12-membered)heterocycle.

In other embodiments, $R^{2a}$ is hydrogen, and $R^3$ is —Z-G-$R^{10}$, wherein Z is absent, G is $NR^8$ wherein $R^8$ is hydrogen, and $R^{10}$ is -(6- to 14-membered)aryl substituted with $NH_2$—$SO_2$($C_1$-$C_6$)alkyl-.

In other embodiments, $R^{2a}$ is hydrogen, and $R^3$ is —Z-G-$R^{10}$, wherein Z is absent, G is $NR^8$ wherein $R^8$ is —($C_1$-$C_6$) alkyl, and $R^{10}$ is —$CONR^5R^6$ wherein one of $R^5$ or $R^6$ is hydrogen and the other is —($C_1$-$C_6$)alkyl-$COOR^7$.

In other embodiments, $R^{2a}$ is hydrogen, and $R^3$ is —Z-G-$R^{10}$, wherein Z is absent, G is a bond, and $R^{10}$ is -(3-to 12-membered)heterocycle substituted with one —COOH.

In other embodiments, $R^{2a}$ is hydrogen, and $R^3$ is —Z-G-$R^{10}$, wherein Z is $CH_2$, G is $NR^8$ wherein $R^8$ is hydrogen, and $R^{10}$ is —C(=O)—($C_1$-$C_6$)alkyl-(6- to 14-membered)aryl substituted with two independently selected halo.

In other embodiments, $R^{2a}$ is hydrogen, and $R^3$ is —Z-G-$R^{10}$, wherein Z is absent, G is $NR^8$ wherein $R^8$ is —($C_1$-$C_6$) alkyl, and $R^{10}$ is —$CONR^5R^6$ wherein one of $R^5$ or $R^6$ is hydrogen and the other is —($C_1$-$C_6$)alkyl-$COOR^7$.

In other embodiments, $R^{2a}$ is hydrogen, and $R^3$ is —Z-G-$R^{10}$, wherein Z is absent, G is $NR^8$ wherein $R^8$ is —($C_1$-$C_6$) alkyl, and $R^{10}$ is —C(=O)—($C_2$-$C_6$)alkenyl substituted with one -(3- to 12-membered)heterocycle.

Specific compounds of the invention include:

4-((2R,6R,11R)-11-(carboxymethyl)-3-(cyclopropylmethyl)-8-hydroxy-1,2,3,4,5,6-hexahydro-2,6-methanobenzo[d]azocin-6-yl)butanoic acid (Compound 10);

(Z)-2-((2R,6S)-6-(4-amino-4-oxobutyl)-3-(cyclopropylmethyl)-8-hydroxy-1,2,3,4,5,6-hexahydro-2,6-methanobenzo[d]azocin-11-ylidene)acetic acid (Compound 11);

(Z)-2-((2R,6S)-3-(cyclopropylmethyl)-6-(4-(dimethylamino)-4-oxobutyl)-8-hydroxy-1,2,3,4,5,6-hexahydro-2,6-methanobenzo[d]azocin-11-ylidene)acetic acid (Compound 12);

4-((2R,6S,Z)-11 -(carboxymethylene)-3-(cyclopropylmethyl)-8-hydroxy-1,2,3,4,5,6-hexahydro-2,6-methanobenzo[d]azocin-6-yl)butanoic acid (Compound 13);

2-((2R,6S,11R)-3-(cyclopropylmethyl)-11-(hydroxymethyl)-8-methoxy-1,2,3,4,5,6-hexahydro-2,6-methanobenzo[d]azocin-6-yl)ethanol (Compound 19);

2-((2R,6S,11R)-3-(cyclopropylmethyl)-11-(hydroxymethyl)-8-methoxy-1,2,3,4,5,6-hexahydro-2,6-methanobenzo[d]azocin-6yl)acetamide (Compound 22);

and the pharmaceutically acceptable salts and solvates thereof.

As used herein, the term "—$(C_1$-$C_{52})$alkyl" refers to straight-chain and branched non-cyclic saturated hydrocarbons having from 1 to 52 carbon atoms.

As used herein, the term "—$(C_1$-$C_{10})$alkyl" refers to straight-chain and branched non-cyclic saturated hydrocarbons having 1, 2, 3, 4, 5, 6, 7, 8, 9, or 10 carbon atoms. Representative straight chain —$(C_1$-$C_{10})$alkyl groups include methyl, -ethyl, -n-propyl, -n-butyl, -n-pentyl, -n-hexyl, n-heptyl, n-octyl, n-nonyl and n-decyl. Representative branched —$(C_1$-$C_{10})$alkyl groups, having from 3 to 10 carbon atoms, include isopropyl, sec-butyl, isobutyl, tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 5-methylhexyl, 6-methylheptyl, and the like.

As used herein, the term "—$(C_1$-$C_6)$alkyl" refers to straight-chain and branched non-cyclic saturated hydrocarbons having 1, 2, 3, 4, 5, or 6 carbon atoms. Representative straight chain —$(C_1$-$C_6)$alkyl groups include methyl, -ethyl, -n-propyl, -n-butyl, -n-pentyl, and -n-hexyl. Representative branched-chain —$(C_1$-$C_6)$alkyl groups, having from 3 to 6 carbon atoms, include isopropyl, sec-butyl, isobutyl, tert-butyl, isopentyl, neopentyl, 1-methylbutyl, 2-methylbutyl, 3-methylbutyl, 1,1-dimethylpropyl, and 1,2-dimethylpropyl, methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, and the like.

As used herein, the term "—$(C_1$-$C_6)$alkylene" refers to straight-chain or branched non-cyclic hydrocarbons having 1, 2, 3, 4, 5, or 6 carbon atoms exhibiting an alkanediyl group. Representative straight chain —$(C_1$-$C_6)$alkylene groups include methylene, ethylene, propylene, butylene, pentylene, hexylene and the like.

As used herein, the term "—$(C_2$-$C_{54})$alkenyl" refers to straight and branched non-cyclic hydrocarbons having from 2 to 54 carbon atoms, and including at least one carbon-carbon double bond.

As used herein, the term "—$(C_2$-$C_{12})$alkenyl" refers to straight chain and branched non-cyclic hydrocarbons having 2, 3, 4, 5, 6, 7, 8, 9, 10, 11, or 12 carbon atoms and including at least one carbon-carbon double bond. Representative straight chain and branched —$(C_2$-$C_{12})$alkenyl groups include -vinyl, allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, 3-hexenyl, and the like.

As used herein, the term "—$(C_2$-$C_6)$alkenyl" refers to straight chain and branched non-cyclic hydrocarbons having 2, 3, 4, 5, or 6 carbon atoms and including at least one carbon-carbon double bond. Representative straight chain and branched —$(C_2$-$C_6)$alkenyl groups include -vinyl, allyl -1-butenyl, -2-butenyl, -isobutylenyl, -1-pentenyl, -2-pentenyl -3-methyl-1-butenyl, -2-methyl-2-butenyl, and the like.

As used herein, the term "—$(C_3$-$C_7)$alkenyl" refers to straight chain and branched non-cyclic hydrocarbons having 3, 4, 5, 6 or 7 carbon atoms and including at least one carbon-carbon double bond. Representative straight chain and branched —$(C_3$-$C_7)$alkenyl groups include allyl, -1-butenyl, -2-butenyl, -isobutylenyl, -1-pentenyl, -2-pentenyl, -3-methyl-1-butenyl, -2-methyl-2-butenyl and the like.

As used herein, the term "—$(C_2$-$C_6)$alkenylene" refers to straight-chain or branched non-cyclic hydrocarbons having 1, 2, 3, 4, 5, or 6 carbon atoms and at least one carbon-carbon double bond and exhibiting an alkenediyl group. Representative straight chain —$(C_1$-$C_6)$alkenylene groups include vinylene, propenylene, butenylene, pentenylene, hexenylene and the like.

As used herein, the term "—$(C_2$-$C_{54})$alkynyl" refers to straight chain and branched non-cyclic hydrocarbons having from 2 to 54 carbon atoms, and including at least one carbon-carbon triple bond.

As used herein, the term "—$(C_2$-$C_{12})$alkynyl" refers to straight chain and branched non-cyclic hydrocarbons having 2, 3, 4, 5, 6, 7, 8, 9, 10, 11, or 12 carbon atoms and including at least one carbon-carbon triple bond. Representative straight chain and branched —$(C_2$-$C_{12})$alkynyl groups include -acetylenyl, -propynyl, -1 butynyl, -2-butynyl, -1-pentynyl, -2-pentynyl, -3-methyl-1-butynyl, -4-pentynyl, -1-hexynyl, -2-hexynyl, -5-hexynyl, and the like.

As used herein, the term "—$(C_2$-$C_6)$alkynyl" refers to straight chain and branched non-cyclic hydrocarbons having 2, 3, 4, 5, or 6 carbon atoms and including at least one carbon-carbon triple bond. Representative straight chain and branched —$(C_2$-$C_6)$alkynyl groups include -acetylenyl, -propynyl, -1 butynyl, -2-butynyl, -1-pentynyl, -2-pentynyl, -3-methyl-1-butynyl, -4-pentynyl, and the like.

As used herein, "—$(C_1$-$C_{10})$alkoxy" means a straight chain or branched non-cyclic hydrocarbon having one or more ether groups and 1, 2, 3, 4, 5, 6, 7, 8, 9, or 10 carbon atoms. Representative straight chain and branched $(C_1$-$C_{10})$ alkoxys include -methoxy, -ethoxy, -propoxy, -butyloxy, -pentyloxy, -hexyloxy, -heptyloxy, -methoxymethyl, -2-methoxyethyl, -5-methoxypentyl, -3-ethoxybutyl, and the like.

As used herein, "—$(C_1$-$C_6)$alkoxy" means a straight chain or branched non-cyclic hydrocarbon having one or more ether groups and 1, 2, 3, 4, 5, or 6 carbon atoms. Representative straight chain and branched $(C_1$-$C_6)$alkoxys include -methoxy, -ethoxy, -propoxy, -butyloxy, -pentyloxy, -hexyloxy, -methoxymethyl, -2-methoxyethyl, -5-methoxypentyl, -3-ethoxybutyl and the like.

As used herein, "—$(C_1$-$C_5)$alkoxy" means a straight chain or branched non-cyclic hydrocarbon having one or more ether groups and from 1 to 5 carbon atoms. Representative straight chain and branched $(C_1$-$C_5)$alkoxys include -methoxy, -ethoxy, -propoxy, -butyloxy, -pentyloxy, -methoxymethyl, -2-methoxyethyl, -5-methoxypentyl, -3-ethoxybutyl and the like.

As used herein, the term "—$(C_3-C_{12})$cycloalkyl" refers to a cyclic saturated hydrocarbon ring having 3, 4, 5, 6, 7, 8, 9, 10, 11 or 12 carbon atoms. Representative $(C_3-C_{12})$cycloalkyls include cyclopropyl, cyclobutyl, cyclopentyl, cyclohexyl, cycloheptyl, cyclooctyl, and cyclononyl, cyclodecyl, cycloundecyl, cyclododecyl, and the like.

As used herein, "—$(C_6-C_{14})$bicycloalkyl" means a bicyclic hydrocarbon ring system having 6, 7, 8, 9, 10, 11, 12, 13, or 14 carbon atoms and at least one saturated cyclic alkyl ring. Representative —$(C_6-C_{14})$bicycloalkyls include -indanyl -norbornyl, -1,2,3,4-tetrahydronaphthalenyl, 5,6,7,8-tetrahydronaphthalenyl, -perhydronaphthalenyl and the like.

As used herein, "—$(C_8-C_{20})$cycloalkyl" means a tricyclic hydrocarbon ring system having 8, 9, 10, 11, 12, 13, 14, 15, 16, 17, 18, 19, or 20 carbon atoms and at least one saturated cyclic alkyl ring. Representative —$(C_8-C_{20})$tricycloalkyls include -pyrenyl, -adamantyl, -1,2,3,4-tetrahydroanthracenyl, -perhydroanthracenyl-aceanthrenyl, -1,2,3,4-tetrahydropenanthrenyl, -5,6,7,8-tetrahydrophenanthrenyl, -perhydrophenanthrenyl, tetradecahydro-1H-cyclohepta[a]naphthalenyl, tetradecahydro-1H-cycloocta[e]indenyl, tetradecahydro-1H-cyclohepta[e]azulenyl, hexadecahydrocycloocta[b]naphthalenyl, hexadecahydrocyclohepta[a]heptalenyl, tricyclo-pentadecanyl, tricyclo-octadecanyl tricyclo-nonadecanyl, tricyclo-icosanyl, and the like.

As used herein, the term "—$(C_3-C_{12})$cycloalkenyl" refers to a cyclic hydrocarbon having from 3 to 12 carbon atoms, and including at least one carbon-carbon double bond. Representative —$(C_3-C_{12})$cycloalkenyls include -cyclobutenyl, -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctadienyl, -cyclooctatetraenyl, -cyclononenyl, -cyclononadienyl, -cyclodecenyl, -cyclodecadienyl, -norbornenyl, and the like.

As used herein, the term "—$(C_4-C_{12})$cycloalkenyl" refers to a cyclic hydrocarbon having from 4 to 12 carbon atoms, and including at least one carbon-carbon double bond. Representative —$(C_4-C_{12})$cycloalkenyls include -cyclobutenyl, -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl -cyclononadienyl -cyclodecenyl, -cyclodecadienyl, -norbornenyl, and the like.

As used herein, "—$(C_7-C_{14})$bicycloalkenyl" means a bicyclic hydrocarbon ring system having at least one carbon-carbon double bond in at least one of the rings and 7, 8, 9, 10, 11, 12, 13, or 14 carbon atoms. Representative —$(C_7-C_{14})$ bicycloalkenyls include -bicyclo[3.2.0]hept-2-enyl, -indenyl, -pentalenyl, -naphthalenyl, -azulenyl, -heptalenyl, -1,2,7,8-tetrahydronaphthalenyl, and the like.

As used herein, "—$(C_8-C_{20})$tricycloalkenyl" means a tricyclic hydrocarbon ring system having at least one carbon-carbon double bond in one of the rings and 8, 9, 10, 11, 12, 13, 14, 15, 16, 17, 18, 19 or 20 carbon atoms. Representative —$(C_8-C_{20})$tricycloalkenyls include -anthracenyl, -phenanthrenyl, -phenalenyl, -acenaphthalenyl, as-indacenyl, s-indacenyl, 2,3,6,7,8,9,10,11-octahydro-1H-cycloocta[e]indenyl, 2,3,4,7,8,9,10,11-octahydro-1H-cyclohepta[a]naphthalenyl, 8,9,10,11-tetrahydro-7H-cyclohepta[a]naphthalenyl, 2,3,4,5,6,7,8,9,10,11,12,13-dodecahydro-1H-cyclohepta[a]heptalenyl 1,2,3,4,5,6,7,8,9,10,11,12,13,14-tetradecahydro-dicyclohepta[a,c]cyclooctenyl, 2,3,4,5,6,7,8,9,10,11,12,13-dodecahydro-1H-dibenzo[a,d]cyclononenyl, and the like.

As used herein, "-(3- to 12-membered)heterocycle" or "-(3- to 12-membered)heterocyclo" means a 3- to 12-membered monocyclic ring having one or more heteroatoms, which is either saturated, unsaturated, non-aromatic, or aromatic. A 3-membered heterocycle can contain up to 1 heteroatom; a 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(3- to 12-membered) heterocycle can be attached via a nitrogen or carbon atom. Representative -(3- to 12-membered)heterocycles include thiazolidinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

As used herein, "-(4- to 8-membered)heterocycle" or "-(4- to 8-membered)heterocyclo" means a 4- to 8-membered monocyclic heterocyclic ring which is either saturated or unsaturated, non-aromatic, or aromatic. A 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(4- to 8-membered)heterocycle can be attached via a nitrogen or carbon atom. Representative -(4- to 8-membered)heterocycles include morpholinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

As used herein, "-(7- to 12-membered)bicycloheterocycle" or "-(7- to 12-membered)bicycloheterocyclo" means a 7- to 12-membered bicyclic, heterocyclic ring which is either saturated, unsaturated, non-aromatic, or aromatic. At least one ring of the bicycloheterocycle contains at least one heteroatom. A -(7- to 12-membered)bicycloheterocycle contains from 1 to 4 heteroatoms independently selected from nitrogen (which can be quaternized), oxygen, and sulfur (including sulfoxide and sulfone). The -(7- to 12-membered)bicycloheterocycle can be attached via a nitrogen of carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl -quinolyl, -phthalazinyl, -naphthyridinyl, -carbazolyl, -β-carbolinyl, -indolinyl, isoindolinyl, -1,2,3,4-tetrahydroquinolinyl, -1,2,3,4-tetrahydroisoquinolinyl, pyrrolopyrrolyl and the like.

As used herein a "-(6- to 14- membered)aryl" means an aromatic carbocyclic ring containing 6 to 14 carbon atoms, including both mono- and bicyclic ring systems. Representative -(6- to 14-membered)aryl groups include -indenyl, -phenyl, -naphthyl, anthracenyl, and the like.

As used herein a "-(7-to 12- membered)bicyclic aryl" means a bicyclic aromatic carbocyclic ring containing 7 to 12 carbon atoms. Representative -(7- to 12-membered)bicyclic aryl groups include -indenyl, -naphthyl, and the like.

As used herein a "-(5- to 12- membered)aryloxy" means an oxygen substituted by an aromatic carbocyclic ring containing 5 to 12 carbon atoms, including both mono- and bicyclic ring systems. Representative -5- to 12-membered)aryloxy groups include phenoxy and 4-fluorophenoxy, and the like.

As used herein a "-(6- to 14- membered)aryloxy" means an oxygen substituted by an aromatic carbocyclic ring containing 6 to 14 carbon atoms, including both, mono- and bicyclic ring systems. Representative -6- to 14-membered)aryloxy groups include phenoxy and 4-fluorophenoxy, and the like.

As used herein a "hydroxy$(C_1-C_6)$alkyl" means any of the above-mentioned $C_1-C_6$ alkyl groups substituted by one or more hydroxy groups. Representative hydroxy$(C_1-C_6)$alkyl groups include hydroxymethyl, hydroxyethyl, hydroxypropyl and hydroxybutyl groups, and especially hydroxymethyl, 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

As used herein a "dihydroxy($C_1$-$C_6$)alkyl" means any of the above-mentioned $C_1$-$C_6$ alkyl groups substituted by two hydroxy groups. Representative dihydroxy($C_1$-$C_6$)alkyl groups include dihydroxyethyl, dihydroxypropyl and dihydroxybutyl groups, and especially 1,2-dihydroxyethyl, 1,3-dihydroxypropyl, 2,3-dihydroxypropyl, 1,3-dihydroxybutyl, 1,4-dihydroxybutyl, and 1,3-dihydroxyprop-2-yl.

As used herein a "-(5- to 12- membered)carbocyclic ring" means a hydrocarbon ring system having from 5 to 12 carbon atoms, which is either saturated, unsaturated, non-aromatic or aromatic.

As used herein a "-(7- to 12- membered)bicyclic ring system" means a two-ring system having 7 to 12 ring atoms that are either all carbon atoms (i.e., carbocyclic) or combine carbon atoms with one or more heteroatoms independently selected from nitrogen, oxygen, and sulfur (i.e., heterocyclic), and which may be either unsaturated, saturated, non-aromatic or aromatic.

As used herein, "-(5- to 12-membered)heteroaryl" means an aromatic heterocycle ring of 5 to 12 members, including both mono- and bicyclic ring systems, where at least one carbon atom (of one or both of the rings) is replaced with a heteroatom independently selected from nitrogen, oxygen, and sulfur, or at least two carbon atoms of one of both of the rings are replaced with a heteroatom independently selected from nitrogen, oxygen, and sulfur. In one embodiment, one of the bicyclic -(5- to 12-membered)heteroaryl rings contains at least one carbon atom. In another embodiment, both of the bicyclic -(5- to 12-membered)heteroaryl rings contain at least one carbon atom. Representative -(5- to 12-membered)heteroaryls include pyridyl furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, thiadiazolyl, cinnolinyl, phthalazinyl, quinazolinyl, and the like.

As used herein, the terms "halo" and "halogen" refer to fluoro, chloro, bromo or iodo.

As used herein, the term "halo($C_1$-$C_6$)alkyl" refers to one of the above ($C_1$-$C_6$)alkyl groups wherein one or more of the hydrogen atoms have been replaced by a halogen.

As used herein, "—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

As used herein, "—CH(halo)$_2$" means a methyl group where two of the hydrogens of the methyl group have been replaced with independently selected halogen atoms. Representative —CH(halo)$_2$ groups include —$CHF_2$, —$CHCl_2$, —$CHBr_2$, —$CHBrCl$, —$CHClI$, and —$CHI_2$.

As used herein, "-C(halo)$_3$" means a methyl group where each of the hydrogens of the methyl group has been replaced with independently selected halogen atoms. Representative —C(halo)$_3$ groups include —$CF_3$, —$CCl_3$, —$CBr_3$, and —$Cl_3$.

As used herein, the term "sulfonyl" refers to a —$SO_2$— group.

As used herein the term "diphenyl($C_1$-$C_6$)alkyl" refers to one of the above ($C_1$-$C_6$)alkyl groups substituted with two phenyl groups.

As used herein, the terms "animal," "patient" and/or "subject" mean a human- or non-human animal.

As used herein, the term "optionally substituted" refers to a group that is either unsubstituted or substituted.

Optional substituents on optionally substituted groups, when not otherwise indicated, include 1, 2, or 3 groups each independently selected from the group consisting of —($C_1$-$C_6$)alkyl, OH, halo, —C(halo)$_3$, —CH(halo)$_2$, —$CH_2$(halo), $NH_2$, —NH($C_1$-$C_6$)alkyl, CN, SH, -(5- to 12-membered)carbocyclic ring, -(5- to 12-membered)heterocycle, phenyl, benzyl, (=O), halo($C_1$-$C_6$)alkyl-, ($C_2$-$C_6$)alkenyl, ($C_2$-$C_6$)alkynyl, hydroxy($C_1$-$C_6$)alkyl—, $OR^{4a}$ (such as —OC(halo)$_3$ and —O($C_1$-$C_6$)alkyl), —$CONR^{5b}R^{6b}$ and —$COOR^{7a}$; where $R^{4a}$ is selected from the group consisting of —($C_1$-$C_6$)alkyl, —($C_2$-$C_6$)alkenyl, —($C_2$-$C_6$)alkynyl, —C(halo)$_3$, hydroxy ($C_1$-$C_6$)alkyl-, —($C_3$-$C_{12}$)cycloalkyl, —($C_6$-$C_{14}$)bicycloalkyl, —($C_8$-$C_{20}$)tricycloalkyl, —($C_4$-$C_{12}$)cycloalkenyl, —($C_7$-$C_{14}$)bicycloalkenyl, —($C_8$-$C_{20}$)tricycloalkenyl, -(5- to 12-membered)aryl, -(5- to 12-membered)heteroaryl, -(3-to 12-membered)heterocycle, and -(7- to 12-membered)bicycloheterocycle; $R^{5b}$ and $R^{6b}$ are each independently selected from the group consisting of —($C_1$-$C_6$)alkyl, —($C_3$-$C_8$)cycloalkyl, (($C_3$-$C_8$)cycloalkyl)-($C_1$-$C_6$)alkyl-, or together with the nitrogen atom to which they may both be attached form a (4- to 8-membered)heterocycle; and $R^{7a}$ is selected from the group consisting of hydrogen, —($C_1$-$C_6$)alkyl, —($C_2$-$C_6$) alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)alkoxy-$COOR^7$, —NH—C(=O)—NH—($C_1$-$C_6$)alkyl, —NH—C(=O)-(5- to 12-membered)aryl, —NH—C (=O)—($C_1$-$C_6$)alkyl-(5- to 12-membered)aryl, —NH—($C_1$-$C_6$)alkyl-$COOR^7$, —NH—C(=O)—($C_1$-$C_6$)alkyl-$COOR^7$, —NH—C(=O)—CH($NH_2$)—($C_1$-$C_6$)alkyl-$COOR^7$, —($C_3$-$C_{12}$)cycloalkyl, -(5- to 12-membered)aryl, -(5- to 12-membered)aryloxy, —($C_1$-$C_6$)alkoxy-$CONR^5R^6$, —NH—($C_1$-$C_6$)alkyl-$CONR^5R^6$, —(=O)NH—($C_1$-$C_6$) alkyl-$COOR^7$, —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-$COOR^7$, —($C_1$-$C_6$)alkoxy-$COOR^7$, —($C_3$-$C_{12}$)cycloalkyl, (($C_3$-$C_{12}$)cycloalkyl)-—($C_1$-$C_6$)alkyl-, (($C_3$-$C_{12}$)cycloalkyl)-($C_1$-$C_6$)alkoxy-, (($C_3$-$C_{12}$)cycloalkyl-($C_1$-$C_6$)alkoxy-($C_1$-$C_6$)alkyl-, ($C_4$-$C_{12}$)cycloalkenyl, (($C_4$-$C_{12}$)cycloalkenyl)-($C_1$-$C_6$)alkyl-, (($C_4$-$C_{12}$) cycloalkenyl)-($C_1$-$C_6$)alkoxy-, (($C_4$-$C_{12}$)cycloalkenyl)-($C_1$-$C_6$)alkoxy-($C_1$-$C_6$)alkyl, -(5- to 12-membered)aryl, ((5- to 12-membered)aryl)-($C_1$-$C_6$)alkyl-, ((5- to 12-membered) aryl)-($C_1$-$C_6$)alkoxy-, ((5- to 12-membered)aryl)-($C_1$-$C_6$) alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl, -(3- to 12-membered) heterocycle, ((3- to 12 membered)heterocycle)-($C_1$-$C_6$) alkyl-, ((3- to 12 membered)heterocycle)-($C_1$-$C_6$)alkoxy-, and ((3- to 12 membered)heterocycle)-($C_1$-$C_6$)alkoxy-($C_1$-$C_6$)alkyl-; wherein $R^5$, $R^6$, and $R^7$ are as defined above for Formula I.

As used herein, compounds that bind to receptors and mimic the regulatory effects of endogenous ligands are defined as "agonists". Compounds that bind to receptors and are only partly effective as agonists are defined as "partial agonists". Compounds that bind to receptors without producing any regulatory effect, but rather block the binding of ligands to the receptor are defined as "antagonists". (Ross and Kenakin, "Ch. 2: Pharmacodynamics: Mechanisms of Drug Action and the Relationship Between Drug Concentration and Effect", pp. 31-32, in *Goodman & Gilman's the Pharmacological Basis of Therapeutics*, 10th Ed. (J. G. Hardman, L. E. Limbird and A. Goodman-Gilman eds., 2001).

Compounds of the Invention can be isotopically-labeled (i.e., radio-labeled). Examples of isotopes that can be incorporated into the disclosed compounds include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, 35S, $^{18}F$ and $^{36}Cl$, respectively, and preferably $^3H$, $^{11}C$, and $^{14}C$. Isotopically-labeled Compounds of the Invention can be prepared by methods known in the art in view of this disclosure. For example, tritiated Compounds of the Invention can be prepared by introducing tritium into the particular compound by catalytic dehalogenation with tritium. This method may include reacting a suitable halogen-substituted precursor of a Compound of the Invention with tritium gas in the presence of an appropriate catalyst such as Pd/C in the presence of a base. Other suitable methods for preparing tritiated compounds are generally described in Filer, Isotopes in the Physical and Biomedical Sciences, Vol. I, Labeled Compounds (Part A), Chapter 6 (1987), $^{14}$C-labeled compounds can be prepared by employing starting materials having a $^{14}$C carbon.

Isotopically labeled Compounds of the Invention, as well as the pharmaceutically acceptable salts and solvates thereof, can be used as radioligands to test for the binding of compounds to an opioid or ORL-1 receptor. For example, a radio-labeled Compound of the Invention can be used to characterize specific binding of a test or candidate compound to the receptor. Binding assays utilizing such radio-labeled compounds can provide an alternative to animal testing for the evaluation of chemical structure-activity relationships. In a non-limiting embodiment, the present invention provides a method for screening a candidate compound for the ability to bind to an opioid or ORL-1 receptor, comprising the steps of: a) introducing a fixed concentration of the radio-labeled compound to the receptor under conditions that permit binding of the radio-labeled compound to the receptor to form a complex; b) titrating the complex with a candidate compound; and c) determining the binding of the candidate compound to said receptor.

Compounds of the Invention disclosed herein may contain one or more asymmetric centers, thus giving rise to enantiomers, diastereomers, and other stereoisomeric forms. The present invention encompasses all such possible forms, as well as their racemic and resolved forms and mixtures thereof, and the uses thereof. The individual enantiomers may be separated according to methods known to those of ordinary skill in the art in view of the present disclosure. When the compounds described herein contain olefinic double bonds or other centers of geometric asymmetry, and unless specified otherwise, they include both E and Z geometric isomers. All tautomers are intended to be encompassed by the present invention as well.

As used herein, the term, "stereoisomer" is a general term for all isomers of individual molecules that differ only in the orientation of their atoms in space. It includes enantiomers and isomers of compounds with more than one chiral center that are not mirror images of one another (diastereoisomers).

The term "chiral center" refers to a carbon atom to which four different groups are attached.

The terms "enantiomer" and "enantiomeric" refer to a molecule that cannot be superimposed on its mirror image and hence is optically active such that the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

Compounds of the Invention encompass all salts of the disclosed compounds of Formula I. The present invention preferably includes any and all non-toxic, pharmaceutically acceptable salts of the disclosed compounds. Examples of pharmaceutically acceptable salts include inorganic and organic acid addition salts and basic salts. The pharmaceutically acceptable salts include, but are not limited to, metal salts such as sodium salt, potassium salt, cesium salt, and the like; alkaline earth metals such as calcium salt, magnesium salt and the like; organic amine salts such as triethylamine salt, pyridine salt, picoline salt, ethanolamine salt, triethanolamine salt, dicylohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts can be formed by mixing a solution of the particular compound of the present invention and a pharmaceutically acceptable non-toxic base such as sodium hydroxide, potassium hydroxide, choline hydroxide, sodium carbonate and the like.

Compounds of the Invention also encompass solvates of the disclosed compounds of Formula I, Formula IA, Formula IB, Formula IC, and Formula ID as well as Formula I', Formula IA', Formula IB', Formula IC', and Formula ID'. The term "solvate" as used herein is a combination, physical association and/or solvation of a Compound of the Invention with a solvent molecule such as, e.g. a disolvate, monosolvate or hemisolvate, where the ratio of solvent molecule to the Compound of the Invention is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. A Compound of the Invention may be present as a solvated form with a pharmaceutically acceptable solvent, such as water, methanol, ethanol, and the like, and it is intended that the invention include both solvated and unsolvated forms of the Compounds of the Invention. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12)2004), and A. L. Bingham et al., *Chem. Commun.*, 603-604 (2001), A typical, non-limiting, process of preparing a solvate would involve dissolving a Compound of the Invention in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present invention also provides the use of a Compound of the Invention in the manufacture of a medicament for treating or preventing a Condition. In one embodiment, the Condition is pain, such as acute or chronic pain. In one embodiment, a Compound of the Invention has agonist activity at the μ, δ and/or κ receptors. In another embodiment a Compound of the Invention has agonist activity at the μ receptor. In another embodiment, a Compound of the Invention has antagonist activity at the ORL-1 receptor. In another embodiment, certain Compounds of the Invention can stimulate one receptor (e.g., a μ, δ and/or κ agonist) and inhibit a different receptor (e.g., an ORL-1 antagonist). In another embodiment, the Compound of the Invention is an agonist at the μ receptor, and an antagonist at the ORL-1 receptor.

List of Abbreviations
ACN acetonitrile
° C. degrees Celsius
d day(s)
DCM dichloromethane
DMF dimethylformamide
h hour(s)
HPLC high pressure liquid chromatography
LAH lithium aluminum hydride
MeOH methanol
min minute(s)
MPLC medium pressure liquid chromatography
NaHMDS sodium hexamethyldisilazide
PTSA p-toluenesulfonic acid
RT room temperature
TFA trifluoroacetic acid
THF tetrahydrofuran Synthesis of Compounds Compounds of the Invention can be made using conventional organic synthesis in view of this disclosure, or by the illustrative methods shown in the schemes below.

Scheme A

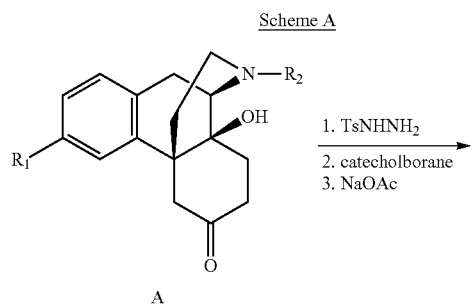

The carbonyl group in compound A (*Tetrahedron Lett.*, 2010, 51, 2359) can be converted into a methylene group by, for example, conversion into a tosyl hydrazone and subsequent treatment with a suitable reducing agent such as catecholborane (*Organic Syntheses, Coll. Vol* 6, p. 293 (1988): Vol. 59, p. 42 (1979). Alcohol B can be dehydrated using a suitable reagent such as thionyl chloride. In a suitable solvent, such as pyridine to yield alkene C. Cleavage of the double bond in compound C can be achieved by a suitable reagent such as ozone in a suitable solvent such as acidic MeOH (*Organic Syntheses, Coll. Vol.* 7, p. 168 (1990); Vol. 64, p. 150 (1986) to give keto-acetal D.

Scheme B

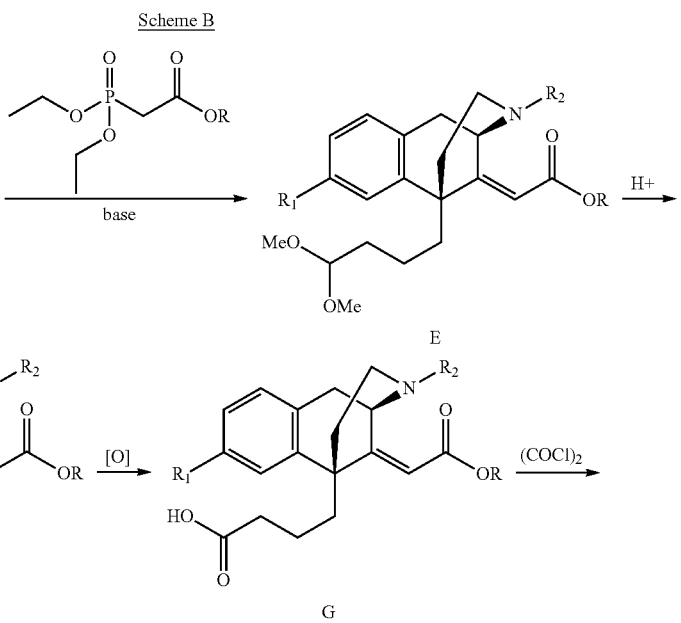

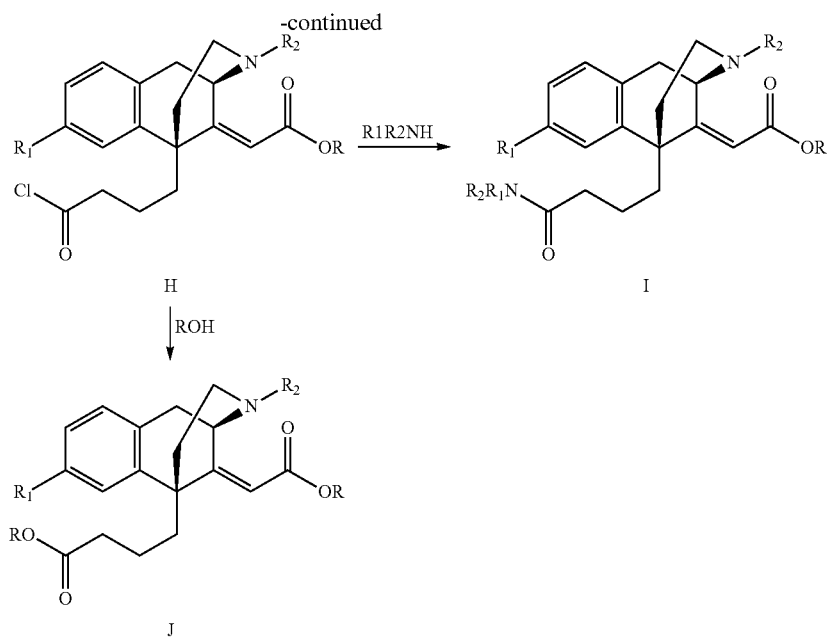

Olefin E can be obtained by treatment of ketone D with a suitable reagent such as the ylide derived from the appropriate phosphonium salt or phosphonate such as methyl diethylphosphonoacetate and a suitable organic base such as NaHMDS in a suitable solvent such as THF. Treatment of olefin E with an acid such as TFA can lead to acetal deprotection and the resulting aldehyde F can be oxidized to the corresponding carboxylic acid G using a suitable oxidizing agent such as sodium chlorite/monobasic sodium phosphate in a suitable solvent such as aqueous ACN. Acid G can be converted to an acid chloride H using a suitable reagent such as oxalyl chloride. Treatment of H with suitable amines or alcohols can yield amides I or esters J, respectively.

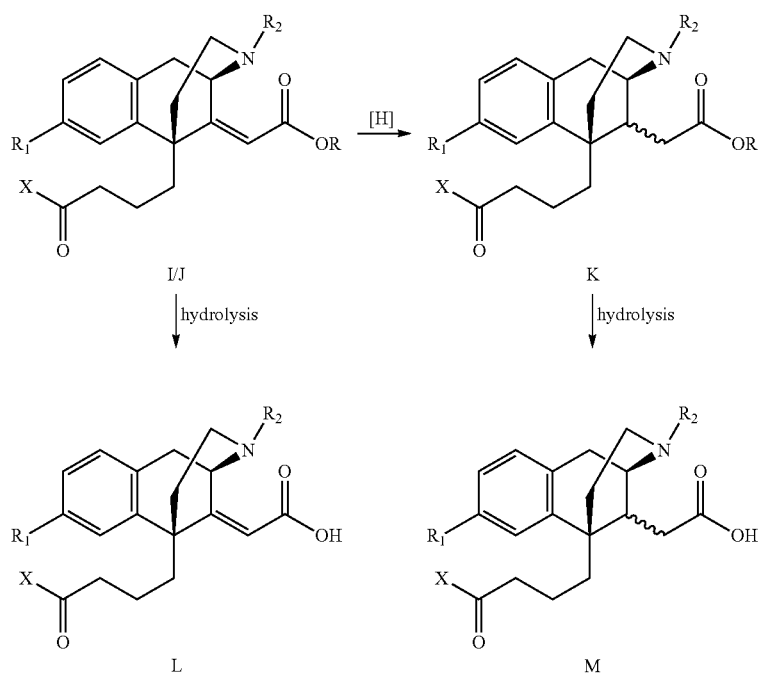

Scheme C

Reduction of the double bond in compounds I and J can be effected using a suitable reducing agent such as hydrogen at a suitable pressure such as 1-3 atm. in the presence of a suitable catalyst such as Palladium on Carbon in a suitable solvent such as MeOH to provide alkane K. Hydrolysis of esters I, J or K using either aqueous acid or base provides compounds L and M, respectively.

Scheme D

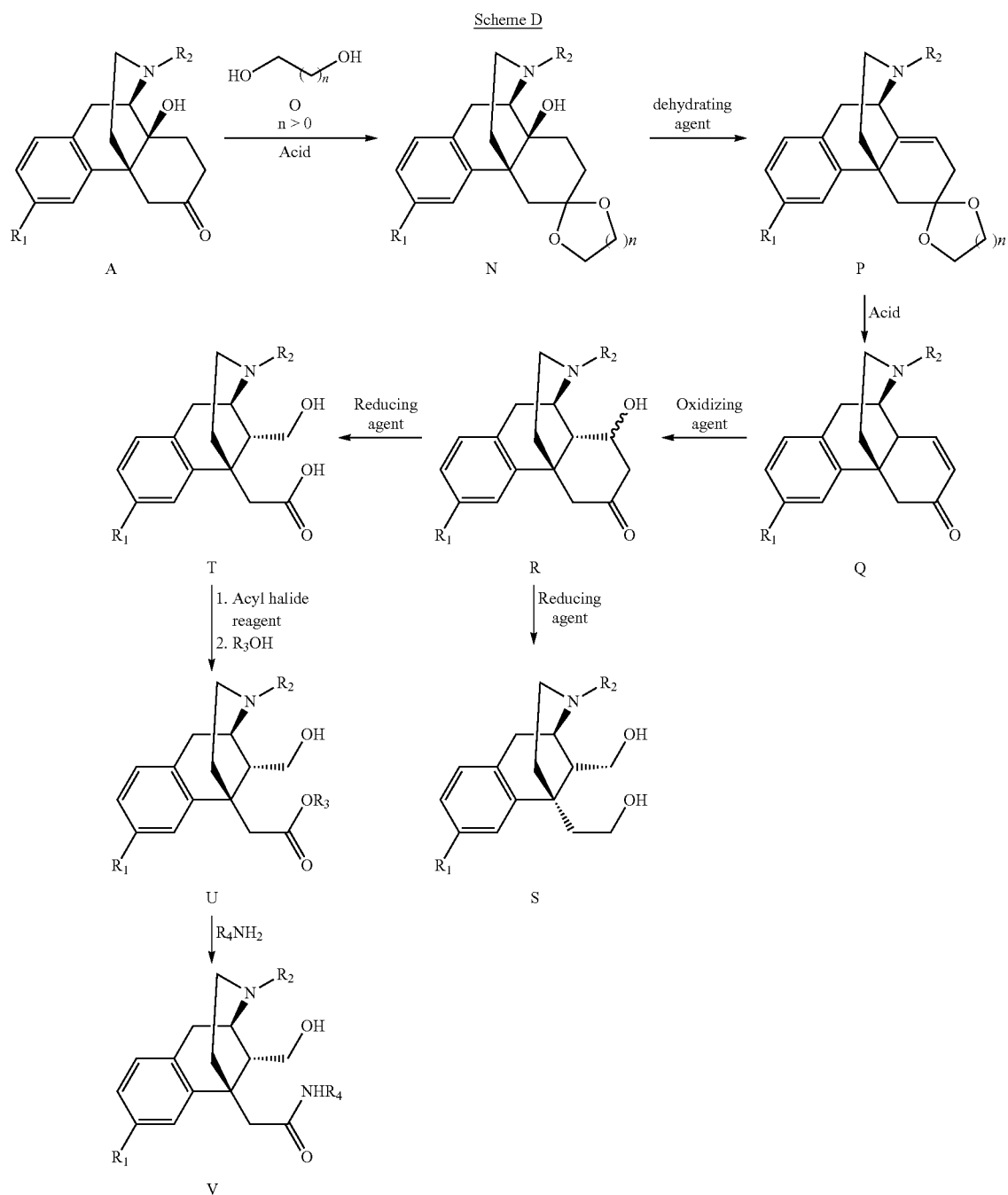

Compound A can be converted to ketal N with a suitable diol O, such as ethylene glycol, in the presence of a suitable acid, such as PTSA, in a suitable solvent, such as toluene, at 130° C. Olefin P can be prepared by treating ketal N with a suitable dehydrating agent such as thionyl chloride, in a suitable solvent, such as pyridine. Olefin P can be converted to enone Q with a suitable acid, such as 20% aq. HCl, at room temperature to 100° C. Enone Q can be converted to lactol S with a suitable oxidizing agent, such as ozone, in the presence of a suitable acid, such as TFA, in a suitable solvent, such as MeOH, at −78° C. to room temperature. Lactol R can be converted to diol S and hydroxy acid T with suitable reducing agents, such as LAH and $NaBH_4$, respectively in a suitable solvent such as THF. Hydroxy ester U can be prepared from hydroxyacid T by activating the carboxylic acid by conversion to an acyl halide using a suitable reagent such as thionyl chloride in a suitable nucleophilic solvent such as MeOH. Hydroxy ester U can be converted to hydroxy amide V with a suitable amine nucleophile such as $NH_3$ in a suitable solvent such as MeOH.

In light of the present disclosure, one of skill in the art would know how to synthesize different stereoisomeric forms (including enantiomers, diastereomers, and other stereoisomeric forms) by using the appropriate reagents and starting materials. For example, to generate an alternate stereoisomeric form in Scheme A, one could use compound A-2 (shown below) instead of compound A as the starting material.

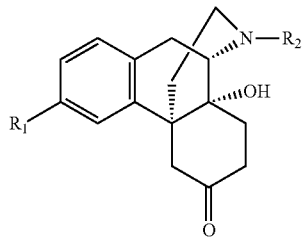

A-2

Testing of Compounds

μ-opioid Receptor Binding Assay Procedures: Radioligand dose-displacement binding assays for μ-opioid receptors used 0.3 nM [$^3$H]-diprenorphine (Perkin Elmer, Shelton, Conn.), with 5 mg membrane protein/well in a final volume of 500 μl binding buffer (10 mM MgCl$_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 2 hr at room temperature. Binding reactions were terminated by rapid filtration onto 96-well Unifilter GF/C filter plates (Perkin Elmer, Shelton, Conn.), presoaked in 0.5% polyethylenimine using a 96-well tissue harvester (Perkin Elmer, Shelton, Conn.) followed by performing three filtration washes with 500 μl of ice-cold binding buffer. Filter plates were subsequently dried at 50° C. for 2-3 hours. BetaScint scintillation cocktail (Perkin Elmer, Shelton, Conn.) was added (50 μl/well), and plates were counted using a Packard Top-Count for 1 min/well. The data were analyzed using the one-site competition curve fitting functions in GraphPad PRISM™ v. 3.0 or higher (San Diego. Calif.), or an in-house function for one-site competition curve-fitting.

μ-opioid Receptor Binding Data: Generally, the lower the Ki value, the more effective the Compounds of the Invention will be at treating or preventing pain or another Condition. Typically, the Compounds of the Invention will have a Ki (nM) of about 1000 or less for binding to μ-opioid receptors. In certain embodiments, the Compounds of the Invention will have a Ki (nM) of about 300 or less for binding to μ-opioid receptors, or about 100 or less, or about 10 or less, or about 1 or less, or about 0.1 or less.

μ-Opioid Receptor Functional Assay Procedures: [$^{35}$S]GTPγS functional assays were conducted using freshly thawed μ-receptor membranes (Perkin Elmer, Shelton, Conn.). Assay reactions were prepared by sequentially adding the following reagents to binding buffer (100 mM NaCl, 10 mM MgCl$_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; Perkin Elmer, Shelton, Conn.). The prepared membrane solution (190 μl/well) was transferred to 96-shallow well polypropylene plates containing 10 μl of 20× concentrated stock solutions of the agonist [D-Ala$^2$, N-methyl-Phe$^4$ Gly-ol$^5$]-enkephalin (DAMGO) prepared in dimethyl sulfoxide (DMSO). Plates were incubated for 30 min at about 25° C. with shaking. Reactions were terminated by rapid filtration onto 96-well Unifilter GF/B filter plates (Perkin Elmer, Shelton, Conn.) using a 96-well tissue harvester (Perkin Elmer, Shelton, Conn.) followed by three filtration washes with 200 μl of ice-cold wash buffer (10 mM NaH$_2$PO$_4$, 10 mM Na$_2$HPO$_4$, pH 7.4). Filter plates were subsequently dried at 50° C. for 2-3 hr, BetaScint scintillation cocktail (Perkin Elmer, Shelton, Conn.) was added (50 μl/well) and plates were counted using a Packard Top-Count for 1 mm/well. Data were analyzed using the sigmoidal dose-response curve fitting functions in GraphPad PRISM™; v. 3.0, or an in-house function for non-linear, sigmoidal dose-response curve-fitting.

μ-Opioid Receptor Functional Data: μ GTP EC$_{50}$ is the concentration of a compound providing 50% of the maximal response for the compound, at a μ-opioid receptor. Compounds of the Invention will typically have a μ GTP EC$_{50}$ (nM) of about 5000 or less. In certain embodiments. Compounds of the Invention will have a μ GTP EC$_{50}$ (nM) of about 2000 or less, or about 1000 or less, or about 100 or less, or about 10 or less, or about 1 or less, or about 0.1 or less.

μ GTP E$_{max}$ (%) is the maximal effect elicited by a compound relative to the effect elicited by DAMGO, a standard μ agonist. Generally, the μ GTP E$_{max}$ (%) value measures the efficacy of a compound to treat or prevent pain or other Conditions. Typically, Compounds of the Invention will have a μ GTP E$_{max}$ (%) of greater than about 10%, or greater than about 20%, or greater than about 50%, or greater than about 65%, or greater than about 75%, or greater than about 85%, or greater than about 100%.

κ-opioid Receptor Binding Assay Procedures: Membranes from recombinant HEK-293 cells expressing the human κ opioid receptor (cloned in house) were prepared by lysing cells in ice cold hypotonic buffer (2.5 mM MgCl$_2$, 50 mM HEPES, pH 7.4) (10 mL/10 cm dish) followed by homogenization with a tissue grinder/Teflon pestle. Membranes were collected by centrifugation at 30,000× g for 15 min at 4° C. and pellets were resuspended in hypotonic buffer to a final concentration of 1-3 mg/mL. Protein concentrations were determined using the BioRad protein assay reagent with bovine serum albumen as standard. Aliquots of κ receptor membranes were stored at –80° C.

Radioligand dose displacement assays used 0.4 nM [$^3$]-U69,593 (GE Healthcare, Piscataway, N.J.; 40 Ci/mmole) with 15 μg membrane protein (recombinant κ opioid receptor expressed in HEK 293 cells; in-house prep) in a final volume of 200 μl binding buffer (5% DMSO, 50 mM Trizma base, pH 7.4). Non-specific binding was determined in the presence of 10 μM unlabeled naloxone or U69,593. All reactions were performed in 96-well polypropylene plates for 1 hr at a temperature of about 25° C. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by five filtration washes with 200 μl ice-cold binding buffer. Filter plates were subsequently dried at 50° C. for 1-2 hours. Fifty μl/well scintillation cocktail (Perkin Elmer, Shelton, Conn.) was added and plates were counted in a Packard Top-Count for 1 min/well. Data were analyzed using the sigmoidal dose-response curve fitting functions in GraphPad PRISM™ v. 3.0, or an in-house function for non-linear, sigmoidal dose-response curve-fitting.

κ-opioid Receptor Binding Data: In certain embodiments, the Compounds of the Invention will have a Ki (nM) for κ receptors of about 10,000 or more (which, for purposes of this invention, is interpreted as having no binding to the κ receptors). Certain Compounds of the Invention will have a Ki (nM) of about 20,000 or less, or about 10,000 or less, or about 5000 or less, or about 1000 or less, or about 500 or less, or about 450 or less, or about 350 or less, or about 200 or less, or about 100 or less, or about 50 or less, or about 10 or less, or about 1 or less, or about 0.1 or less, κ-Opioid Receptor Functional Assay Procedures: Functional [$^{35}$S]GTPγS binding assays were conducted as follows, k opioid receptor membrane solution was prepared by sequentially adding final concentrations of 0.026 μg/μl κ membrane protein (in-house), 10 μg/mL saponin, 3 μM GDP and 0.20 [$^{35}$S]GTPγS to binding buffer (100 mM NaCl, 10 mM MgCl$_2$, 20 mM HEPES, pH 7.4) on ice. The prepared membrane solution (190 μl/well) was transferred to 96-shallow well polypropylene plates containing 10 μl of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates were subsequently dried at 50° C. for 2-3 hours. Fifty μl/well scintillation cocktail (Perkin Elmer, Shelton, Conn.) was added and plates were counted in a Packard Top-Count for 1 min/well. Data were analyzed using the sigmoidal dose-response curve fitting functions in GraphPad PRISM™ v. 3.0, or an in-house function for non-linear, sigmoidal dose-response curve-fitting.

κ-Opioid Receptor Functional Data: κ GTP EC$_{50}$ is the concentration of a compound providing 50% of the maximal response for the compound at a κ receptor. Certain Compounds of the Invention will have a κ GTP EC$_{50}$ (nM) of about 20,000 or less to stimulate κ opioid receptor function. In certain embodiments, Compounds of the Invention will have a κ GTP EC$_{50}$ (nM) of about 10,000 or less, or about 5000 or less, or about 2000 or less, or about 1500 or less, or about 1000 or less, or about 600 or less, or about 100 or less, of about 50 or less, or about 25 or less, or about 10 or less, or about 1 or less, or about 0.1 or less.

κ GTP E$_{max}$ (%) is the maximal effect elicited by a compound relative to the effect elicited by U69,593. Certain Compounds of the Invention will have a κ GTP E$_{max}$ (%) of greater than about 1%, or greater than about 5%, or greater than about 10%, or greater than about 20%, or greater than about 50%, or greater than about 75%, or greater than about 90%, or greater than about 100%.

δ-opioid Receptor Binding Assay Procedures: δ-opioid Receptor Binding Assay Procedures can be conducted as follows. Radioligand dose-displacement assays use 0.3 nM [$^{3}$H]-Naltrindole (Perkin Elmer, Shelton, Conn.; 33.0 Ci/mmole) with 5 μg membrane protein (Perkin Elmer, Shelton, Conn.) in a final volume of 500 μl binding buffer (5 mM MgCl, 5% DMSO, 50 mM Trizma base, pH 7.4). Non-specific binding is determined in the presence of 25 μM unlabeled naloxone. All reactions are performed in 96-deep well polypropylene plates for 1 hr at a temperature of about 25° C. Binding reactions are terminated by rapid filtration onto 96-well Unifilter GF/C filter plates (Perkin Elmer, Shelton, Conn.) presoaked in 0.5% polyethylenimine (Sigma). Harvesting is performed using a 96-well tissue harvester (Perkin Elmer, Shelton, Conn.) followed by five filtration washes with 500 μl ice-cold binding buffer. Filter plates are subsequently dried at 50° C. for 1 -2 hours. Fifty μl/well scintillation cocktail (Perkin Elmer, Shelton, Conn.) is added and plates are counted in a Packard Top-Count for 1 min/well. The data from screening and dose-displacement experiments are analyzed using Microsoft Excel and the curve fitting functions in GraphPad PRISM™, v., 3.0 or higher, respectively, or an in-house function for one-site competition curve-fitting.

δ-opioid Receptor Binding Data. In certain embodiments, the Compounds of the Invention will have a Ki (nM) for δ receptors of about 10,000 or more (which, for the purposes of this invention, is interpreted as having no binding to the δ receptors). Certain Compounds of the Invention will have a Ki (nM) of about 20,000 or less for δ receptors. In one embodiment, the Compounds of the Invention will have a Ki (nM) of about 10,000 or less, or about 9000 or less, or about 7500 or less, or about 6500 or less, or about 5000 or less, or about 3000 or less, or about 2500 or less, or about 1000 or less, or about 500 or less, or about 350 or less, or about 250 or less, or about 100 or less, or about 10 or less.

δ-Opioid Receptor Functional Assay Procedures: Functional [$^{35}$S]GTPγS binding assays are conducted as follows, δ opioid receptor membrane solution is prepared by sequentially adding final concentrations of 0.026 μg/μl δ membrane protein (Perkin Elmer, Shelton, Conn.), 10 μg/mL saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) is transferred to 96-shallow well polypropylene plates containing 10 μl of 20× concentrated stock solutions of agonist prepared in DMSO. Plates are incubated for 30 mm at a temperature of about 25° C. with shaking. Reactions are terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates are subsequently dried at 50° C. for 1-2 hours. Fifty μl/well scintillation cocktail (Perkin Elmer, Shelton, Conn.) is added and plates are counted in a Packard Top-count for 1 min/well.

δ-Opioid Receptor Functional Data: δ GTP EC$_{50}$ is the concentration of a compound providing 50% of the maximal response for the compound at a δ receptor. Certain Compounds of the Invention will have a δ GTP EC$_{50}$ (nM) of about 20,000 or less, or about 10,000 or less, or about 3500 or less, or about 1000 or less, or about 500 or less, or about 100 or less, or about 90 or less, or about 50 or less, or about 25 or less, of about 10 or less.

δ GTP E$_{max}$ (%) is the maximal effect elicited by a compound relative to the effect elicited by met-enkephalin. Certain Compounds of the Invention of the invention will have a δ GTP E$_{max}$ (%) of greater than about 1%, or greater than about 5%, or greater than about 10%, or greater than about 30%, or greater than about 50%, or greater than about 75%, or greater than about 90%, or about 100% or greater.

ORL-1 Receptor Binding Assay Procedure: Membranes from recombinant HEK-293 cells expressing the human opioid receptor-like receptor (ORL-1) (Perkin Elmer, Shelton, Conn.) are prepared by lysing cells in ice-cold hypotonic buffer (2.5 mM MgCl$_2$, 50 mM HEPES, pH 7.4) (10 ml/10 cm dish) followed by homogenization with a tissue grinder/Teflon pestle. Membranes are collected by centrifugation at 30,000×g for 15 min at 4° C. and pellets resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at −80° C.

Radioligand binding assays (screening and dose-displacement) use 0.1 nM [$^{3}$H]-nociceptin (Perkin Elmer, Shelton, Conn.; 87.7 Ci/mmole) with 12 μg membrane protein in a final volume of 500 μl binding buffer (10 mM MgCl$_2$, 1 mM EDTA, 5% DMSO, 50 mM HEPES, pH 7.4). Non-specific binding is determined in the presence of 10 nM unlabeled nociceptin (American Peptide Company). All reactions are performed in 96-deep well polypropylene plates for 1 h at room temperature. Binding reactions are terminated by rapid filtration onto 96-well Unifilter GF/C filter plates (Perkin Elmer, Shelton, Conn.) presoaked in 0.5% polyethylenimine (Sigma). Harvesting is performed using a 96-well tissue harvester (Perkin Elmer, Shelton, Conn.) followed by three filtration washes with 500 µl ice-cold binding buffer. Filter plates are subsequently dried at 50° C. for 2-3 hours. Fifty µl/well scintillation cocktail (Perkin Elmer, Shelton, Conn.) is added and plates are counted in a Packard Top-Count for 1 min/well. The data from screening and dose-displacement experiments are analyzed using Microsoft Excel and the curve fitting functions in GraphPad PRISM™, v. 3.0 or higher, respectively, or an in-house function for one-site competition curve-fitting.

ORL-1 Receptor Binding Data: Certain Compounds of the Invention will have a Ki (nM) of about 1000 or less. In one embodiment, the Compounds of the Invention, will have a Ki (nM) of about 500 or less, or about 300 or less, or about 100 or less, or about 50 or less, or about 20 or less, or about 10 or less, or of about 1 or less, or about 0.1 or less.

ORL-1 Receptor Functional Assay Procedure: Membranes from recombinant HEK-293 cells expressing the human opioid receptor-like (ORL-1) (Perkin Elmer, Shelton, Conn.) are prepared by lysing cells in ice-cold hypotonic buffer (2.5 mM $MgCl_2$, 50 mM HEPES, pH 7.4) (10 ml/10 cm dish) followed by homogenization with a tissue grinder/Teflon pestle. Membranes are collected by centrifugation at 30,000×g for 15 min at 4° C., and pellets resuspended in hypotonic buffer to a final concentration of 1-3 mg/ml. Protein concentrations are determined using the BioRad protein, assay reagent with bovine serum albumen as standard. Aliquots of the ORL-1 receptor membranes are stored at −80° C.

Functional [$^{35}$S]GTPγS binding assays are conducted, as follows. ORL-1 membrane solution is prepared by sequentially adding final concentrations of 0.026 µg/µl ORL-1 membrane protein, 10 µg/ml saponin, 3 µM GDP and 0.20 nM [$^{35}$S]GTPγS to binding buffer (100 mM NaCl, 10 mM $MgCl_2$, 20 mM HEPES, pH 7.4) on ice. The prepared membrane solution (190 µl/well) is transferred to 96-shallow well polypropylene plates containing 10 µl of 20×concentrated stock solutions of agonist/nociceptin prepared in DMSO. Plates are incubated for 30 min at room temperature with shaking. Reactions are terminated by rapid filtration onto 96-well Unifilter GF/B filter plates (Perkin Elmer, Shelton, Conn.) using a 96-well tissue harvester (Packard) and followed by three filtration washes with 200 µl ice-cold binding buffer (10 mM $NaH_2PO_4$, 10 mM: $Na_2HPO_4$, pH 7.4). Filter plates are subsequently dried at 50° C. for 2-3 hours. Fifty µl/well scintillation cocktail (Perkin Elmer, Shelton, Conn.) is added and plates are counted in a Packard Top-Count for 1 min/well. Data are analyzed using the sigmoidal dose-response curve fitting functions in GraphPad PRISM v. 3.0 or higher, or an in-house function for non-linear, sigmoidal dose-response curve-fitting.

ORL-1 Receptor Functional Data: ORL-1 GTP $EC_{50}$ is the concentration of a compound providing 50% of the maximal response for the compound at an ORL-1 receptor. In certain embodiments, the Compounds of the Invention that have a high binding affinity (i.e. low $K_i$ value) will have an ORL-1 GTP $EC_{50}$ (nM) of greater than about 10,000 (i.e. will not stimulate at therapeutic concentrations). In certain embodiments, Compounds of the Invention will have an ORL-1 GTP $EC_{50}$ (nM) of about 20,000 or less, or about 10,000 or less, or about 5000 or less, or about 1000 or less, or about 100 or less, or about 10 or less, or about 1 or less, or about 0.1 or less.

ORL-1 GTP $E_{max}$% is the maximal effect elicited by a compound relative to the effect elicited by nociceptin, a standard ORL-1 agonist. In certain embodiments, Compounds of the Invention will have an ORL-1 GTP $E_{max}$ of less than 10% (which, for the purposes of this invention, is interpreted as having antagonist activity at ORL-1 receptors). Certain Compounds of the Invention will have an ORL-1 GTP $E_{max}$ (%) of greater than 1%, or greater than 5%, or greater than 10%, or greater than 20%, or greater than 50%, or greater than 75%, or greater than 88%, or greater than 100%.

In Vivo Assays for Prevention Treatment of Pain

Test Animals: Each experiment uses rats weighing between 200-260 g at the start of the experiment. The rats are group-housed and have free access to food and water at all times, except prior to oral administration of a Compound of the Invention when food is removed for about 16 hours before dosing. A control group acts as a comparison to rats treated with a Compound of the Invention. The control group is administered the carrier for the Compound of the Invention. The volume of carrier administered to the control group is the same as the volume of carrier and Compound of the Invention administered to the test group.

Acute Pain: To assess the actions of a Compound of the Invention for the treatment or prevention of acute pain, the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset, of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Compound of the Invention. Data are expressed as tail flick latency(s) and the percentage of the maximal possible effect (% MPE), i.e., 20 seconds, is calculated as follows:

$$\% \ MPE = \frac{[(\text{post administration latency}) - (\text{pre-administration latency})]}{(20 \ s - \text{pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

To assess the actions of a Compound of the Invention for the treatment or prevention of acute pain, the rat hot plate test can also be used. Rats are tested using a hot plate apparatus consisting of a clear plexiglass cylinder with a heated metal floor maintained at a temperature of 48-52° C. (Model 7280, commercially available from Ugo Basile of Italy). A rat is placed into the cylinder on the hot plate apparatus for a maximum duration of 30 s, or until it exhibits a nocifensive behavior (behavioral endpoint), at which time it is removed from the hot plate, and response latency recorded. Hot plate latencies are measured immediately before (pre-treatment) and 1, 3, and 5 hours following administration of a Compound of the Invention. The nocifensive behavioral endpoint is defined as any of the following: 1) paw withdrawal, either as a sustained lift or with shaking or licking; 2) alternating foot lifting; 3) escape or attempted escape from the testing device; or 4) vocalization. Data are expressed as response latency(s) and the percentage of the maximal possible effect is calculated as described above for the tail flick test. The hot plate test is described, in G. Woolfe and. A. D. Macdonald, *J. Pharmacol. Exp. Ther.* 80:300-307 (1944).

Inflammatory Pain: To assess the actions of a Compound of the Invention for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *NaunynSchmiedeberg's Archives of Pharmacol.* 342:666-670 (1990)). The left hind paw of each animal is administered a 50 µL intraplantar injection of 50% FCA. Prior to injection of FCA (baseline) and 24 hours post injection, the animal is assessed for response to noxious mechanical stimuli by determining the PWT, as described below. Rats are then administered a single injection of a range of doses, such as for example 1, 3, or 10 mg/kg, of either a Compound of the Invention; 30 mg/kg of a control drug selected from Celebrex, indomethacin or naproxen; or carrier. Responses to noxious mechanical stimuli are determined 1, 3, 5 and 24 hours post administration. Percentage reversal of hyperalgesia for each animal is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

Neuropathic Pain: To assess the actions of a Compound of the Invention for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜0 curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration. Percentage reversal of neuropathic hyperalgesia is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia, and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the Invention. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50 (3):355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The rat's paw is placed on a small platform, and weight is applied in a graded manner up to a maximum of 250 grams. The endpoint is taken as the weight at which the paw is completely withdrawn. PWT is determined once for each rat at each time point and either only the affected (ipsilateral; same side as the injury) rear paw is tested, or both the ipsilateral and contralateral (non-injured; opposite to the injury) rear paw are tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32 (1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the affected (ipsilateral) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period, of 4-8 seconds or until a nociceptive withdrawal behavior is observed. Flinching, paw withdrawal or licking of the paw are considered nociceptive behavioral responses.

Assessment of Respiratory Depression: To assess respiratory depression, rats can be prepared by implanting a femoral artery cannula via which blood samples are taken. Blood samples are taken prior to drug administration, then 1, 3, 5 and 24 hours post-treatment. Blood samples are processed using an arterial blood gas analyzer (e.g., IDEXX VetStat with Respiratory/Blood Gas test cartridges). Comparable devices are a standard tool for blood gas analysis (e.g., D. Torbati et al., 2000 *Intensive Care Med*. (26) 585-591).

Assessment of Gastric Motility: Animals are treated with vehicle, reference compound or test article by oral gavage at a volume of 10 mL/kg. At one hour post-dose, all animals are treated with charcoal meal solution (5% non-activated charcoal powder in a solution of 1% carboxymethylcellulose in water) at a volume of 10 mL/kg. At two hours post-dose (one hour post-charcoal), animals are sacrificed by carbon dioxide inhalation or isoflurane overdose and the transit of charcoal meal identified. The stomach and small intestine are removed carefully and each placed on a saline-soaked absorbent surface. The distance between the pylorus and the furthest progression of charcoal meal is measured and compared to the distance between the pylorus and the ileocecal junction. The charcoal meal transit is expressed as a percentage of small intestinal length traveled.

Pharmaceutical Compositions

Due to their activity, the Compounds of the Invention are advantageously useful in human and veterinary medicine. As described above, the Compounds of the Invention are useful for treating or preventing a Condition in an animal (a human patient or non-human subject) in need thereof. The Compounds of the Invention can be administered to any animal requiring modulation of the opioid and/or ORL-1 receptors.

When administered to an animal, a Compound of the Invention can be administered as a component of a pharmaceutical composition that comprises a pharmaceutically acceptable carrier or excipient. A Compound of the Invention can be administered by any appropriate route, as determined by the medical practitioner. Methods of administration may include intradermal, intramuscular, intraperitoneal, parenteral, intravenous, subcutaneous, intranasal, epidural, oral, sublingual, intracerebral, intravaginal, transdermal, transmucosal, rectal, by inhalation, or topical (particularly to the ears, nose, eyes, or skin). Delivery can be either local or systemic. In certain embodiments, administration will result in the release of a Compound of the Invention into the bloodstream.

Pharmaceutical compositions of the invention can take the form of solutions, suspensions, emulsions, tablets, pills, pellets, multi-particulates, capsules, capsules containing liquids, capsules containing powders, capsules containing multi-particulates, lozenges, immediate-release formulations, sustained-release formulations, controlled-release formulations, suppositories, aerosols, sprays, or any other form suitable for use. In one embodiment, the composition is in the form of a capsule (see, e.g., U.S. Pat. No. 5,698,155).

Pharmaceutical compositions of the invention preferably comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Compound of the Invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium, chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986). Other examples of suitable pharmaceutical excipients are described in *Remington's Pharmaceutical Sciences* 1447-1676 (Alfonso R. Gennaro ed., 19th ed. 1995), incorporated herein by reference.

In certain embodiments, the Compounds of the Invention are formulated for oral administration. A Compound of the Invention to be orally delivered can be in the form of tablets, capsules, gelcaps, caplets, lozenges, aqueous or oily solutions, suspensions, granules, powders, emulsions, syrups, or elixirs, for example. When a Compound of the Invention is incorporated into oral tablets, such tablets can be compressed, tablet triturates, enteric-coated, sugar-coated, film-coated, multiply compressed or multiply layered.

An orally administered Compound of the Invention can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., $16^{th}$ ed., Mack Publishing, Easton, Pa. 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are described in *Pharmaceutical Dosage Forms: Disperse Systems*, (Lieberman, Rieger and Banker, eds.) published by Marcel Dekker, Inc.

When a Compound of the Invention is formulated for parenteral administration by infection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When a Compound of the Invention is to be injected parenterally, it can be, e.g., in the form of an isotonic sterile solution. A Compound of the Invention can also be in the form of a powder for reconstitution as an injectable formulation.

In certain embodiments, a Compound of the Invention is formulated into a pharmaceutical composition for intravenous administration. Typically, such compositions comprise sterile isotonic aqueous buffer. Where necessary, the compositions can also include a solubilizing agent. A Compound of the Invention for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of the Invention is to be administered by infusion, it can be dispensed, for example, with an infusion bottle containing sterile pharmaceutical grade water or saline. Where a Compound of the Invention is administered by injection, an ampule of sterile water for injection or saline can be provided so that the ingredients can be mixed prior to administration.

When a Compound of the Invention is to be administered by inhalation, it can be formulated into a dry aerosol, or an aqueous or partially aqueous solution.

In another embodiment, a Compound of the Invention can be delivered in a vesicle, in particular a liposome (see Langer, *Science* 249:1527-1533 (1990); and Treat et al., *Liposomes in the Therapy of Infectious Disease and Cancer* 317-327 and 353-365 (1989)).

In certain embodiments, a Compound of the Invention is administered locally. This can be achieved, for example, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, a Compound of the Invention can be delivered in an immediate release form. In other embodiments, a Compound of the Invention can be delivered in a controlled-release system or sustained-release system. Controlled- or sustained-release pharmaceutical compositions can have a common goal of improving drug therapy over the results achieved by their non-controlled or non-sustained-release counterparts. In one embodiment, a controlled- or sustained-release composition comprises a minimal amount of a Compound of the Invention to treat or prevent the Condition (or a symptom thereof) in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Compound of the Invention, and can thus reduce the occurrence of adverse side effects.

Controlled- or sustained-release compositions can initially release an amount of a Compound of the Invention that promptly produces the desired therapeutic or prophylactic effect, and gradually and continually release other amounts of the Compound of the Invention to maintain a level of therapeutic or prophylactic effect over an extended period of time. To maintain a constant level of the Compound of the invention in the body, the Compound of the Invention can be released from the dosage form at a rate that will replace the amount of Compound of the Invention being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

Controlled-release and sustained-release means for use according to the present invention may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. See also Goodson, "Dental Applications" (pp. 115-138) in *Medical Applications of Controlled Release, Vol, 2, Applications and Evaluation*, R. S. Langer and D. L. Wise eds., CRC Press (1984). Other controlled- or sustained-release systems that are discussed in the review by Langer, *Science* 249:1527-1533 (1990) can be selected for use according to the present invention. In one embodiment, a pump can be used (Langer, *Science* 249; 1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of a Compound of the Invention, e.g., the spinal column, brain, or gastrointestinal tract, thus requiring only a fraction of the systemic dose.

When in tablet or pill form, a pharmaceutical composition of the invention can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

Pharmaceutical compositions of the invention include single unit dosage forms suitable for oral administration such as, but not limited to, tablets, capsules, gelcaps, and caplets that are adapted for controlled- or sustained-release.

The amount of the Compound of the Invention that is effective for the treatment or prevention of a condition can be determined by standard clinical techniques. In addition, in vitro and/or in vivo assays can optionally be employed to help identify optimal dosage ranges. The precise dose to be employed will also depend on, e.g., the route of administration and the extent of the Condition to be treated, and can be decided according to the judgment of a practitioner and/or each animal's circumstances. Variations in dosing may occur depending upon typical factors such as the weight, age, gender and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts can range from about 0.01 mg/kg of body weight to about 3000 mg/kg of body weight of the animal per day, although they are typically from about 0.01 mg/kg of body weight to about 2500 mg/kg of body weight of the animal per day or from about 0.01 mg/kg of body weight to about 1000 mg/kg of body weight of the animal per day. In one embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Compound of the Invention, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated. The effective dosage amounts described herein refer to total amounts administered; that is, if more than one Compound of the Invention is administered, the effective dosage amounts correspond to the total amount administered.

Where a cell capable of expressing ORL-1 receptors is contacted with a Compound of the Invention in vitro, the amount effective for inhibiting or activating the ORL-1 receptor function in a cell will typically range from about $10^{-12}$ mol/L to about $10^{-4}$ mol/L, or from about $10^{-2}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the compound in a pharmaceutically acceptable carrier or excipient. In one embodiment, the volume of solution or suspension comprising the Compound of the Invention will be from about 0.01 μL to about 1 mL. In another embodiment, the volume of solution or suspension will be about 200 μL.

Where a cell capable of expressing μ-opioid receptors is contacted with a Compound of the Invention in vitro, the amount effective for Inhibiting or activating the μ-opioid receptor function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 μL to about 1 mL. In another embodiment, the volume of solution or suspension will be about 200 μL.

Where a cell capable of expressing δ-opioid receptors is contacted with a Compound of the Invention in vitro, the amount effective for inhibiting or activating the δ-opioid receptor function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 μL to about 1 mL. In another embodiment, the volume of solution or suspension will be about 200 μL.

Where a cell capable of expressing κ-opioid receptors is contacted with a Compound of the Invention in vitro, the amount effective for inhibiting or activating the κ-opioid receptor function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 μL to about 1 mL. In another embodiment, the volume of solution or suspension will be about 200 μL.

The Compounds of the Invention can be assayed in vitro or in vivo for the desired therapeutic or prophylactic activity prior to use in humans. Animal model systems can be used to demonstrate safety and efficacy. Certain Compounds of the Invention will have an $ED_{50}$ for treating inflammatory pain ranging from about 0.5 mg/kg to about 20 mg/kg. Certain Compounds of the Invention will produce significant analgesia and/or anti-hyperalgesia at doses that do not induce respiratory depression. In contrast, oxygen tension, oxygen saturation and pH are significantly decreased, while carbon dioxide is significantly increased, in blood samples from rats given effective doses of conventional opioids, such as morphine.

According to the invention, methods for treating or preventing a Condition in an animal in need thereof can further comprise co-administering to the animal an effective amount of a second therapeutic agent in addition to a Compound of the Invention (i.e., a first therapeutic agent). An effective amount of the second therapeutic agent will be known or determinable by a medical practitioner in view of this disclosure and published clinical studies. In one embodiment of the invention, where a second therapeutic agent is administered to an animal for treatment of a Condition (e.g., pain), the minimal effective amount of the Compound of the Invention (i.e., the first therapeutic agent) will be less than its minimal effective amount would be in circumstances where the second therapeutic agent is not administered. In this embodiment, the Compound of the Invention and the second therapeutic agent can act either additively or synergistically to treat or prevent a Condition. Alternatively, the second therapeutic agent may be used to treat or prevent a disorder that is different from the Condition for which the first therapeutic agent is being administered, and which disorder may or may not be a Condition as defined hereinabove. In one embodiment, a Compound of the Invention is administered concurrently with a second therapeutic agent as a single composition comprising an effective amount of a Compound of the Invention and an effective amount of the second therapeutic agent. Alternatively, a composition comprising an effective amount of a Compound of the Invention and a second composition comprising an effective amount of the second therapeutic agent are concurrently administered. In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the Compound of the Invention exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-II inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for treating, preventing or inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Paul A. Insel, *Analgesic-Antipyretic and Anti-inflammatory Agents and Drugs Employed in the Treatment of Gout, in Goodman & Gilman's The Pharmacological Basis of Therapeutics* 617-57 (Perry B. Molinhoff and Raymond W. Ruddon eds., $9^{th}$ ed 1996); and Glen R. Hanson, *Analgesic, Antipyretic and Anti-Inflammatory Drugs in Remington: The Science and Practice of Pharmacy Vol IA* 1196-1221 (A. R. Gennaro ed. $19^{th}$ ed. 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol trazodone, zolmitriptan, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful Ca$^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexiline, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flurmazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital and thiopental; propanediol carbamates, such as meprobamate and tybamate; a pharmaceutically acceptable derivative thereof; or any mixture thereof.

Examples of useful therapeutic agents for treating or preventing diarrhea include, but are not limited to, diphenoxylate, loperamide, a pharmaceutically acceptable derivative thereof, or any mixture thereof.

Examples of useful therapeutic agents for treating or preventing epilepsy include, but are not limited to, carbamazepine, ethosuximide, gabapentin, lamotrigine, phenobarbital, phenytoin, primidone, valproic acid, trimethadione, benzodiazepines, γ vinyl GABA, acetazolamide, felbamate, a pharmaceutically acceptable derivative thereof or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof or any mixture thereof.

Examples of non-steroidal anti-inflammatory agents, 5-lipoxygenase inhibitors, anti-emetics, β adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A composition of the invention is prepared by a method comprising admixing a Compound of the Invention (or a pharmaceutically acceptable salt or solvate thereof) with a pharmaceutically acceptable carrier or excipient. Admixing can be accomplished using methods known for admixing a compound (or derivative) and a pharmaceutically acceptable carrier or excipient. In one embodiment, the Compound of the Invention (or pharmaceutically acceptable salt or solvate thereof) is present in the composition in an effective amount.

EXAMPLES

Example 1

4-((2R,6R,11R)-11-(carboxymethyl)-3-(cyclopropylmethyl)-8-hydroxy-1,2,3,4,5,6-hexahydro-2,6-methanobenzo[d]azocin-6-yl)butanoic acid (10)

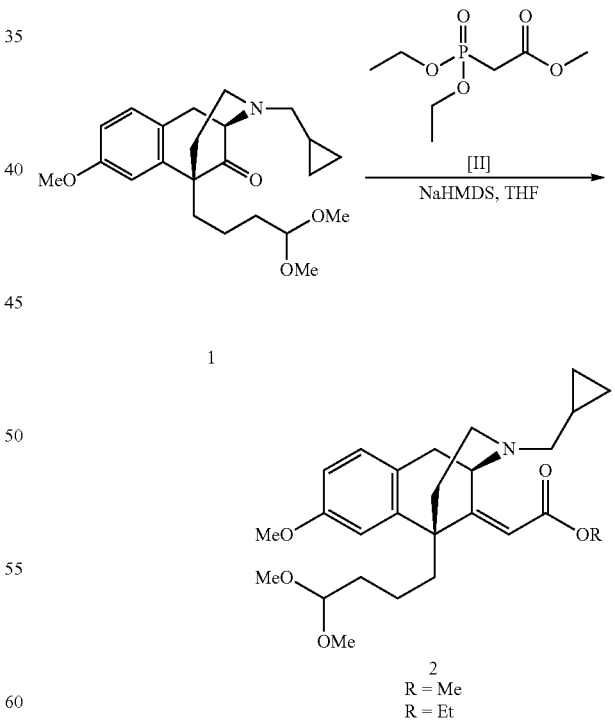

NaHMDS (1M in THF, 1.935 mL, 1.935 mmol) was added at −78° C. to methyl diethylphosphonoacetate (0.284 mL, 1.548 mmol) in 1 mL THF and the solution, was stirred at −78° C. for 10 mm. Compound 1 (0.500 g, 1.290 mmol) in 2 mL THF was added and the solution stirred at −78° C. to RT for 18.5 h then at 60° C. for 3 d 17 h. An additional aliquot of methyl diethylphosphonoacetate (0.284 mL, 1.548 mmol) in 1 mL THF was mixed at 0° C. for 5 min then added to the reaction mixture, after which the solution was heated at reflux for 7 h. The reaction mixture was concentrated and purified by MPLC (0-50% acetone/hexanes, 12 g) to yield compound 2 as a yellow oil. Compound 2 was carried on as a mixture of the methyl and ethyl esters.

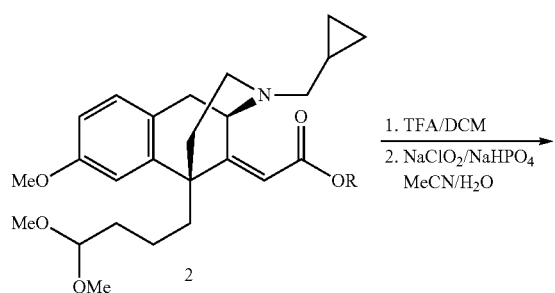

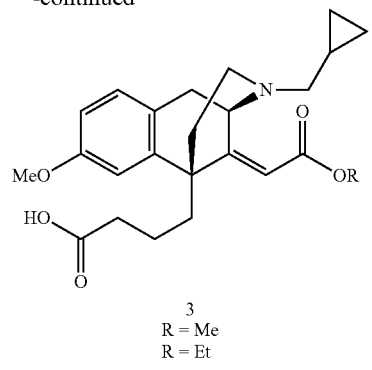

TFA (4 mL) was added to compound 2 (360 mg, ~0.81 mmol) and the solution was stirred for 19 h at RT. The solution was concentrated and 4 mL ACN was added. A solution of sodium chlorite (220 mg, 2.44 mmol) and monobasic sodium phosphate (336 mg, 2.44 mmol) in 4 mL water was added dropwise at 0° C. and the solution stirred at 0° C. to RT for 90 min. The reaction mixture was concentrated and purified by MPLC (0-15% MeOH/DCM, 12 g) to yield compound 3 as a mixture of the methyl and ethyl esters.

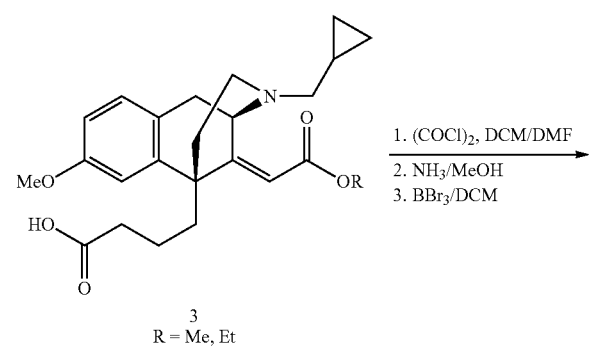

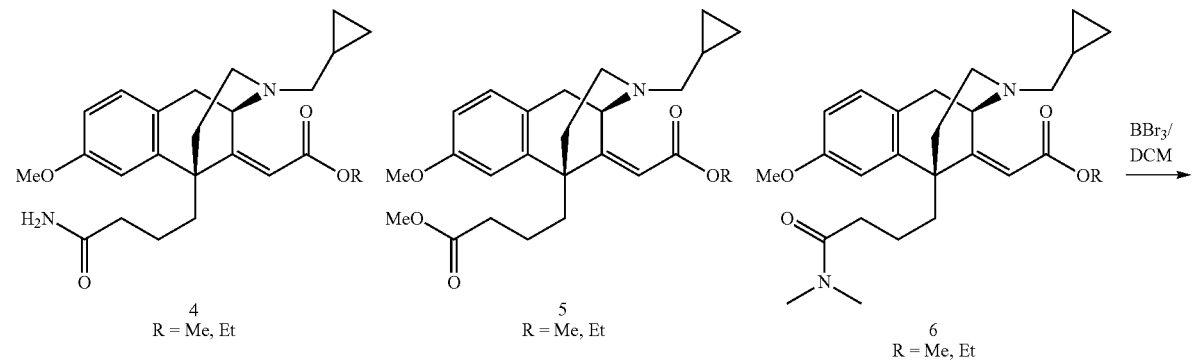

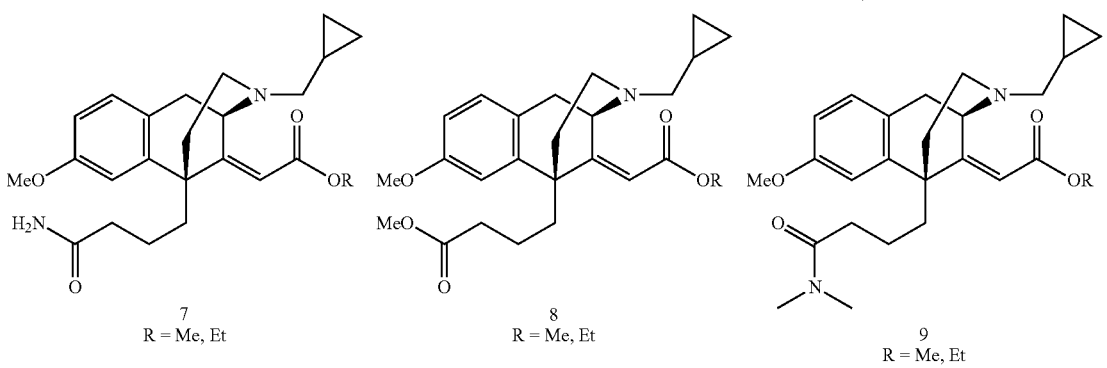

One drop of DMF was added to a solution of compound 3 (0.310 g, 0.750 mmol) and oxalyl chloride (0.131 mL, 1.499 mmol) in 8 mL DCM. The solution was stirred at RT for 20 mm then concentrated. A 7 M solution of ammonia in MeOH (7.50 mL, 52.5 mmol) was added and the solution was stirred at RT for 1 h. An additional aliquot of 7 M ammonia in MeOH (7.50 mL, 52.5 mmol) was added and the solution stirred for an additional 15 h. The solution was concentrated and 15 mL of DCM and 8 equivalents of oxalyl chloride were added. One drop of DMF was added and the solution was stirred at RT for 25 mm, after which 20 mL of a 7M solution of ammonia in MeOH was added. The reaction mixture was stirred at RT for 1 h, DCM was added, the solution washed with saturated aqueous $NaHCO_3$, dried with $Na_2SO_4$, and concentrated. Purification by MPLC (0-15% MeOH/DCM, 4 g) yielded compounds 4, 5, and 6 as mixtures of their methyl and ethyl esters. DCM (2 mL) was added to compounds 4, 5, and 6. A 1 M solution of boron tribromide in DCM (~3 equivalents) was added at 0° C. and the solution was stirred for 75 min at 0° C. The reactions were each quenched with MeOH (approx 2 mL) and concentrated. Compounds 7, 8, and 9 were carried on without purification as a mixture of methyl and ethyl esters.

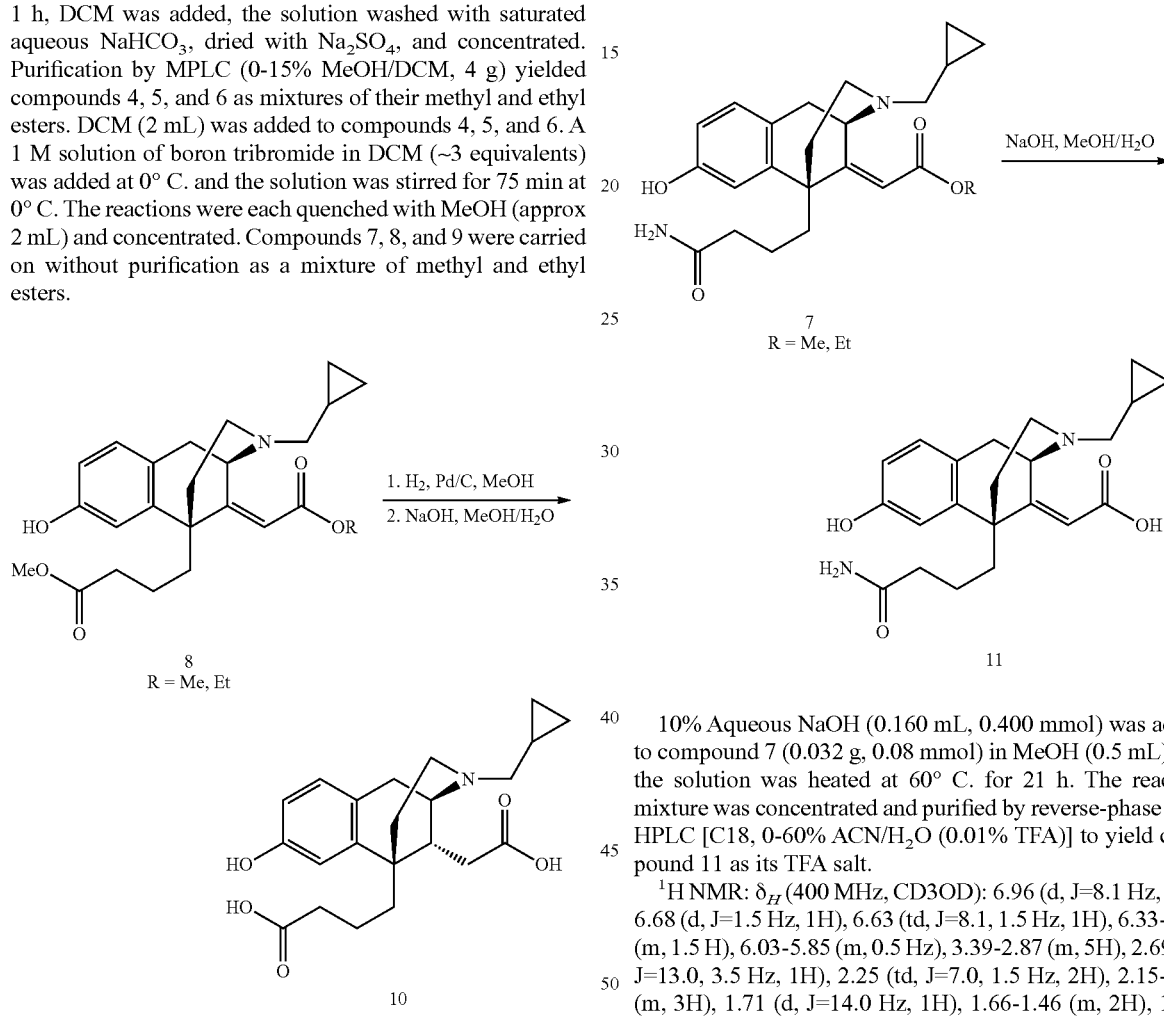

MeOH (5 mL) was added to compound 8 (0.041 g, 0.1 mmol) and the solution run with the Pd/C cartridge on the H-Cube [ThalesNano, model HC-2.SS] at 40° C. and 60 bar in a recirculating fashion at 1 mL/min. After 1 h the heat was increased to 60° C. and after 3 h the flow rate dropped to 0.5 mL/min. The reaction was run in a recirculating fashion for 3 d 19 h and concentrated. MeOH (1 mL) and 10% aqueous NaOH (0.400 mL, 1.000 mmol) were added and the reaction heated at 60° C. for 5 h. The solution was concentrated and purified by reverse-phase prep HPLC [C18, 0-60% ACN/$H_2O$ (0.01% TFA)] to yield compound 10 as its TFA salt.

$^1$H NMR: $\delta_H$ (400 MHz, $CD_3OD$); 6.96 (d, J=8.3 Hz, 1H), 6.69 (d, J=2.4 Hz, 1H), 6.60 (dd, J=8.3, 2.4 Hz, 1H), 4.13-4.07 (m, 1H), 3.34-2.91 (m, 5H), 2.68-2.58 (m, 2H), 2.54 (dd, J=16.8, 3.5 Hz, 1H), 2.42-2.33 (m, 2H), 2.28 (td, J=14.0, 4.5 Hz, 1H), 2.01-1.82 (m, 2H), 1.79-1.59 (m, 3H), 1.38 (d, J=14.0 Hz, 1H), 1.07-0.94 (m, 1H), 0.72-0.63 (m, 2H), 0.39-0.33 (m, 2H).

LC/MS, m/z=388 [M+H]$^+$ (Calc: 387).

Example 2

(Z)-2-((2R,6S)-6-(4-amino-4-oxobutyl)-3-(cyclopropylmethyl)-8-hydroxy-1,2,3,4,5,6-hexahydro-2,6-methanobenzo[d]azocin-11-ylidene)acetic acid (11)

10% Aqueous NaOH (0.160 mL, 0.400 mmol) was added to compound 7 (0.032 g, 0.08 mmol) in MeOH (0.5 mL) and the solution was heated at 60° C. for 21 h. The reaction mixture was concentrated and purified by reverse-phase prep HPLC [C18, 0-60% ACN/$H_2O$ (0.01% TFA)] to yield compound 11 as its TFA salt.

$^1$H NMR: $\delta_H$ (400 MHz, CD3OD): 6.96 (d, J=8.1 Hz, 1H), 6.68 (d, J=1.5 Hz, 1H), 6.63 (td, J=8.1, 1.5 Hz, 1H), 6.33-6.17 (m, 1.5 H), 6.03-5.85 (m, 0.5 Hz), 3.39-2.87 (m, 5H), 2.69 (td, J=13.0, 3.5 Hz, 1H), 2.25 (td, J=7.0, 1.5 Hz, 2H), 2.15-1.89 (m, 3H), 1.71 (d, J=14.0 Hz, 1H), 1.66-1.46 (m, 2H), 1.11-0.97 (m, 1H), 0.76-0.56 (m, 2H), 0.45-0.28 (m, 2H).

LC/MS, m/z=385 [M+H]$^+$ (Calc: 384).

In a similar manner, (Z)-2-((2R,6S)-3-(cyclopropylmethyl)-6-(4-dimethylamino)-4-oxobutyl)-8-hydroxy-1,2,3,4,5,6-hexahydro-2,6-methanobenzo[d]azocin-11-ylidene)acetic acid (12) was prepared by saponifying compound 9. Purification by reverse-phase prep HPLC [C18, 0-60% ACN/$H_2O$ (0.01% TFA)] gave compound 12 as its TFA salt.

$^1$H NMR: $\delta_H$ (400 MHz, $CD_3OD$): 6.97 (d, J=8.1 Hz, 1H), 6.71 (d, J=1.8 Hz, 1H), 6.63 (td, 8.1, 1.8 Hz, 1H), 6.38-6.19 (m, 1.5H), 6.05-5.85 (m, 0.5H), 3.39-3.02 (m, 2H), 2.99 (s, 3H), 2.96-2.88 (m, 1H), 2.87 (s, 3H), 2.70 (td, J=12.9, 3.0 Hz, 1H), 2.43 (td, J=6.7, 1.9 Hz, 2H), 2.17-1.89 (m, 3H), 1.71 (d, J=13.8 Hz, 1H), 1.65-1.44 (m, 2H), 1.13-0.96 (m, 1H), 0.78-0.54 (m, 2H), 0.46-0.29 (m, 2H).

LC/MS, m/z=413 [M+H]$^+$ (Calc: 412).

In a similar manner, 4-((2R,6S,Z)-11-(carboxymethylene)-3-(cyclopropylmethyl)-8-hydroxy-1,2,3,4,5,6-hexahydro-2,6-methanobenzo[d]azocin-6-yl)butanoic acid (13) was prepared by saponifying compound 8. Purification by reverse-phase prep HPLC [C18, 0-60% ACN/H$_2$O (0.01% TFA)] to yield compound 13 as its TFA salt.

$^1$H NMR: $\delta_H$ (400 MHz, CD$_3$OD): 6.97 (d, J=8.3 Hz, 1H), 6.69 (d, J=2.2 Hz, 1H), 6.64 (td, J=8.3, 2.2 Hz, 1H), 6.37-6.17 (m, 1.5H), 6.05-5.85 (m, 0.5H), 3.40-2.84 (m, 5H), 2.69 (td, J=13.0, 2.9 Hz, 1H), 2.35 (q, J=7.0 Hz, 2H), 2.17-1.89 (m, 3H), 1.72 (d, J=13.1 Hz, 1H), 1.62-1.47 (m, 2H), 1.11-0.93 (m, 1H), 0.76-0.56 (m, 2H), 0.43-0.28 (m, 2H).

LC/MS, m/z=386 [M+H]$^+$ (Calc: 385).

Example 3

2-((2R,6S,11R)-3-(cyclopropylmethyl)-11-(hydroxymethyl)-8-methoxy-1,2,3,4,5,6-hexahydro-2,6-methanobenzo[d]azocin-6-yl)ethanol (19) and 2-((2R,6S,11R)-3-(cyclopropylmethyl)-11-(hydroxymethyl)-8-methoxy-1,2,3,4,5,6-hexahydro-2,6-methanobenzo[d]azocin-6-yl)acetamide (22)

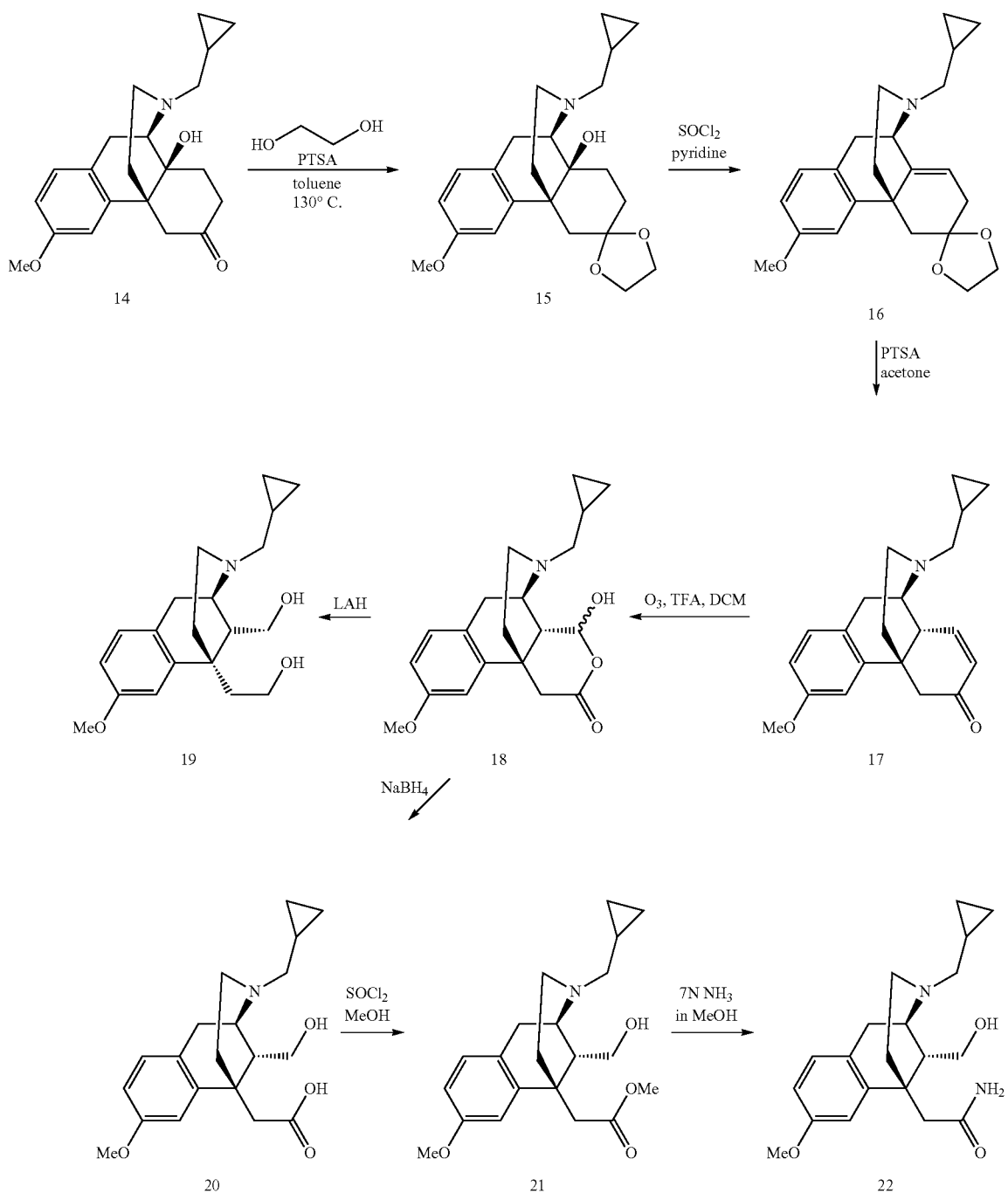

Ethylene glycol (80 mL, 1,523 mmol, 20 eq) and PTSA (14.5 g, 76 mmol, 1.0 eq) were added to a solution of ketone 14 (26 g, 76 mmol, 1.0 eq) in toluene (400 mL). A Dean-Stark apparatus was installed and the mixture was heated to reflux for 3 d. The mixture was cooled to RT. Solid $K_2CO_3$ (10 g) was added and then saturated aqueous $NaHCO_3$ was added and the pH adjusted to 9-10. The layers were separated. The aqueous layer was extracted with DCM and the combined organic layers were dried over $MgSO_4$. The concentrated crude oil was purified by flash chromatography ($SiO_2$, 0-60%, acetone/hexanes) to obtain a yellow sticky foam. 21.5 g (73.2% yield) of compound 15 was obtained.

$^1$H NMR: $\delta_H$ (400 MHz, $CD_3OD$): 6.80 (d, J=8.5 Hz, 1H), 6.69 (d, J=2.4 Hz, 1H), 6.51 (dd, J=8.3, 2.4 Hz, 1H), 3.81-3.75 (m, 1H), 3.75-3.67 (m, 1H), 3.67-3.60 (m, 1H), 3.60-3.55 (m, 4H), 2.89 (d, J=18.1 Hz, 2H), 2.65 (dd, J=18.8, 5.7 Hz, 1H), 2.45-2.15 (m, 4H), 2.01-1.84 (m, 4H), 1.62 (dt, J=4.8, 18.8 Hz, 1H), 1.32 (t, J=12.9 Hz, 2H), 0.92 (d, J=9.8 Hz, 1H), 0.77-0.65 (m, 1H), 0.41-0.31 (m, 2H), 0.05--0.05 (m, 2H).

L-C/MS, m/z=385.2 [M+H]$^+$ (Calc: 385.50).

Thionyl chloride (622 μL, 8.56 mmol, 6.0 eq) was added to a solution of alcohol 15 (550 mg, 1.427 mmol, 1.0 eq) in pyridine (20 mL) at 0° C. The cooling bath was removed and the mixture was stirred for 1.6 h. Pyridine was removed under vacuum and DCM and water were added. The pH was adjusted to 9-10 with solid $K_2CO_3$ and the layers were separated. The aqueous layer was extracted with DCM and the combined organic layers were dried over $MgSO_4$. The concentrated crude oil was purified by flash chromatography ($SiO_2$, 0-100%, acetone/hexanes) to obtain a light brown sticky foam, 253 mg (48.3% yield) of compound 16 was obtained.

$^1$H NMR: $\delta_H$ (400 MHz, $CD_3OD$): 6.81 (d, J=8.3 Hz, 1H), 6.57-6.51 (m, 2H), 5.42 (dd, J=4.8, 3.0 Hz, 1H), 3.91-3.85 (m, 1H), 3.83-3.66 (m, 3H), 3.58 (s, 3H), 3.52 (d, J=5.7 Hz, 1H), 3.00 (d, J=17.5 Hz, 1H), 2.74 (dd, J=17.7, 6.1 Hz, 1H), 2.55 (dd, J=12.5, 2.8 Hz, 1H), 2.36-2.27 (m, 2H), 2.27-2.12 (m, 4H), 2.09-1.97 (m, 2H), 1.18-1.06 (m, 1H), 0.77-0.66 (m, 1H), 0.37 (d, J=7.7 Hz, 2H), 0.05--0.05 (m, 2H).

LC/MS, m/z=367.2 [M+H]$^+$ (Calc: 367.48).

PTSA (3.53 g, 18.6 mmol, 1.5 eq) was added to a solution of ketal 16 (5.0 g, 12.4 mmol, 1.0 eq) in acetone (400 mL) and the mixture was heated to reflux for 16 h. The mixture was concentrated and DCM was added. The pH was adjusted to 9-10 with saturated aqueous $NaHCO_3$ and the layers were separated. The aqueous layer was extracted with DCM and combined organic layers were dried over $MgSO_4$. The concentrated crude oil was purified by flash chromatography ($SiO_2$, 0-100%, acetone/hexanes) to obtain a light brown sticky foam. 2.2g (55.0% yield) of compound 17 was prepared.

$^1$H NMR: $\delta_H$ (400 MHz, $CD_3OD$): ): 6.77 (d, J=8.5 Hz, 1H), 6.71 (dd, J=10.0, 1.7 Hz, 1H), 6.54 (d, J=2.6 Hz, 1H), 6.47 (dd, J=8.5, 2.6 Hz, 1H), 5.60 (dd, J=10.0, 2.8 Hz, 1H), 3.50 (s, 3H), 3.41 (t, J=3.9 Hz, 1H), 3.02 (d, J=16.0 Hz, 1H), 2.86-2.79 (m, 2H), 2.61-2.54 (m, 1H), 2.49-2.33 (m, 3H), 2.19 (dd, J=12.7, 6.7 Hz, 1H), 1.90-1.78 (m, 2H), 1.35-1.26 (m, 1H), 0.76-0.65 (m, 1H), 0.40-0.32 (m, 2H), 0.05--0.57 (m, 2H).

LC/MS, m/s=323.4 [M+H]$^+$ (Calc: 323.43).

TFA (2.62 mL, 34.0 mmol, 5.0 eq) was added to a solution of enone 17 in MeOH (100 mL). The mixture was stirred for 20 min and then the mixture was cooled to −78° C. Ozone (Pacific Ozone Technology L21 ozone generator) was bubbled in for 10 min and the cooling bath was removed. Excess ozone was removed by bubbling nitrogen for 2 min at room temperature. 10% Aqueous NaOH (19.05 mL, 47.6 mmol, 7 eq) was added and the mixture was stirred for 30 min. The mixture was concentrated and water was added. The pH was adjusted to 5-6 with 20% HCl and DCM was added. The aqueous layer was extracted with DCM and the combined organic layers were dried over $MgSO_4$. The concentrated light brown sticky foam was carried forward as is. 1.18 g (50.5% yield) of compound 18 was obtained.

LC/MS, m/z=343.4 [M+H]$^+$ (Calc: 343.41).

A LAH solution (1.75 mL, 3.49 mmol, 3 eq, 2N in THF) was added to a solution, of lactol 18 (0.4 g, 1.17 mmol, 1 eq) in THF (10 mL) at 0° C. The cooling bath was removed and the mixture was stirred at 80° C. for 16 h. Ether (20 mL) was added and the mixture was quenched with wet $Na_2SO_4$. $MgSO_4$ was added and filtered through a pad of Celite. The mixture was concentrated and purified by reverse-phase prep HPLC (C18, 0-100% 0.1% TFA in water/0.1% TFA in ACN) to obtain a white solid, 271 mg (70.2% yield) of compound 19 was prepared as its TFA salt.

$^1$H NMR: $\delta_H$ (400 MHz, $CD_3OD$): 7.16 (d, J=8.3 Hz, 1H), 6.89 (d, J=2.4 Hz, 1H), 6.50 (dd, J=8.5, 2.1 Hz, 1H), s (4.31, 1H), 3.96-3.84 (m, 3H), 3.78 (s, 3H), 3.52-3.34 (m, 1H), 3.28-3.00 (m, 5H), 2.69 (dt, J=3.5, 13.8 Hz, 1H), 2.54-2.38 (m, 2H), 2.38-2.26 (m, 1H), 2.08-1.96 (m, 1H), 1.54 (d, J=13.1 Hz, 1H), 1.20-1.08 (m, 1H), 0.80 (d, J=7.2 Hz, 2H), 0.60-0.44 (m, 2H).

LC/MS, m/z=331.3 [M+H]$^+$ (Calc: 331.45).

$NaBH_4$ (132 mg, 3.49 mmol, 3 eq) was added to a solution of lactol 18 (0.4g, 1.17 mmol, 1 eq) in THF (20 mL) at 0° C. The cooling bath was removed and the mixture was stirred at RT for 16 h. The mixture was quenched with water. The mixture was acidified to pH 5 with 10% HCl. The organic layer was separated and the aqueous layer was extracted with DCM. The combined organic layers were dried over $MgSO_4$. The concentrated crude hydroxy acid 20 was carried forward as is.

LC/MS, m/z=345.4 [M+H]$^+$ (Calc: 345.43).

Thionyl chloride (84 μL, 1.16 mmol, 2 eq) was added dropwise to a solution of hydroxy acid 20 (200 mg, 0.579 mmol, 1 eq) in MeOH (10 ml) at 0° C. The mixture was heated to reflux for 2 h. The mixture was concentrated and the crude hydroxy ester 21 was carried forward as is.

LC/MS, m/z=359.4 [M+H]$^+$ (Calc: 359.46).

A solution of hydroxy ester 2.1 (1.90 mg, 0.480 mmol, 1 eq) in ammonia solution (10 mL, 1 N in MeOH) was stirred at 40° C. for 16 h. The mixture was concentrated and purified by reverse-phase prep HPLC (C18, 0-100% 0.1% TFA in water/0.1% TFA in ACN) to obtain a white solid. 41 mg (10% yield over 3 steps) of compound 22 was prepared as its TFA salt.

$^1$H NMR: $\delta_H$ (400 MHz, $CD_3OD$): 7.16 (d, J=8.1 Hz, 1H), 6.90-6.84 (m, 2H), s (4.24, 1H), 4.01 (dd, J=11.1, 5.4, 1H), 3.79 (s, 3H), 3.30-3.00 (m, 7H), 2.90-2.80 (m, 2H), 2.67 (d, J=14.5 Hz, 2H), 1.58 (d, J=14.0 Hz, 1H), 1.16-1.06 (m, 1H), 0.81-0.74 (m, 2H), 0.50-0.44 (m, 2H).

LC/MS, m/z=344.3 [M+H]$^+$ (Calc: 344.45).

Example 4

The following Tables provide results on the efficacy of binding and activity response of exemplified Compounds of the Invention at the μ- and κ-opioid receptors.

In TABLE 1, binding affinity of certain Compounds of the Invention to the μ- and κ-opioid receptors was determined as described above.

In TABLE 2, activity response of certain Compounds of the Invention at the μ- and κ-opioid receptors was determined as described above for functional assays.

TABLE I

Binding Affinity of Benzomorphan Analog Compounds

| Ref. No. | Compound | $K_i$ (nM) Opioid Receptor | |
|---|---|---|---|
| | | μ | κ |
| 10 | | 977.19 ± 335.16 | 64.47 ± 11.34 |
| 11 | | 621.40 ± 47.50 | 33.15 ± 2.98 |
| 12 | | 853.30 ± 199.10 | 42.53 ± 4.24 |
| 13 | | 1343.00 ± 356.00 | 66.82 ± 8.74 |

TABLE I-continued

Binding Affinity of Benzomorphan Analog Compounds

| Ref. No. | Compound | $K_i$ (nM) Opioid Receptor | |
|---|---|---|---|
| | | μ | κ |
| 19 | (structure) | | 89.61 ± 32.96 |
| 22 | (structure) | | 79.08 ± 19.13 |

TABLE 2

Activity Response of Benzomorphan Analog Compounds

| Ref. No. | GTPγS (EC$_{50}$: nM, E$_{max}$: %) Opioid Receptor | | | |
|---|---|---|---|---|
| | μ | | κ | |
| | EC$_{50}$ | E$_{max}$ | EC$_{50}$ | E$_{max}$ |
| 10 | 70.46 ± 26.94 | 16.00 ± 3.00 | 274.80 ± 43.64 | 31.33 ± 1.86 |
| 11 | 295.57 ± 55.49 | 56.00 ± 5.20 | 918.41 ± 178.16 | 86.67 ± 2.03 |
| 12 | 421.49 ± 140.28 | 48.67 ± 3.53 | 1003.14 ± 106.31 | 74.67 ± 1.20 |
| 13 | 742.82 ± 195.37 | 44.33 ± 9.06 | 554.76 ± 61.14 | 74.33 ± 7.84 |
| 19 | >20 μM | | 1860.65 ± 230.76 | 40.33 ± 5.36 |
| 22 | 1278.93 ± 176.71 | 56.00 ± 3.61 | 2179.68 ± 326.19 | 41.67 ± 4.91 |

The in vitro test results of Tables 1 and 2 show that representative Compounds of the Invention generally bind to opioid receptors, and that these compounds activate these receptors as partial to full agonists. Compounds of the Invention are therefore expected to be useful to treat Conditions, particularly pain, that are responsive to activation of one or more opioid receptors.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound of Formula I:

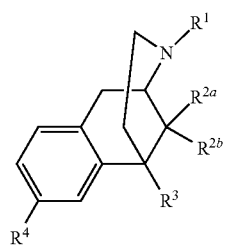

I wherein

R$^1$ is —(C$_3$-C$_{12}$)cycloalkyl, or (C$_3$-C$_{12}$)cycloalkyl-(C$_1$-C$_6$)alkyl-each of which is optionally substituted by 1, 2 or 3 independently selected R$^9$ groups;

R$^{2a}$ is absent, H, OH, or hydroxy(C$_1$-C$_6$)alkyl- wherein hydroxyl(C$_1$-C$_6$)alkyl- is a straight-chain C$_1$-C$_6$ alkyl group substituted by one or more hydroxy qroups;

R$^{2b}$ is selected from the group consisting of:
 a) -(6- to 14-membered)aryl or -(3- to 12-membered) heterocycle, each of which is optionally substituted with one, two, or three independently selected R$^{30}$ groups; and
 b) —Z-G-R$^{10}$;

$R^3$ is selected from the group consisting of:
  a) -(6- to 14-membered)aryl or -(3- to 12-membered)heterocycle, each of which is optionally substituted with one, two, or three independently selected $R^{30}$ groups; and
  b) —Z-G-$R^{10}$;
    provided that when $R^3$ is —Z-G-$R^{10}$ is than hydrogen, unsubstituted —($C_1$-$C_6$)alkyl, unsubstituted —($C_2$-$C_6$)alkenyl, or unsubstituted —($C_2$-$C_6$)alkyl;
wherein each Z is independently absent or —($CH_2$)$_m$—, optionally substituted with one or two —($C_1$-$C_6$)alkyl;
each G is independently selected from the group consisting of:
  a) a bond, —($C_1$-$C_6$)alkylene, and —($C_2$-$C_6$)alkenylene;
  b) O, —O—C(=O)—, —C(=O), and =CH;
  c) $NR^8$, =N—O, and =N—NH; and
  d) S, SO, and $SO_2$;
Each $R^{10}$ is independently selected from the group consisting of:
  a) hydrogen, —($C_1$-$C_{10}$)alkyl, —($C_2$-$C_{12}$)alkenyl, —CH(=O), —C(=O)—($C_1$-$C_6$)alkyl, —C(=O)—($C_2$-$C_6$)alkenyl, —C(=O)—(6- to 14-membered)aryl, —C(O)-($C_1$-$C_6$)alkyl-(6- to 14-membered)aryl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(6- to 14-membered)aryl, ((6- to14-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, and ((7- to 12-membered)bicycloheterocycle)-($C_1$-$C_6$)alkyl-, each of which is optionally substituted with one, two, or three $R^{40}$ groups; and
  b) —$NH_2$, —NH($C_1$-$C_6$)alkyl, CN, —$NR^5R^6$, —($C_1$-$C_6$)alkyl-$NR^5R^6$, —$CONR^5R^6$, —($C_1$-$C_6$)alkyl-$CONR^5R^6$, —$COOR^7$, —($C_1$-$C_6$)alkyl-$COOR^7$, —($C_1$-$C_6$)alkoxy-$COOR^7$, —C(O)—($CH_2$)$_n$—$COOR^7$, and —O—($CH_2$)$_n$—$CONR^5R^6$each of which is optionally substituted with one, two, or three $R^{41}$ groups;
each $R^{40}$ is independently selected from the group consisting of OH, (=O), halo, —C(halo)$_3$, —CH(halo)$_2$, —$CH_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, —$NH_2$, —NH($C_1$-$C_6$)alkyl, —($C_1$-$C_6$)alkyl-NH($C_1$-$C_6$)alkyl-$R^{14}$, —CN, —SH, —$OR^{11}$, —$CONR^5R^6$, —($C_1$-$C_6$alkyl)—$CONR^5R^6$, —COOR', —($C_1$-$C_6$)alkyl-$COOR^7$, —($C_1$-$C_6$)alkoxy-$COOR^7$, —(OCH$_2$CH$_2$)$_s$—O($C_1$-$C_6$)alkyl, —(CH$_2$CH$_2$O)$_s$-($C_1$-$C_6$)alkyl, ($C_1$-$C_6$)alkyl)sulfonyl, (($C_1$-$C_6$)alkyl)sulfonyl($C_1$-$C_6$)alkyl-, —NH-$SO_2$($C_1$-$C_6$)alkyl, $NH_2$—$SO_2$($C_1$-$C_6$)alkyl-, —N($SO_2$($C_1$-$C_6$)alkyl)$_2$, —C(=NH)$NH_2$, —NH—CO—($C_1$-$C_6$)alkyl, —NH—CO—$NH_2$, —NH—C(=O)—NH—($C_1$-$C_6$)alkyl, —NH—C(=O)-(6- to 14-membered)aryl, —NH—C(=O)—($C_1$-$C_6$)alkyl-(6- to 14- membered)aryl, —NH—($C_1$-$C_6$)alkyl-$COOR^7$, —NH—C(=O)—($C_1$-$C_6$)alkyl-$COOR^7$, —NH—C(=O)—CH($NH_2$)—($C_1$-$C_6$)alkyl-$COOR^7$, —($C_3$-$C_{12}$)cycloalkyl, (($C_3$-$C_{12}$)cycloalkyl)-($C_1$-$C_6$)alkyl-, -(6- to 14-membered)aryl, -(6- to 14-membered)aryloxy, —($C_1$-$C_6$)alkoxy-$CONR^5R^6$, —NH—($C_1$-$C_6$)alkyl-$CONR^5R^6$, —C(=O)NH—($C_1$-$C_6$)alkyl-$COOR^7$, ((6- to 14-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

each $R^{41}$ is independently selected from the group consisting of —OH, (=O), halo, —C(halo)$_3$, —CH(halo)$_2$, —$CH_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, —($C_1$-$C_6$)alkyl-NH($C_1$-$C_6$)alkyl-$R^{14}$, —$CONR^{5a}R^{6a}$, —($C_1$-$C_6$alkyl-$CONR^{5a}R^{6a}$ $^a$, —($C_1$-$C_6$)alkyl-$COOR^7$, —($C_1$-$C_6$)alkoxy-$COOR^7$, —(CH$_2$CH$_2$O)$_s$—($C_1$-$C_6$)alkyl, ($C_1$-$C_6$)alkyl)sulfonyl, (($C_1$-$C_6$)alkyl)sulfonyl($C_1$-$C_6$)alkyl-, —C(=NH)$NH_2$, phenyl, benzyl, —($C_3$-$C_{12}$)cycloalkyl, (($C_3$-$C_{12}$)cycloalkyl)-($C_1$-$C_6$)alkyl-, -(6- to 14-membered)aryl, -(6- to 14-membered)aryloxy, ((6- to 14-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

provided that:
  a) when $R^{2a}$ is absent or OH, then $R^{2b}$ and $R^3$ are not H, —($C_1$-$C_6$)alkyl, —($C_2$-$C_6$)alkenyl, or —($C_2$-$C_6$)alkynyl, each of which is unsubstituted; or
  b) when $R^{2b}$ is Z-G-$R^{10}$, and G of $R^{2b}$ is =N—O, =N—NH, or =CH, and Z of $R^{2b}$ is absent, then $R^{2a}$ is absent; or
  c) when $R^3$ is Z-G-$R^{10}$, and G of $R^3$ is =N—O, =N—NH, or =CH, then Z of $R^3$ cannot be absent;

$R^4$ is selected from the group consisting of:
  a) —OH, halo, —C(halo)$_3$, —CH(halo)$_2$, —COOH, or —$CONH_2$; and
  b) —($C_1$-$C_6$)alkyl, and —($C_1$-$C_6$)alkoxy $R^5$ and $R^6$ are each independently selected from the group consisting of:
  a) hydrogen, —OH, halo, —C(halo)$_3$, —CH(halo)$_2$, and —$CH_2$(halo);
  b) —($C_1$-$C_6$)alkyl, —($C_2$-$C_6$)alkenyl, —($C_2$-$C_6$)alkynyl, —($CH_2$)$_n$—O—($CH_2$)$_n$-$CH_3$, and —($C_1$-$C_6$)alkoxy, each of which is optionally substituted with 1, 2, or 3 substituents independently selected from —OH, halo, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —CHO, —COON, —C(halo)$_3$, —CH(halo)$_2$, —$CH_2$(halo), —($CH_2$)$_n$—O—($CH_2$)$_n$—$CH_3$, phenyl, and —$CONR^{5a}R^{6a}$;
  c) —($C_3$-$C_8$)cycloalkyl, (($C_3$-$C_8$)cycloalkyl)-($C_1$-$C_6$)alkyl-, —$COOR^7$, —($C_1$-$C_6$)alkyl-$COOR^7$, —$CONH_2$, and ($C_1$-$C_6$)alkyl-CONH—;
  d) -(6- to 14-membered)aryl optionally substituted with 1, 2, or 3 independently selected $R^{30}$ groups; or e) R⁵ and R⁶ together with the nitrogen atom to which they are attached form a (4- to 8-membered)heterocycle optionally substituted with 1, 2, or 3 independently selected R³⁰ groups;

R⁵ᵃ and R⁶ᵃ are each independently selected from the group consisting of:
  a) hydrogen, —OH, halo, —C(halo)₃, —CH(halo)₂, and —CH₂(halo);
  b) —(C₁-C₆)alkyl, -(C₂-C₆)alkenyl, -(C₂-C₆)alkynyl, -(CH₂)ₙ—O—(CH₂)ₙ—CH₃, and —(C₁-C₆)alkoxy, each of which is optionally substituted with 1, 2, or 3 substituents independently selected from —OH, halo, —(C₁-C₁₀)alkyl, —(C₂-C₁₂)alkenyl, —(C₂-C₁₂)alkynyl, —(C₁-C₁₀)alkoxy, —(C₃-C₁₂)cycloalkyl, —CHO, —COON, —C(halo)₃, —CH(halo)₂, CH₂(halo), —(CH₂)ₙ—O—(CH₂)ₙ-CH₃, and phenyl;
  c) —(C₃-C₈)cycloalkyl, ((C₃-C₈)cycloalkyl)—(C₁-C₆)alkyl-, —COOR⁷, —(C₁-C₆)alkyl-COOR⁷, —CONH₂, and (C₁-C₆)alkyl-CONH—;
  d) —(6- to 14-membered)aryl optionally substituted with 1, 2, or 3 independently selected R³⁰ groups; or
  e) R⁵ᵃ and R⁶ᵃ together with the nitrogen atom to which they are attached form a (4- to 8-membered)heterocycle optionally substituted with 1, 2, or 3 independently selected R³⁰ groups;

each R⁷ is independently selected from the group consisting of hydrogen, —(C₁-C₆)alkyl, —(C₂-C₆)alkenyl, —(C₂-C₆)alkynyl, —(C₃-C₁₂)cycloalkyl, —(C₄-C₁₂)cycloalkenyl, ((C₃-C₁₂)cycloalkyl)-(C₁-C₆)alkyl-, and ((C₄-C₁₂)cycloalkenyl)-(C₁-C₆)alkyl-;

each R⁸ is independently selected from the group consisting of H, —(C₁-C₆)alkyl, —(C₂-C₆)alkenyl, —(C₂-C₆)alkynyl, —(C₁-C₁₀)alkoxy, —(C₃-C₁₂)cycloalkyl, —(C₃-C₁₂)cycloalkenyl, ((C₃-C₁₂)cycloalkyl)-(C₁-C₆)alkyl-, ((C₃-C₁₂)cycloalkenyl)-(C₁-C₆)alkyl-, —C(=O)(C₁-C₆)alkyl and SO₂(C₁-C₆)alkyl;

each R⁹ is independently selected from the group consisting of —OH, halo, —(C₁-C₁₀)alkyl, —(C₂-C₁₂)alkenyl, —(C₂-C₁₂)alkynyl, —(C₁-C₁₀)alkoxy, —(C₃-C₁₂)cycloalkyl, —CHO, —COOH, —C(halo)₃, —CH(halo)₂, —CH₂(halo), —(CH₂)ₙ—O—(CH₂)ₙ—CH₃, phenyl, and —CONR⁵ᵃR⁶ᵃ;

each R¹¹ is independently selected from the group consisting of —C(halo)₃, —CH(halo)₂, —CH₂(halo), —(C₁-C₆)alkyl, —(C₂-C₆)alkenyl, —(C₂-C₆)alkynyl, —(CH₂)ₙ—O—(CH₂)ₙ—CH₃, -(6- to 14-membered)aryl, ((6- to 14-membered)aryl)-(C₁-C₆)alkyl-, -(5- to 12-membered)heteroaryl, and ((5- to 12-membered)heteroaryl)-(C₁-C₆)alkyl-, each of which is optionally substituted with 1, 2 or 3 independently selected R⁹ groups;

each R¹⁴ is independently selected from the group consisting of —COOR⁷, —(C₁-C₆)alkyl-COOR⁷, —C(=O)—(C₁-C₆)alkyl-COOR⁷, —(C₁-C₆)alkyl-C(=O)—(C₁-C₆)alkyl-COOR⁷, —CONR⁵ᵃR⁶ᵃ, and —(C₁-C₆)alkyl-CONR⁵ᵃR⁶ᵃ;

each R³⁰ is independently selected from —COOR⁷, —CONR⁵ᵃR⁶ᵃ, —(C₁-C₆)alkyl, CN, —(3- to 12-membered)heteroaryl, ((3- to 12-membered)heteroaryl)-(C₁-C₆)alkyl-, NH₂, halo, and ((6- to 14-membered)aryl)-(C₁-C₆)alkoxy-;

m is an integer 1, 2, 3, 4, 5, or 6;
n is an integer 0, 1, 2, 3, 4, 5, or 6;
s in an integer 1, 2, 3, 4, 5, or 6;
or a pharmaceutically acceptable salt or solvate thereof.

2. A compound of claim 1 having Formula IA:

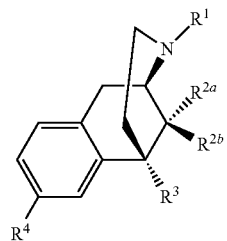

wherein R¹ R²ᵃ, R²ᵇ, R³ and R⁴ are as defined above for Formula I, or a pharmaceutically acceptable salt or solvate thereof.

3. A compound of claim 1, having Formula IB:

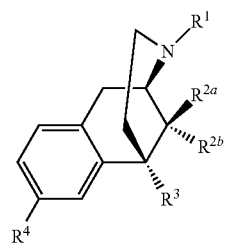

wherein R¹ R²ᵃ, R²ᵇ, R³ and R⁴ are as defined above for Formula I, or a pharmaceutically acceptable salt or solvate thereof.

4. A compound of claim 1, having Formula IC:

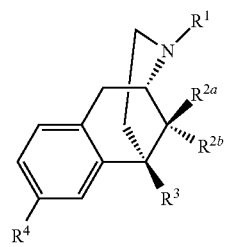

wherein R¹ R²ᵃ, R²ᵇ, R³ and R⁴ are as defined above for Formula I, or a pharmaceutically acceptable salt or solvate thereof.

5. A compound of claim 1, having Formula ID:

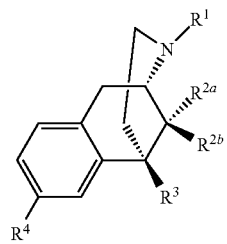

wherein R¹ R²ᵃ, R²ᵇ, R³ and R⁴ are as defined above for Formula I, or a pharmaceutically acceptable salt or solvate thereof.

6. A compound of claim 1, wherein $R^{2a}$ is absent.

7. A compound of claim 1, wherein $R^{2b}$ is -(6- to 14-membered)aryl or -(3- to 12-membered)heterocycle, each of which is optionally substituted with one, two, or three independently selected $R^{30}$ groups.

8. A compound of claim 1, wherein $R^3$ is -(6- to 14-membered)aryl or -(3- to 12-membered)heterocycle, each of which is optionally substituted with one, two, or three independently selected $R^{30}$ groups.

9. A compound of claim 1, wherein $R^{2b}$ is —Z-G-$R^{10}$, provided that —Z-G-$R^{10}$ is other than hydrogen, or unsubstituted —($C_1$-$C_6$)alkyl, unsubstituted —($C_2$-$C_6$)alkenyl, or unsubstituted -($C_2$-$C_6$)alkynyl.

10. A compound of claim 1, wherein $R^{2b}$ and $R^3$ are different.

11. A compound of claim 1, wherein $R^{2b}$ and $R^3$ are the same.

12. A compound selected from the group consisting of:
4-((2R,6R,11R)-11-(carboxymethyl)-3-(cyclopropylmethyl)-8-hydroxy-1,2,3,4,5,6-hexahydro-2,6-methanobenzo[d]azocin-6-yl)butanoic acid;
(Z)-2-((2R,6S)-6-(4-amino-4-oxobutyl)-3-(cyclopropylmethyl)-8-hydroxy-1,2,3,4,5,6-hexahydro-2,6-methanobenzo[d]azocin-11-ylidene)acetic acid;
(Z)-2-((2R,6S)-3-(cyclopropylmethyl)-6-(4-(dimethylamino)-4-oxobutyl)-8-hydroxy-1,2,3,4,5,6-hexahydro-2,6-methanobenzo[d]azocin-11-ylidene)acetic acid;
4-((2R,6S,Z)-11-(carboxymethylene)-3-(cyclopropylmethyl)-8-hydroxy-1,2,3,4,5,6-hexahydro-2,6-methanobenzo[d]azocin-6-yl)butanoic acid;
2-((2R,6S,11R)-3-(cyclopropylmethyl)-11-(hydroxymethyl)-8-methoxy-1,2,3,4,5,6-hexahydro-2,6-methanobenzo[d]azocin-6-yl)ethanol;
2-((2R,6S,11R)-3-(cyclopropylmethyl)-11-(hydroxymethyl)-8-methoxy-1,2,3,4,5,6-hexahydro-2,6-methanobenzo[d]azocin-6-yl)acetamide;
and the pharmaceutically acceptable salts and solvates thereof.

13. A pharmaceutical composition comprising an effective amount of a compound of claim 1, or a pharmaceutically acceptable salt or solvate thereof, and a pharmaceutically acceptable carrier or excipient.

14. A method of treating a Condition in a mammal, comprising administering to such mammal in need thereof an effective amount of a compound of claim 1, or a pharmaceutically acceptable salt or solvate thereof, wherein said Condition is selected from a group consisting of: pain, alcohol withdrawal, drug withdrawal, addictive disorders, pruritis, constipation, and diarrhea.

15. The method of claim 14, wherein the Condition is pain.

16. The method of claim 14, wherein the Condition is constipation.

17. A method for preparing a composition, comprising the step of admixing a compound according to claim 1, or a pharmaceutically acceptable salt or solvate thereof, with a pharmaceutically acceptable carrier or excipient.

18. The compound of claim 1, wherein $R^{2a}$ is hydroxyl($C_1$-$C_6$)alkyl-, wherein hydroxy($C_1$-$C_6$)alkyl- is a straight-chain $C_1$-$C_6$ alkyl group substituted by one or more hydroxy groups.

19. The compound of claim 1, wherein $R^1$ is (($C_3$-$C_{12}$)cycloalkyl)-($C_1$-$C_6$)alkyl-.

20. The compound of claim 19, wherein $R^1$ is cyclopropylmethyl.

21. The compound of claim 1, wherein $R^4$ is ($C_1$-$C_6$) alkoxy.

22. The compound of claim 21, wherein $R^4$ is methoxy.

* * * * *